(12) United States Patent
Aga et al.

(10) Patent No.: US 11,407,831 B2
(45) Date of Patent: Aug. 9, 2022

(54) PHARMACEUTICAL COMPOSITION ADMINISTERED IN COMBINATION WITH SUBSTITUTED DIHYDROPYRROLOPYRAZOLE COMPOUND AND IMMUNOTHERAPEUTIC AGENT

(71) Applicant: UBE INDUSTRIES, LTD., Ube (JP)

(72) Inventors: Yasuhiro Aga, Ube (JP); Sayaka Ogi, Ube (JP)

(73) Assignee: UBE INDUSTRIES, LTD., Ube (JP)

( * ) Notice: Subject to any disclaimer, the term of this patent is extended or adjusted under 35 U.S.C. 154(b) by 0 days.

(21) Appl. No.: 16/758,519

(22) PCT Filed: Oct. 29, 2018

(86) PCT No.: PCT/JP2018/040085
§ 371 (c)(1),
(2) Date: Apr. 23, 2020

(87) PCT Pub. No.: WO2019/088016
PCT Pub. Date: May 9, 2019

(65) Prior Publication Data
US 2020/0262924 A1 Aug. 20, 2020

(30) Foreign Application Priority Data
Oct. 30, 2017 (JP) .............................. JP2017-208951

(51) Int. Cl.
*A61P 35/00* (2006.01)
*C07K 16/28* (2006.01)

(52) U.S. Cl.
CPC .......... *C07K 16/2818* (2013.01); *A61P 35/00* (2018.01)

(58) Field of Classification Search
CPC .............................. C07K 16/2828; A61P 35/00
See application file for complete search history.

(56) References Cited

U.S. PATENT DOCUMENTS

2016/0303124 A1\* 10/2016 Webster .................. A61P 31/12
2018/0186818 A1   7/2018 Iwase et al.

FOREIGN PATENT DOCUMENTS

WO     2016204153 A1    12/2016

OTHER PUBLICATIONS

May 14, 2020 International Preliminary Report on Patentability issued in International Patent Application No. PCT/JP2018/040085.

Dec. 11, 2018 International Search Report issued in International Patent Application No. PCT/JP2018/040085.
Robert P. Fisher; "Secrets of a Double Agent: CDK7 in Cell-Cycle Control and Transcription;" Journal of Cell Science 2005; vol. 118; pp. 5171-5180.
Marcos Malumbres et al.; "Cell Cycle, CDKs and Cancer: A Changing Paradigm;" Nature Reviews Cancer; 2009; vol. 9; pp. 153-166.
Jesper Q. Svejstrup; "The RNA Polymerase II Transcription Cycle: Cycling Through Chromatin;" Biochimica et Biophysica Acta; 2004; vol. 1677; pp. 64-73.
Nicholas Kwiatkowski et al.; "Targeting Transcription Regulation in Cancer with a Covalent CDK7 Inhibitor;" NAture 2014; vol. 511; pp. 1-16.
Simak Ali et al.; "The Development of a Selective Cyclin-dependent Kinase Inhibitor Which Demonstrates Anti-Tumor Activity," Cancer Research; 2009; vol. 69; pp. 1-16.
Suzanne L. Topalian et. al.; "Safety, Activity, and Immune Correlates of Anti-PD-1 Antibody in Cancer;" The New England Journal of Medicine; 2012; vol. 366; pp. 2443-2454.
Adil. I. Daud et al.; "Tumor Immune Profiling Predicts Response to Anti-PD-1 Therapy in Human Melanoma;" The Journal of Clinical Investigation; 2016; vol. 126; pp. 3447-3452.
Sharma, Padmanee et al.; "Primary, Adaptive, and Acquired Resistance to Cancer Immunotherapy;" Cell; Feb. 9, 2017; vol. 168; pp. 707-723.
Dempke, Wolfram C.M. et al.; "Second-and Third-generation Drugs for Immuno-oncology Treatment—The More the Better?:" European Journal of Cancer; Feb. 10, 2017; vol. 74; pp. 55-72.

\* cited by examiner

*Primary Examiner* — Yong S. Chong
(74) *Attorney, Agent, or Firm* — Mintz, Levin, Cohn, Ferris, Glovsky and Popeo, P.C.

(57) ABSTRACT

A pharmaceutical composition including a compound represented by the formula (I) or a pharmacologically acceptable salt thereof wherein two R moieties each independently are a $C_{1-3}$ alkyl group or are groups bonded to each other to form a $C_{2-5}$ alkylene group; A is an optionally substituted $C_{6-10}$ aryl group or an optionally substituted heteroaryl group; and $R^1$, $R^2$ and $R^3$ each independently are an optionally substituted linear or branched $C_{1-4}$ alkyl group, wherein the pharmaceutical composition is administered in combination with an immunotherapeutic agent.

(I)
[Chemical Formula 1]

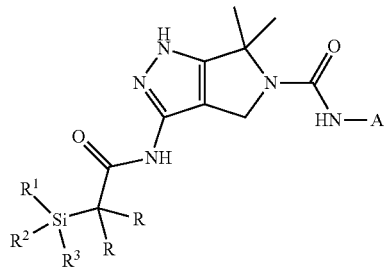

12 Claims, No Drawings

PHARMACEUTICAL COMPOSITION ADMINISTERED IN COMBINATION WITH SUBSTITUTED DIHYDROPYRROLOPYRAZOLE COMPOUND AND IMMUNOTHERAPEUTIC AGENT

TECHNICAL FIELD

The present invention relates to a pharmaceutical composition wherein a substituted dihydropyrrolopyrazole compound or a pharmacologically acceptable salt thereof, and an immunotherapeutic agent are administered in combination.

BACKGROUND ART

CDKs (cyclin-dependent kinases) are cell growth control factors that are involved in entry to DNA synthesis (S phase) of the cell cycle and a mitotic phase (M phase), etc., and many types of CDKs are known. Also, the activation of CDK is controlled in multiple stages through the phosphorylation or dephosphorylation of the threonine residue of active loop (T loop) in its three-dimensional structure. When the particular threonine residue of CDK is phosphorylated, it forms a complex with a particular cyclin and is activated. This complex, which is important for cell cycle control, includes CDK1, CDK2/cyclin A, CDK1/cyclins B1 to B3 and CDK2, CDK4, CDK5, CDK6/cyclin D1 to D3, and CDK2/cyclin E, which are respectively involved in the particular periods of the cell cycle. CDK7 forms a CDK-activating kinase (CAK) together with cyclin H and MAT1 in metazoans and participates in the phosphorylation of CDKs (e.g., CDK1, CDK2, CDK4, and CDK6) necessary for the progression of the cell cycle (see Non Patent Literature 1).

Cell overgrowth by the abnormal activation of CDKs is a common feature in many cancers, and it is known that this is associated with a loss of checkpoint functions involved in the cell cycle control of cancer cells (see Non Patent Literature 2). Also, CDKs are known to have functions other than cell cycle control, and CDK7 is known to promote the binding of RNA polymerase II (RNAPII) to DNA and elongation thereof to positively control the transcription through the phosphorylation of serine in the COOH-terminal domain of the RNAPII (see Non Patent Literature 3).

CDK7 inhibitors exhibit effects in cell growth tests of various cancer cells and cancer-bearing mouse models, and the inhibition is expected to be useful as anticancer agents (see Patent Literature 1, Non Patent Literatures 4 and 5).

Genetic and epigenetic alterations, which are characteristic of cancers, bring about antigens that are recognized by the immune system and can be used to differentiate between tumor cells and their healthy equivalents. In principle, this means that the immune system can serve as a powerful weapon for controlling tumor. However, the reality is that the immune system usually does not provide a strong response to tumor cells. The activation of T cells is controlled positively or negatively by stimulation mediated by an antigen receptor (TCR) expressed on the cell membrane, and by co-stimulation mediated by a co-stimulatory molecule group. The activated T cells are suppressed by molecules, such as CTLA-4 and PD-1, which work as negative feedback, and through the use of this mechanism, cancer cells suppress the activated T cells, thereby escaping from the immune surveillance mechanism and continuing to proliferate.

Hence, as for a method for avoiding the suppression of T cells by cancer cells, it is considered effective for cancer treatment that T cell activation is induced by treatment with inhibitory antibodies against inhibitory co-stimulatory molecules on T cells, and Non Patent Literature 6 focuses on PD-1 (expressed on T cells) and PD-L1 or PD-L2 (expressed on cancer cells), which are involved in the suppression of T cells, as a new target in cancer treatment, and discloses a technique relating to the recovery of an immune function by a substance inhibiting PD-1, PD-L1, or PD-L2, and further to an immunotherapeutic agent containing an anti-PD-1 antibody, an anti-PD-L1 antibody, or an anti-PD-L2 antibody based on the proliferation suppression of cancer cells via an activation mechanism.

Although a high therapeutic effect has been confirmed as to immunotherapeutic agents in recent years, there are also unresponsive cases or cases insufficiently responsive thereto (see Non Patent Literature 7) and thus, a challenge is the development of novel methods effective for these cases.

Various combination therapies have been practiced as one of the methods for solving the challenge (see Non Patent Literature 8). Here, although Patent Literature 1 discloses a combination of an immune checkpoint inhibitor and a CDK7 inhibitor, there is no report on any case in which a combination therapy of an immunotherapeutic agent and a CDK7 inhibitor has actually been practiced.

CITATION LIST

Patent Literature

Patent Literature 1: WO 2016/204153

Non Patent Literature

Non Patent Literature 1: Journal of Cell Science 2005, 118 (20), 5171-5180
Non Patent Literature 2: Nature Reviews Cancer 2009, 9, 153-166
Non Patent Literature 3: Biochim Biophys Acta 2004, 1677, 64-73
Non Patent Literature 4: Nature 2014, 511, 616-620
Non Patent Literature 5: Cancer Research 2009, 69, 6208-6215
Non Patent Literature 6: The New England Journal of Medicine 2012, 366, 2443-2454
Non Patent Literature 7: The Journal of Clinical Investigation 2016, 126(9), 3347-3452
Non Patent Literature 8: Cell 2017, 168(4), 707-723

SUMMARY OF INVENTION

Technical Problem

The present inventors have completed the present invention by finding that a pharmaceutical composition comprising a substituted dihydropyrrolopyrazole compound having CDK7 inhibitory activity or a pharmacologically acceptable salt thereof, the pharmaceutical composition being administered in combination with an immunotherapeutic agent, is useful as a drug for the treatment and/or prevention (preferably, a drug for the treatment) of tumor.

Solution to Problem

The present invention provides a pharmaceutical composition (preferably, a pharmaceutical composition for the treatment or prevention of tumor) comprising a substituted dihydropyrrolopyrazole compound or a pharmacologically acceptable salt thereof, wherein the pharmaceutical composition is administered in combination with an immunotherapeutic agent;

use of the substituted dihydropyrrolopyrazole compound or the pharmacologically acceptable salt thereof, and an immunotherapeutic agent in combination for the production of a pharmaceutical composition for the treatment or prevention (preferably, treatment) of tumor; and a method for treating or preventing (preferably, treating) tumor by administering pharmaceutically effective amounts of the substituted dihydropyrrolopyrazole compound or the pharmacologically acceptable salt thereof, and an immunotherapeutic agent in combination to a warm-blooded animal (preferably, a human).

Examples of the tumors include urinary bladder cancer, breast cancer, large intestine cancer (e.g., colorectal cancer, for example, colon adenocarcinoma and colon adenoma), kidney cancer, epidermal cancer, liver cancer, lung cancer (e.g., adenocarcinoma, small-cell lung cancer, and non-small cell lung cancer), esophageal cancer, gallbladder cancer, ovary cancer, pancreatic cancer (e.g., exocrine pancreatic tumor), gastric cancer, cervical cancer, endometrial cancer, thyroid gland cancer, cancer of the nose, head and neck cancer, prostate cancer, skin cancer (e.g., squamous cell cancer), hematopoietic organ tumors of the lymphatic system (e.g., leukemia, acute lymphatic leukemia, chronic lymphatic leukemia, B cell lymphoma (e.g., diffuse large B cell lymphoma), T cell lymphoma, multiple myeloma, Hodgkin's lymphoma, non-Hodgkin's lymphoma, hairy cell lymphoma, and Burkitt's lymphoma), hematopoietic organ tumors of the myeloid system (e.g., acute or chronic myeloid leukemia, myelodysplastic syndrome, and promyelocytic leukemia), follicular carcinoma of thyroid, mesenchymal tumors (e.g., fibrosarcoma, Ewing's sarcoma, and rhabdomyosarcoma), tumors of the central or peripheral nervous system (e.g., astrocytoma, neuroblastoma, glioma, brain tumor, and schwannoma), melanoma, seminoma, teratoma, osteosarcoma, xeroderma pigmentosum, keratoacanthoma, follicular carcinoma of thyroid, and Kaposi's sarcoma.

According to one aspect, the present invention provides the following [1] to [16]:

[1] A pharmaceutical composition comprising a compound represented by the formula (I) or a pharmacologically acceptable salt thereof:

[Chemical Formula 1]

(I)

wherein
two R moieties each independently are a $C_{1-3}$ alkyl group or are groups bonded to each other to form a $C_{2-5}$ alkylene group;

A is an optionally substituted $C_{6-10}$ aryl group or an optionally substituted heteroaryl group; and $R^1$, $R^2$ and $R^3$ each independently are an optionally substituted linear or branched $C_{1-4}$ alkyl group, wherein
the pharmaceutical composition is administered in combination with an immunotherapeutic agent.

[2] A pharmaceutical composition comprising a compound represented by the formula (II) or a pharmacologically acceptable salt thereof:

[Chemical Formula 2]

(II)

wherein
A is an optionally substituted $C_{6-10}$ aryl group or an optionally substituted heteroaryl group; and $R^1$, $R^2$ and $R^3$ each independently are an optionally substituted linear or branched $C_{1-4}$ alkyl group, wherein
the pharmaceutical composition is administered in combination with an immunotherapeutic agent.

[3] A pharmaceutical composition comprising a compound selected from the compound group consisting of N-(2-fluorophenyl)-6,6-dimethyl-3-[1-(trimethylsilyl)cyclobutanecarboxamido]-4,6-dihydropyrrolo[3,4-c]pyrazole-5(1H)-carboxamide, 6,6-Dimethyl-N-(o-tolyl)-3-[1-(trimethylsilyl)cyclobutanecarboxamido]-4,6-dihydropyrrolo[3,4-c]pyrazole-5(1H)-carboxamide, N-(2-chloro-6-methylphenyl)-6,6-dimethyl-3-[1-(trimethylsilyl)cyclobutanecarboxamido]-4,6-dihydropyrrolo[3,4-c]pyrazole-5(1H)-carboxamide, N-(5-fluoro-2-methylphenyl)-6,6-dimethyl-3-[1-(trimethylsilyl)cyclobutanecarboxamido]-4,6-dihydropyrrolo[3,4-c]pyrazole-5(1H)-carboxamide, N-(2,5-dimethylphenyl)-6,6-dimethyl-3-[1-(trimethylsilyl)cyclobutanecarboxamido]-4,6-dihydropyrrolo[3,4-c]pyrazole-5(1H)-carboxamide, N-(2-chloro-6-fluorophenyl)-6,6-dimethyl-3-[1-(trimethylsilyl)cyclobutanecarboxamido]-4,6-dihydropyrrolo[3,4-c]pyrazole-5(1H)-carboxamide, N-(2-bromo-6-methylphenyl)-6,6-dimethyl-3-[1-(trimethylsilyl)cyclobutanecarboxamido]-4,6-dihydropyrrolo[3,4-c]pyrazole-5(1H)-carboxamide, N-(2-fluoro-3,6-dimethylphenyl)-6,6-dimethyl-3-[1-(trimethylsilyl)cyclobutanecarboxamido]-4,6-dihydropyrrolo[3,4-c]pyrazole-5(1H)-carboxamide, N-(6-fluorobenzofuran-7-yl)-6,6-dimethyl-3-[1-(trimethylsilyl)cyclobutanecarboxamido]-4,6-dihydropyrrolo[3,4-c]pyrazole-5(1H)-carboxamide, N-(2-chloro-6-fluorobenzofuran-7-yl)-6,6-dimethyl-3-[1-(trimethylsilyl) cyclobutanecarboxamido]-4,6-dihydropyrrolo[3,4-c]pyrazole-5(1H)-carboxamide, and N-(6-fluoro-2-methylbenzofuran-7-yl)-6,6-dimethyl-3-[1-(trimethylsilyl)cyclobutanecarboxamido]-4,6-dihydropyrrolo[3,4-c]pyrazole-5(1H)-carboxamide or a pharmacologically acceptable salt thereof, wherein
the pharmaceutical composition is administered in combination with an immunotherapeutic agent.

[4] A pharmaceutical composition wherein a composition comprising a compound or a pharmacologically acceptable salt thereof according to any of [1] to [3] as an active ingredient, and a composition comprising an immunotherapeutic agent as an active ingredient are administered at the same time or at a different time.

[5] A pharmaceutical composition comprising a compound or a pharmacologically acceptable salt thereof according to any of [1] to [3], and an immunotherapeutic agent as active ingredients.

[6] The pharmaceutical composition according to any of [1] to [5], wherein the immunotherapeutic agent is an agent that inhibits an immune checkpoint selected from the group consisting of CTLA-4, PD-1, PD-L1, TIM-3, KIR, LAG-3, VISTA and BTLA, or an agent that activates immunity selected from the group consisting of OX40, IL-10R, GITR, CD27, CD28, CD137 and ICOS.

[7] The pharmaceutical composition according to any of [1] to [5], wherein the immunotherapeutic agent is selected from the group consisting of ipilimumab, tremelimumab, nivolumab, pembrolizumab, pidilizumab, JNJ-63723283, durvalumab (MEDI4736), atezolizumab (RG7446), avelumab (MSB0010718C), BMS-936559, LY3300054, FAZ053, and MPDL3280A.

[8] The pharmaceutical composition according to any of [1] to [5], wherein the immunotherapeutic agent is selected from the group consisting of AM0010, GSK3174998, MOXR0916, PF-04518600, MEDI0562, TRX518, MEDI1873, varlilumab, urelumab, utomilumab, and MEDI-570.

[9] The pharmaceutical composition according to any of [1] to [5], wherein the immunotherapeutic agent is an antibody.

[10] The pharmaceutical composition according to [9], wherein the antibody is an anti-CTLA-4 antibody or an anti-PD-1 antibody.

[11] The pharmaceutical composition according to [10], wherein the anti-PD-1 antibody is nivolumab, pembrolizumab or pidilizumab.

[12] The pharmaceutical composition according to any of [1] to [11], wherein the pharmaceutical composition is for the treatment or prevention of tumor.

[13] A method for treating or preventing tumor, comprising administering a compound or a pharmacologically acceptable salt thereof according to any of [1] to [3] and one or more immunotherapeutic agents in combination to a subject in need thereof.

[14] Use of a compound or a pharmacologically acceptable salt thereof according to any of [1] to [3] and one or more immunotherapeutic agents in combination for the production of a pharmaceutical composition being a therapeutic agent or a prophylactic agent for tumor.

[15] Use of a compound or a pharmacologically acceptable salt thereof according to any of [1] to [3] and one or more immunotherapeutic agents in combination for the treatment or prevention of tumor.

[16] A combination of a compound or a pharmacologically acceptable salt thereof according to any of [1] to [3] and one or more immunotherapeutic agents for use in the treatment or prevention of tumor.

According to another aspect, the present invention provides the following [17] to [40]:

[17] A pharmaceutical composition comprising N-(2-fluorophenyl)-6,6-dimethyl-3-[1-(trimethylsilyl)cyclobutanecarboxamido]-4,6-dihydropyrrolo[3,4-c]pyrazole-5(1H)-carboxamide or a pharmacologically acceptable salt thereof, wherein
the pharmaceutical composition is administered in combination with an immunotherapeutic agent.

[18] A pharmaceutical composition comprising 6,6-Dimethyl-N-(o-tolyl)-3-[1-(trimethylsilyl)cyclobutanecarboxamido]-4,6-dihydropyrrolo[3,4-c]pyrazole-5(1H)-carboxamide or a pharmacologically acceptable salt thereof, wherein
the pharmaceutical composition is administered in combination with an immunotherapeutic agent.

[19] A pharmaceutical composition comprising N-(2-chloro-6-methylphenyl)-6,6-dimethyl-3-[1-(trimethylsilyl)cyclobutanecarboxamido]-4,6-dihydropyrrolo[3,4-c]pyrazole-5(1H)-carboxamide or a pharmacologically acceptable salt thereof, wherein
the pharmaceutical composition is administered in combination with an immunotherapeutic agent.

[20] A pharmaceutical composition comprising N-(5-fluoro-2-methylphenyl)-6,6-dimethyl-3-[1-(trimethylsilyl)cyclobutanecarboxamido]-4,6-dihydropyrrolo[3,4-c]pyrazole-5(1H)-carboxamide or a pharmacologically acceptable salt thereof, wherein
the pharmaceutical composition is administered in combination with an immunotherapeutic agent.

[21] A pharmaceutical composition comprising N-(2,5-dimethylphenyl)-6,6-dimethyl-3-[1-(trimethylsilyl)cyclobutanecarboxamido]-4,6-dihydropyrrolo[3,4-c]pyrazole-5(1H)-carboxamide or a pharmacologically acceptable salt thereof, wherein
the pharmaceutical composition is administered in combination with an immunotherapeutic agent.

[22] A pharmaceutical composition comprising N-(2-chloro-6-fluorophenyl)-6,6-dimethyl-3-[1-(trimethylsilyl)cyclobutanecarboxamido]-4,6-dihydropyrrolo[3,4-c]pyrazole-5(1H)-carboxamide or a pharmacologically acceptable salt thereof, wherein
the pharmaceutical composition is administered in combination with an immunotherapeutic agent.

[23] A pharmaceutical composition comprising N-(2-bromo-6-methylphenyl)-6,6-dimethyl-3-[1-(trimethylsilyl)cyclobutanecarboxamido]-4,6-dihydropyrrolo[3,4-c]pyrazole-5(1H)-carboxamide or a pharmacologically acceptable salt thereof, wherein
the pharmaceutical composition is administered in combination with an immunotherapeutic agent.

[24] A pharmaceutical composition comprising N-(2-fluoro-3,6-dimethylphenyl)-6,6-dimethyl-3-[1-(trimethylsilyl)cyclobutanecarboxamido]-4,6-dihydropyrrolo[3,4-c]pyrazole-5(1H)-carboxamide or a pharmacologically acceptable salt thereof, wherein
the pharmaceutical composition is administered in combination with an immunotherapeutic agent.

[25] A pharmaceutical composition comprising N-(6-fluorobenzofuran-7-yl)-6,6-dimethyl-3-[1-(trimethylsilyl)cyclobutanecarboxamido]-4,6-dihydropyrrolo[3,4-c]pyrazole-5(1H)-carboxamide or a pharmacologically acceptable salt thereof, wherein
the pharmaceutical composition is administered in combination with an immunotherapeutic agent.

[26] A pharmaceutical composition comprising N-(2-chloro-6-fluorobenzofuran-7-yl)-6,6-dimethyl-3-[1-(trimethylsilyl)cyclobutanecarboxamido]-4,6-dihydropyrrolo[3,4-c]pyrazole-5(1H)-carboxamide or a pharmacologically acceptable salt thereof, wherein the pharmaceutical composition is administered in combination with an immunotherapeutic agent.

[27] A pharmaceutical composition comprising N-(6-fluoro-2-methylbenzofuran-7-yl)-6,6-dimethyl-3-[1-(trimethylsilyl)cyclobutanecarboxamido]-4,6-dihydropyrrolo[3,4-c]pyrazole-5(1H)-carboxamide or a pharmacologically acceptable salt thereof, wherein
the pharmaceutical composition is administered in combination with an immunotherapeutic agent.

[28] A pharmaceutical composition wherein a composition comprising a compound or a pharmacologically acceptable salt thereof according to any of [17] to [27] as an active ingredient, and a composition comprising an immunotherapeutic agent as an active ingredient are administered at the same time or at a different time.

[29] A pharmaceutical composition comprising a compound or a pharmacologically acceptable salt thereof according to any of [17] to [27], and an immunotherapeutic agent as active ingredients.

[30] The pharmaceutical composition according to any of [17] to [29], wherein the immunotherapeutic agent is an agent that inhibits an immune checkpoint selected from the group consisting of CTLA-4, PD-1, PD-L1, TIM-3, KIR, LAG-3, VISTA and BTLA, or an agent that activates immunity selected from the group consisting of OX40, IL-10R, GITR, CD27, CD28, CD137 and ICOS.

[31] The pharmaceutical composition according to any of [17] to [29], wherein the immunotherapeutic agent is selected from the group consisting of ipilimumab, tremelimumab, nivolumab, pembrolizumab, pidilizumab, JNJ-63723283, durvalumab (MEDI4736), atezolizumab (RG7446), avelumab (MSB0010718C), BMS-936559, LY3300054, FAZ053, and MPDL3280A.

[32] The pharmaceutical composition according to any of [17] to [29], wherein the immunotherapeutic agent is selected from the group consisting of AM0010, GSK3174998, MOXR0916, PF-04518600, MEDI0562, TRX518, MEDI1873, varlilumab, urelumab, utomilumab, and MEDI-570.

[33] The pharmaceutical composition according to any of [17] to [29], wherein the immunotherapeutic agent is an antibody.

[34] The pharmaceutical composition according to [33], wherein the antibody is an anti-CTLA-4 antibody or an anti-PD-1 antibody.

[35] The pharmaceutical composition according to [34], wherein the anti-PD-1 antibody is nivolumab, pembrolizumab or pidilizumab.

[36] The pharmaceutical composition according to any of [1] to [11], wherein the pharmaceutical composition is for the treatment or prevention of tumor.

[37] A method for treating or preventing tumor, comprising administering a compound or a pharmacologically acceptable salt thereof according to any of [17] to [27] and one or more immunotherapeutic agents in combination to a subject in need thereof.

[38] Use of a compound or a pharmacologically acceptable salt thereof according to any of [17] to [27] and one or more immunotherapeutic agents in combination for the production of a pharmaceutical composition being a therapeutic agent or a prophylactic agent for tumor.

[39] Use of a compound or a pharmacologically acceptable salt thereof according to any of [17] to [27] and one or more immunotherapeutic agents in combination for the treatment or prevention of tumor.

[40] A combination of a compound or a pharmacologically acceptable salt thereof according to any of [17] to [27] and one or more immunotherapeutic agents for use in the treatment or prevention of tumor.

Examples of the compound represented by the formula (I) of the present invention include compounds represented by the following formulas (II), (III), and (IV):

[Chemical Formula 3]

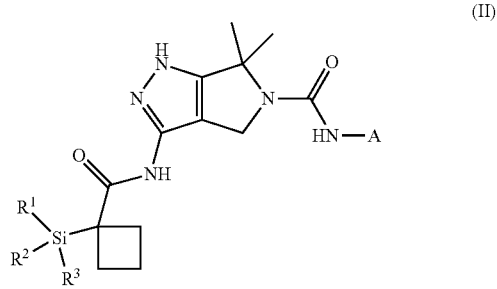

(II)

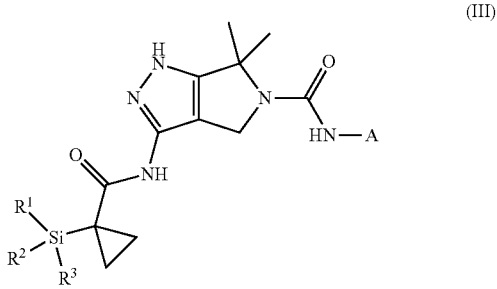

(III)

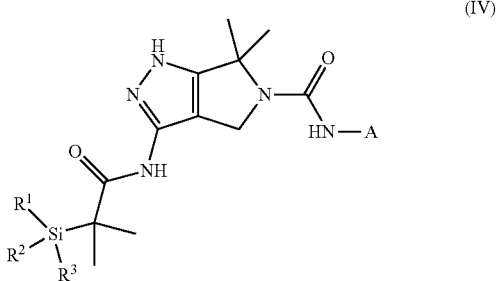

(IV)

wherein A is an optionally substituted $C_{6-10}$ aryl group or an optionally substituted heteroaryl group; and $R^1$, $R^2$ and $R^3$ each independently are an optionally substituted linear or branched $C_{1-4}$ alkyl group. Among them, the compound represented by the formula (II) is preferred.

Specific examples of the compound represented by the general formula (II) of the present invention can include compounds as shown in Tables 1 to 12 below. In Tables 1 to 12 below, D represents deuterium, Br represents a bromine atom, Cl represents a chlorine atom, F represents a fluorine atom, Me represents a methyl group, Et represents an ethyl group, nPr represents a n-propyl group, iPr represents an isopropyl group, cPr represents a cyclopropyl group, tBu represents a tert-butyl group, Ph represents a phenyl group, and MeO represents a methoxy group. As specific examples, "$CF_3$" represents a trifluoromethyl group, "$CHF_2O$" represents a difluoromethoxy group, "$CD_3$" represents a group in which three hydrogen atoms constituting the methyl group are replaced with deuterium atoms, "1,1-diF-Et" means a group in which the ethyl group is substituted at position 1 by two fluorine atoms, i.e., a 1,1,-difluoroethyl group, "2,6-diF-Ph" means a group in which the phenyl group is substituted at positions 2 and 6 by fluorine atoms, respectively, i.e., a 2,6-difluorophenyl group, "2,4-diCl-6-Me-Ph" means a group in which the phenyl group is substituted at positions 2 and 4 by chlorine atoms, respectively, and substituted at position 6 by a methyl group, i.e., a 2,4-dichloro-6-methylphenyl group, and "CH₂CH₂CH₂CH₂" means a 1,4-butylene group formed by bonding two R moieties to each other.

TABLE 1

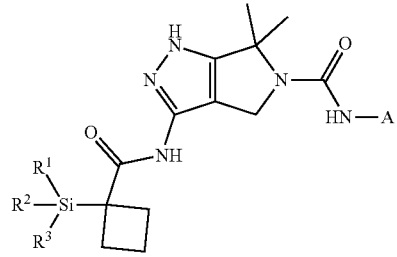

(II)

| Comp. No. | R¹ | R² | R³ | A |
|---|---|---|---|---|
| II-1 | Me | Me | Me | Ph |
| II-2 | Me | Et | Me | Ph |
| II-3 | Me | Me | Me | 2-F—Ph |
| II-4 | Me | Et | Me | 2-F—Ph |
| II-5 | Me | Me | Me | 3-F—Ph |
| II-6 | Me | Et | Me | 3-F—Ph |
| II-7 | Me | Me | Me | 4-F—Ph |
| II-8 | Me | Et | Me | 4-F—Ph |
| II-9 | Me | Me | Me | 2-Cl—Ph |
| II-10 | Me | Et | Me | 2-Cl—Ph |
| II-11 | Me | Me | Me | 3-Cl—Ph |
| II-12 | Me | Et | Me | 3-Cl—Ph |
| II-13 | Me | Me | Me | 4-Cl—Ph |
| II-14 | Me | Et | Me | 4-Cl—Ph |
| II-15 | Me | Me | Me | 2-Br—Ph |
| II-16 | Me | Et | Me | 2-Br—Ph |
| II-17 | Me | Me | Me | 3-Br—Ph |
| II-18 | Me | Et | Me | 3-Br—Ph |
| II-19 | Me | Me | Me | 4-Br—Ph |
| II-20 | Me | Et | Me | 4-Br—Ph |
| II-21 | Me | Me | Me | 2-Me—Ph |
| II-22 | Me | Et | Me | 2-Me—Ph |
| II-23 | Me | Me | Me | 3-Me—Ph |
| II-24 | Me | Et | Me | 3-Me—Ph |
| II-25 | Me | Me | Me | 4-Me—Ph |
| II-26 | Me | Et | Me | 4-Me—Ph |
| II-27 | Me | Me | Me | 2-Et—Ph |
| II-28 | Me | Et | Me | 2-Et—Ph |
| II-29 | Me | Me | Me | 3-Et—Ph |
| II-30 | Me | Et | Me | 3-Et—Ph |
| II-31 | Me | Me | Me | 4-Et—Ph |
| II-32 | Me | Et | Me | 4-Et—Ph |
| II-33 | Me | Me | Me | 2-iPr—Ph |
| II-34 | Me | Et | Me | 2-iPr—Ph |
| II-35 | Me | Me | Me | 3-iPr—Ph |
| II-36 | Me | Et | Me | 3-iPr—Ph |
| II-37 | Me | Me | Me | 4-iPr—Ph |
| II-38 | Me | Et | Me | 4-iPr—Ph |
| II-39 | Me | Me | Me | 2-cPr—Ph |
| II-40 | Me | Et | Me | 2-cPr—Ph |
| II-41 | Me | Me | Me | 3-cPr—Ph |
| II-42 | Me | Et | Me | 3-cPr—Ph |
| II-43 | Me | Me | Me | 4-cPr—Ph |
| II-44 | Me | Et | Me | 4-cPr—Ph |
| II-45 | Me | Me | Me | 2-(1,1-diF—Et)—Ph |
| II-46 | Me | Et | Me | 2-(1,1-diF—Et)—Ph |
| II-47 | Me | Me | Me | 3-(1,1-diF—Et)—Ph |
| II-48 | Me | Et | Me | 3-(1,1-diF—Et)—Ph |
| II-49 | Me | Me | Me | 4-(1,1-diF—Et)—Ph |
| II-50 | Me | Et | Me | 4-(1,1-diF—Et)—Ph |
| II-51 | Me | Me | Me | 2-CF₃—Ph |
| II-52 | Me | Et | Me | 2-CF₃—Ph |
| II-53 | Me | Me | Me | 3-CF₃—Ph |
| II-54 | Me | Et | Me | 3-CF₃—Ph |
| II-55 | Me | Me | Me | 4-CF₃—Ph |
| II-56 | Me | Et | Me | 4-CF₃—Ph |
| II-57 | Me | Me | Me | 2-tBu—Ph |
| II-58 | Me | Et | Me | 2-tBu—Ph |
| II-59 | Me | Me | Me | 3-tBu—Ph |
| II-60 | Me | Et | Me | 3-tBu—Ph |
| II-61 | Me | Me | Me | 4-tBu—Ph |
| II-62 | Me | Et | Me | 4-tBu—Ph |
| II-63 | Me | Me | Me | 2-NC—Ph |
| II-64 | Me | Et | Me | 2-NC—Ph |
| II-65 | Me | Me | Me | 3-NC—Ph |
| II-66 | Me | Et | Me | 3-NC—Ph |
| II-67 | Me | Me | Me | 4-NC—Ph |
| II-68 | Me | Et | Me | 4-NC—Ph |
| II-69 | Me | Me | Me | 2-Ph—Ph |
| II-70 | Me | Et | Me | 2-Ph—Ph |
| II-71 | Me | Me | Me | 3-Ph—Ph |
| II-72 | Me | Et | Me | 3-Ph—Ph |
| II-73 | Me | Me | Me | 4-Ph—Ph |
| II-74 | Me | Et | Me | 4-Ph—Ph |
| II-75 | Me | Me | Me | 2-MeO—Ph |
| II-76 | Me | Et | Me | 2-MeO—Ph |
| II-77 | Me | Me | Me | 3-MeO—Ph |
| II-78 | Me | Et | Me | 3-MeO—Ph |
| II-79 | Me | Me | Me | 4-MeO—Ph |
| II-80 | Me | Et | Me | 4-MeO—Ph |
| II-81 | Me | Me | Me | 2-EtO—Ph |
| II-82 | Me | Et | Me | 2-EtO—Ph |
| II-83 | Me | Me | Me | 3-EtO—Ph |
| II-84 | Me | Et | Me | 3-EtO—Ph |
| II-85 | Me | Me | Me | 4-EtO—Ph |
| II-86 | Me | Et | Me | 4-EtO—Ph |
| II-87 | Me | Me | Me | 2-CHF₂O—Ph |
| II-88 | Me | Et | Me | 2-CHF₂O—Ph |
| II-89 | Me | Me | Me | 3-CHF₂O—Ph |
| II-90 | Me | Et | Me | 3-CHF₂O—Ph |
| II-91 | Me | Me | Me | 4-CHF₂O—Ph |
| II-92 | Me | Et | Me | 4-CHF₂O—Ph |
| II-93 | Me | Me | Me | 2-CF₃O—Ph |
| II-94 | Me | Et | Me | 2-CF₃O—Ph |
| II-95 | Me | Me | Me | 3-CF₃O—Ph |
| II-96 | Me | Et | Me | 3-CF₃O—Ph |
| II-97 | Me | Me | Me | 4-CF₃O—Ph |
| II-98 | Me | Et | Me | 4-CF₃O—Ph |
| II-99 | Me | Me | Me | 2,3-diF—Ph |
| II-100 | Me | Et | Me | 2,3-diF—Ph |

TABLE 2

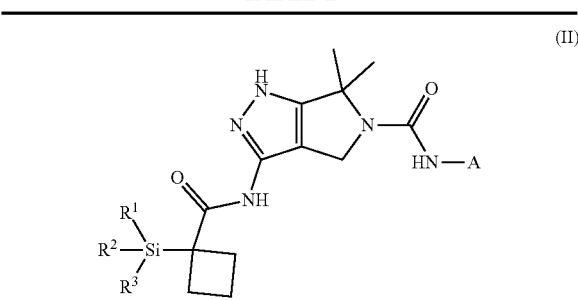

(II)

| Comp. No. | R¹ | R² | R³ | A |
|---|---|---|---|---|
| II-101 | Me | Me | Me | 2,4-diF—Ph |
| II-102 | Me | Et | Me | 2,4-diF—Ph |
| II-103 | Me | Me | Me | 2,5-diF—Ph |
| II-104 | Me | Et | Me | 2,5-diF—Ph |
| II-105 | Me | Me | Me | 2,6-diF—Ph |
| II-106 | Me | Et | Me | 2,6-diF—Ph |
| II-107 | Me | Me | Me | 2-F-3-Cl—Ph |
| II-108 | Me | Et | Me | 2-F-3-Cl—Ph |
| II-109 | Me | Me | Me | 2-F-4-Cl—Ph |
| II-110 | Me | Et | Me | 2-F-4-Cl—Ph |
| II-111 | Me | Me | Me | 2-F-5-Cl—Ph |
| II-112 | Me | Et | Me | 2-F-5-Cl—Ph |
| II-113 | Me | Me | Me | 2-F-6-Cl—Ph |
| II-114 | Me | Et | Me | 2-F-6-Cl—Ph |
| II-115 | Me | Me | Me | 2-F-3-Br—Ph |
| II-116 | Me | Et | Me | 2-F-3-Br—Ph |
| II-117 | Me | Me | Me | 2-F-4-Br—Ph |
| II-118 | Me | Et | Me | 2-F-4-Br—Ph |
| II-119 | Me | Me | Me | 2-F-5-Br—Ph |
| II-120 | Me | Et | Me | 2-F-5-Br—Ph |
| II-121 | Me | Me | Me | 2-F-6-Br—Ph |
| II-122 | Me | Et | Me | 2-F-6-Br—Ph |
| II-123 | Me | Me | Me | 2-F-3-Me—Ph |
| II-124 | Me | Et | Me | 2-F-3-Me—Ph |
| II-125 | Me | Me | Me | 2-F-4-Me—Ph |
| II-126 | Me | Et | Me | 2-F-4-Me—Ph |
| II-127 | Me | Me | Me | 2-F-5-Me—Ph |
| II-128 | Me | Et | Me | 2-F-5-Me—Ph |
| II-129 | Me | Me | Me | 2-F-6-Me—Ph |
| II-130 | Me | Et | Me | 2-F-6-Me—Ph |
| II-131 | Me | Me | Me | 2-F-3-Et—Ph |
| II-132 | Me | Et | Me | 2-F-3-Et—Ph |
| II-133 | Me | Me | Me | 2-F-4-Et—Ph |
| II-134 | Me | Et | Me | 2-F-4-Et—Ph |
| II-135 | Me | Me | Me | 2-F-5-Et—Ph |
| II-136 | Me | Et | Me | 2-F-5-Et—Ph |
| II-137 | Me | Me | Me | 2-F-6-Et—Ph |
| II-138 | Me | Et | Me | 2-F-6-Et—Ph |
| II-139 | Me | Me | Me | 2-F-3-cPr—Ph |
| II-140 | Me | Et | Me | 2-F-3-cPr—Ph |
| II-141 | Me | Me | Me | 2-F-4-cPr—Ph |
| II-142 | Me | Et | Me | 2-F-4-cPr—Ph |
| II-143 | Me | Me | Me | 2-F-5-cPr—Ph |
| II-144 | Me | Et | Me | 2-F-5-cPr—Ph |
| II-145 | Me | Me | Me | 2-F-6-cPr—Ph |
| II-146 | Me | Et | Me | 2-F-6-cPr—Ph |
| II-147 | Me | Me | Me | 2-F-3-CF₃—Ph |
| II-148 | Me | Et | Me | 2-F-3-CF₃—Ph |
| II-149 | Me | Me | Me | 2-F-4-CF₃—Ph |
| II-150 | Me | Et | Me | 2-F-4-CF₃—Ph |
| II-151 | Me | Me | Me | 2-F-5-CF₃—Ph |
| II-152 | Me | Et | Me | 2-F-5-CF₃—Ph |
| II-153 | Me | Me | Me | 2-F-6-CF₃—Ph |
| II-154 | Me | Et | Me | 2-F-6-CF₃—Ph |
| II-155 | Me | Me | Me | 2-F-3-MeO—Ph |
| II-156 | Me | Et | Me | 2-F-3-MeO—Ph |
| II-157 | Me | Me | Me | 2-F-4-MeO—Ph |
| II-158 | Me | Et | Me | 2-F-4-MeO—Ph |
| II-159 | Me | Me | Me | 2-F-5-MeO—Ph |
| II-160 | Me | Et | Me | 2-F-5-MeO—Ph |
| II-161 | Me | Me | Me | 2-F-6-MeO—Ph |
| II-162 | Me | Et | Me | 2-F-6-MeO—Ph |
| II-163 | Me | Me | Me | 2-F-3-CHF₂O—Ph |
| II-164 | Me | Et | Me | 2-F-3-CHF₂O—Ph |

TABLE 2-continued

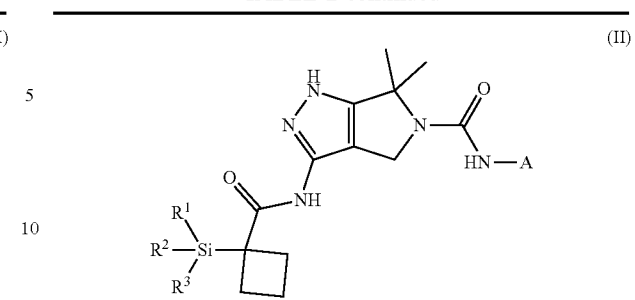

(II)

| Comp. No. | R¹ | R² | R³ | A |
|---|---|---|---|---|
| II-165 | Me | Me | Me | 2-F-4-CHF₂O—Ph |
| II-166 | Me | Et | Me | 2-F-4-CHF₂O—Ph |
| II-167 | Me | Me | Me | 2-F-5-CHF₂O—Ph |
| II-168 | Me | Et | Me | 2-F-5-CHF₂O—Ph |
| II-169 | Me | Me | Me | 2-F-6-CHF₂O—Ph |
| II-170 | Me | Et | Me | 2-F-6-CHF₂O—Ph |
| II-171 | Me | Me | Me | 2-F-3-CD₃O—Ph |
| II-172 | Me | Et | Me | 2-F-3-CD₃O—Ph |
| II-173 | Me | Me | Me | 2-F-4-CD₃O—Ph |
| II-174 | Me | Et | Me | 2-F-4-CD₃O—Ph |
| II-175 | Me | Me | Me | 2-F-5-CD₃O—Ph |
| II-176 | Me | Et | Me | 2-F-5-CD₃O—Ph |
| II-177 | Me | Me | Me | 2-F-6-CD₃O—Ph |
| II-178 | Me | Et | Me | 2-F-6-CD₃O—Ph |
| II-179 | Me | Me | Me | 2-F-3-NC—Ph |
| II-180 | Me | Et | Me | 2-F-3-NC—Ph |
| II-181 | Me | Me | Me | 2-F-4-NC—Ph |
| II-182 | Me | Et | Me | 2-F-4-NC—Ph |
| II-183 | Me | Me | Me | 2-F-5-NC—Ph |
| II-184 | Me | Et | Me | 2-F-5-NC—Ph |
| II-185 | Me | Me | Me | 2-F-6-NC—Ph |
| II-186 | Me | Et | Me | 2-F-6-NC—Ph |
| II-187 | Me | Me | Me | 2-Cl-3-F—Ph |
| II-188 | Me | Et | Me | 2-Cl-3-F—Ph |
| II-189 | Me | Me | Me | 2-Cl-4-F—Ph |
| II-190 | Me | Et | Me | 2-Cl-4-F—Ph |
| II-191 | Me | Me | Me | 2-Cl-5-F—Ph |
| II-192 | Me | Et | Me | 2-Cl-5-F—Ph |
| II-193 | Me | Me | Me | 2,3-diCl—Ph |
| II-194 | Me | Et | Me | 2,3-diCl—Ph |
| II-195 | Me | Me | Me | 2,4-diCl—Ph |
| II-196 | Me | Et | Me | 2,4-diCl—Ph |
| II-197 | Me | Me | Me | 2,5-diCl—Ph |
| II-198 | Me | Et | Me | 2,5-diCl—Ph |
| II-199 | Me | Me | Me | 2,6-diCl—Ph |
| II-200 | Me | Et | Me | 2,6-diCl—Ph |

TABLE 3

(II)

| Comp. No. | R¹ | R² | R³ | A |
|---|---|---|---|---|
| II-201 | Me | Me | Me | 2-Cl-3-Br—Ph |
| II-202 | Me | Et | Me | 2-Cl-3-Br—Ph |
| II-203 | Me | Me | Me | 2-Cl-4-Br—Ph |
| II-204 | Me | Et | Me | 2-Cl-4-Br—Ph |
| II-205 | Me | Me | Me | 2-Cl-5-Br—Ph |
| II-206 | Me | Et | Me | 2-Cl-5-Br—Ph |

TABLE 3-continued

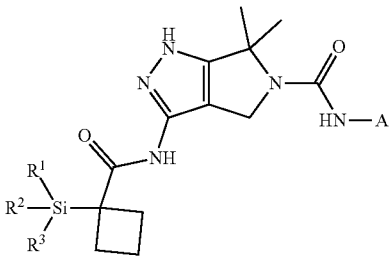

(II)

| Comp. No. | R¹ | R² | R³ | A |
|---|---|---|---|---|
| II-207 | Me | Me | Me | 2-Cl-6-Br—Ph |
| II-208 | Me | Et | Me | 2-Cl-6-Br—Ph |
| II-209 | Me | Me | Me | 2-Cl-3-Me—Ph |
| II-210 | Me | Et | Me | 2-Cl-3-Me—Ph |
| II-211 | Me | Me | Me | 2-Cl-4-Me—Ph |
| II-212 | Me | Et | Me | 2-Cl-4-Me—Ph |
| II-213 | Me | Me | Me | 2-Cl-5-Me—Ph |
| II-214 | Me | Et | Me | 2-Cl-5-Me—Ph |
| II-215 | Me | Me | Me | 2-Cl-6-Me—Ph |
| II-216 | Me | Et | Me | 2-Cl-6-Me—Ph |
| II-217 | Me | Me | Me | 2-Cl-3-Et—Ph |
| II-218 | Me | Et | Me | 2-Cl-3-Et—Ph |
| II-219 | Me | Me | Me | 2-Cl-4-Et—Ph |
| II-220 | Me | Et | Me | 2-Cl-4-Et—Ph |
| II-221 | Me | Me | Me | 2-Cl-5-Et—Ph |
| II-222 | Me | Et | Me | 2-Cl-5-Et—Ph |
| II-223 | Me | Me | Me | 2-Cl-6-Et—Ph |
| II-224 | Me | Et | Me | 2-Cl-6-Et—Ph |
| II-225 | Me | Me | Me | 2-Cl-3-cPr—Ph |
| II-226 | Me | Et | Me | 2-Cl-3-cPr—Ph |
| II-227 | Me | Me | Me | 2-Cl-4-cPr—Ph |
| II-228 | Me | Et | Me | 2-Cl-4-cPr—Ph |
| II-229 | Me | Me | Me | 2-Cl-5-cPr—Ph |
| II-230 | Me | Et | Me | 2-Cl-5-cPr—Ph |
| II-231 | Me | Me | Me | 2-Cl-6-cPr—Ph |
| II-232 | Me | Et | Me | 2-Cl-6-cPr—Ph |
| II-233 | Me | Me | Me | 2-Cl-3-$CF_3$—Ph |
| II-234 | Me | Et | Me | 2-Cl-3-$CF_3$—Ph |
| II-235 | Me | Me | Me | 2-Cl-4-$CF_3$—Ph |
| II-236 | Me | Et | Me | 2-Cl-4-$CF_3$—Ph |
| II-237 | Me | Me | Me | 2-Cl-5-$CF_3$—Ph |
| II-238 | Me | Et | Me | 2-Cl-5-$CF_3$—Ph |
| II-239 | Me | Me | Me | 2-Cl-6-$CF_3$—Ph |
| II-240 | Me | Et | Me | 2-Cl-6-$CF_3$—Ph |
| II-241 | Me | Me | Me | 2-Cl-3-MeO—Ph |
| II-242 | Me | Et | Me | 2-Cl-3-MeO—Ph |
| II-243 | Me | Me | Me | 2-Cl-4-MeO—Ph |
| II-244 | Me | Et | Me | 2-Cl-4-MeO—Ph |
| II-245 | Me | Me | Me | 2-Cl-5-MeO—Ph |
| II-246 | Me | Et | Me | 2-Cl-5-MeO—Ph |
| II-247 | Me | Me | Me | 2-Cl-6-MeO—Ph |
| II-248 | Me | Et | Me | 2-Cl-6-MeO—Ph |
| II-249 | Me | Me | Me | 2-Cl-3-$CHF_2$O—Ph |
| II-250 | Me | Et | Me | 2-Cl-3-$CHF_2$O—Ph |
| II-251 | Me | Me | Me | 2-Cl-4-$CHF_2$O—Ph |
| II-252 | Me | Et | Me | 2-Cl-4-$CHF_2$O—Ph |
| II-253 | Me | Me | Me | 2-Cl-5-$CHF_2$O—Ph |
| II-254 | Me | Et | Me | 2-Cl-5-$CHF_2$O—Ph |
| II-255 | Me | Me | Me | 2-Cl-6-$CHF_2$O—Ph |
| II-256 | Me | Et | Me | 2-Cl-6-$CHF_2$O—Ph |
| II-257 | Me | Me | Me | 2-Cl-3-$CD_3$O—Ph |
| II-258 | Me | Et | Me | 2-Cl-3-$CD_3$O—Ph |
| II-259 | Me | Me | Me | 2-Cl-4-$CD_3$O—Ph |
| II-260 | Me | Et | Me | 2-Cl-4-$CD_3$O—Ph |
| II-261 | Me | Me | Me | 2-Cl-5-$CD_3$O—Ph |
| II-262 | Me | Et | Me | 2-Cl-5-$CD_3$O—Ph |
| II-263 | Me | Me | Me | 2-Cl-6-$CD_3$O—Ph |
| II-264 | Me | Et | Me | 2-Cl-6-$CD_3$O—Ph |
| II-265 | Me | Me | Me | 2-Cl-3-NC—Ph |
| II-266 | Me | Et | Me | 2-Cl-3-NC—Ph |
| II-267 | Me | Me | Me | 2-Cl-4-NC—Ph |
| II-268 | Me | Et | Me | 2-Cl-4-NC—Ph |
| II-269 | Me | Me | Me | 2-Cl-5-NC—Ph |
| II-270 | Me | Et | Me | 2-Cl-5-NC—Ph |

TABLE 3-continued

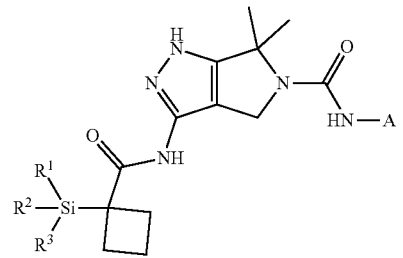

(II)

| Comp. No. | R¹ | R² | R³ | A |
|---|---|---|---|---|
| II-271 | Me | Me | Me | 2-Cl-6-NC—Ph |
| II-272 | Me | Et | Me | 2-Cl-6-NC—Ph |
| II-273 | Me | Me | Me | 2-Br-3-F—Ph |
| II-274 | Me | Et | Me | 2-Br-3-F—Ph |
| II-275 | Me | Me | Me | 2-Br-4-F—Ph |
| II-276 | Me | Et | Me | 2-Br-4-F—Ph |
| II-277 | Me | Me | Me | 2-Br-5-F—Ph |
| II-278 | Me | Et | Me | 2-Br-5-F—Ph |
| II-279 | Me | Me | Me | 2-Br-3-Cl—Ph |
| II-280 | Me | Et | Me | 2-Br-3-Cl—Ph |
| II-281 | Me | Me | Me | 2-Br-4-Cl—Ph |
| II-282 | Me | Et | Me | 2-Br-4-Cl—Ph |
| II-283 | Me | Me | Me | 2-Br-5-Cl—Ph |
| II-284 | Me | Et | Me | 2-Br-5-Cl—Ph |
| II-285 | Me | Me | Me | 2,3-diBr—Ph |
| II-286 | Me | Et | Me | 2,3-diBr—Ph |
| II-287 | Me | Me | Me | 2,4-diBr—Ph |
| II-288 | Me | Et | Me | 2,4-diBr—Ph |
| II-289 | Me | Me | Me | 2,5-diBr—Ph |
| II-290 | Me | Et | Me | 2,5-diBr—Ph |
| II-291 | Me | Me | Me | 2,6-diBr—Ph |
| II-292 | Me | Et | Me | 2,6-diBr—Ph |
| II-293 | Me | Me | Me | 2-Br-3-Me—Ph |
| II-294 | Me | Et | Me | 2-Br-3-Me—Ph |
| II-295 | Me | Me | Me | 2-Br-4-Me—Ph |
| II-296 | Me | Et | Me | 2-Br-4-Me—Ph |
| II-297 | Me | Me | Me | 2-Br-5-Me—Ph |
| II-298 | Me | Et | Me | 2-Br-5-Me—Ph |
| II-299 | Me | Me | Me | 2-Br-6-Me—Ph |
| II-300 | Me | Et | Me | 2-Br-6-Me—Ph |

TABLE 4

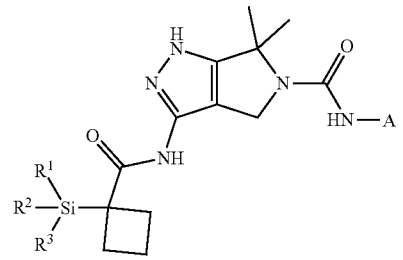

(II)

| Comp. No. | R¹ | R² | R³ | A |
|---|---|---|---|---|
| II-301 | Me | Me | Me | 2-Br-3-Et—Ph |
| II-302 | Me | Et | Me | 2-Br-3-Et—Ph |
| II-303 | Me | Me | Me | 2-Br-4-Et—Ph |
| II-304 | Me | Et | Me | 2-Br-4-Et—Ph |
| II-305 | Me | Me | Me | 2-Br-5-Et—Ph |
| II-306 | Me | Et | Me | 2-Br-5-Et—Ph |
| II-307 | Me | Me | Me | 2-Br-6-Et—Ph |
| II-308 | Me | Et | Me | 2-Br-6-Et—Ph |
| II-309 | Me | Me | Me | 2-Br-3-cPr—Ph |
| II-310 | Me | Et | Me | 2-Br-3-cPr—Ph |
| II-311 | Me | Me | Me | 2-Br-4-cPr—Ph |
| II-312 | Me | Et | Me | 2-Br-4-cPr—Ph |

TABLE 4-continued

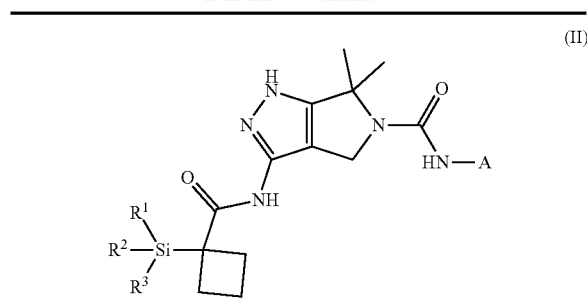

(II)

| Comp. No. | R¹ | R² | R³ | A |
|---|---|---|---|---|
| II-313 | Me | Me | Me | 2-Br-5-cPr—Ph |
| II-314 | Me | Et | Me | 2-Br-5-cPr—Ph |
| II-315 | Me | Me | Me | 2-Br-6-cPr—Ph |
| II-316 | Me | Et | Me | 2-Br-6-cPr—Ph |
| II-317 | Me | Me | Me | 2-Br-3-CF$_3$—Ph |
| II-318 | Me | Et | Me | 2-Br-3-CF$_3$—Ph |
| II-319 | Me | Me | Me | 2-Br-4-CF$_3$—Ph |
| II-320 | Me | Et | Me | 2-Br-4-CF$_3$—Ph |
| II-321 | Me | Me | Me | 2-Br-5-CF$_3$—Ph |
| II-322 | Me | Et | Me | 2-Br-5-CF$_3$—Ph |
| II-323 | Me | Me | Me | 2-Br-6-CF$_3$—Ph |
| II-324 | Me | Et | Me | 2-Br-6-CF$_3$—Ph |
| II-325 | Me | Me | Me | 2-Br-3-MeO—Ph |
| II-326 | Me | Et | Me | 2-Br-3-MeO—Ph |
| II-327 | Me | Me | Me | 2-Br-4-MeO—Ph |
| II-328 | Me | Et | Me | 2-Br-4-MeO—Ph |
| II-329 | Me | Me | Me | 2-Br-5-MeO—Ph |
| II-330 | Me | Et | Me | 2-Br-5-MeO—Ph |
| II-331 | Me | Me | Me | 2-Br-6-MeO—Ph |
| II-332 | Me | Et | Me | 2-Br-6-MeO—Ph |
| II-333 | Me | Me | Me | 2-Br-3-CHF$_2$O—Ph |
| II-334 | Me | Et | Me | 2-Br-3-CHF$_2$O—Ph |
| II-335 | Me | Me | Me | 2-Br-4-CHF$_2$O—Ph |
| II-336 | Me | Et | Me | 2-Br-4-CHF$_2$O—Ph |
| II-337 | Me | Me | Me | 2-Br-5-CHF$_2$O—Ph |
| II-338 | Me | Et | Me | 2-Br-5-CHF$_2$O—Ph |
| II-339 | Me | Me | Me | 2-Br-6-CHF$_2$O—Ph |
| II-340 | Me | Et | Me | 2-Br-6-CHF$_2$O—Ph |
| II-341 | Me | Me | Me | 2-Br-3-CD$_3$O—Ph |
| II-342 | Me | Et | Me | 2-Br-3-CD$_3$O—Ph |
| II-343 | Me | Me | Me | 2-Br-4-CD$_3$O—Ph |
| II-344 | Me | Et | Me | 2-Br-4-CD$_3$O—Ph |
| II-345 | Me | Me | Me | 2-Br-5-CD$_3$O—Ph |
| II-346 | Me | Et | Me | 2-Br-5-CD$_3$O—Ph |
| II-347 | Me | Me | Me | 2-Br-6-CD$_3$O—Ph |
| II-348 | Me | Et | Me | 2-Br-6-CD$_3$O—Ph |
| II-349 | Me | Me | Me | 2-Br-3-NC—Ph |
| II-350 | Me | Et | Me | 2-Br-3-NC—Ph |
| II-351 | Me | Me | Me | 2-Br-4-NC—Ph |
| II-352 | Me | Et | Me | 2-Br-4-NC—Ph |
| II-353 | Me | Me | Me | 2-Br-5-NC—Ph |
| II-354 | Me | Et | Me | 2-Br-5-NC—Ph |
| II-355 | Me | Me | Me | 2-Br-6-NC—Ph |
| II-356 | Me | Et | Me | 2-Br-6-NC—Ph |
| II-357 | Me | Me | Me | 2-Me-3-F—Ph |
| II-358 | Me | Et | Me | 2-Me-3-F—Ph |
| II-359 | Me | Me | Me | 2-Me-4-F—Ph |
| II-360 | Me | Et | Me | 2-Me-4-F—Ph |
| II-361 | Me | Me | Me | 2-Me-5-F—Ph |
| II-362 | Me | Et | Me | 2-Me-5-F—Ph |
| II-363 | Me | Me | Me | 2-Me-3-Cl—Ph |
| II-364 | Me | Et | Me | 2-Me-3-Cl—Ph |
| II-365 | Me | Me | Me | 2-Me-4-Cl—Ph |
| II-366 | Me | Et | Me | 2-Me-4-Cl—Ph |
| II-367 | Me | Me | Me | 2-Me-5-Cl—Ph |
| II-368 | Me | Et | Me | 2-Me-5-Cl—Ph |
| II-369 | Me | Me | Me | 2-Me-3-Br—Ph |
| II-370 | Me | Et | Me | 2-Me-3-Br—Ph |
| II-371 | Me | Me | Me | 2-Me-4-Br—Ph |
| II-372 | Me | Et | Me | 2-Me-4-Br—Ph |
| II-373 | Me | Me | Me | 2-Me-5-Br—Ph |
| II-374 | Me | Et | Me | 2-Me-5-Br—Ph |
| II-375 | Me | Me | Me | 2,3-diMe—Ph |
| II-376 | Me | Et | Me | 2,3-diMe—Ph |

TABLE 4-continued

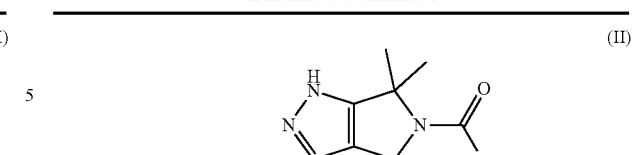

(II)

| Comp. No. | R¹ | R² | R³ | A |
|---|---|---|---|---|
| II-377 | Me | Me | Me | 2,4-diMe—Ph |
| II-378 | Me | Et | Me | 2,4-diMe—Ph |
| II-379 | Me | Me | Me | 2,5-diMe—Ph |
| II-380 | Me | Et | Me | 2,5-diMe—Ph |
| II-381 | Me | Me | Me | 2,6-diMe—Ph |
| II-382 | Me | Et | Me | 2,6-diMe—Ph |
| II-383 | Me | Me | Me | 2-Me-3-Et—Ph |
| II-384 | Me | Et | Me | 2-Me-3-Et—Ph |
| II-385 | Me | Me | Me | 2-Me-4-Et—Ph |
| II-386 | Me | Et | Me | 2-Me-4-Et—Ph |
| II-387 | Me | Me | Me | 2-Me-5-Et—Ph |
| II-388 | Me | Et | Me | 2-Me-5-Et—Ph |
| II-389 | Me | Me | Me | 2-Me-6-Et—Ph |
| II-390 | Me | Et | Me | 2-Me-6-Et—Ph |
| II-391 | Me | Me | Me | 2-Me-3-cPr—Ph |
| II-392 | Me | Et | Me | 2-Me-3-cPr—Ph |
| II-393 | Me | Me | Me | 2-Me-4-cPr—Ph |
| II-394 | Me | Et | Me | 2-Me-4-cPr—Ph |
| II-395 | Me | Me | Me | 2-Me-5-cPr—Ph |
| II-396 | Me | Et | Me | 2-Me-5-cPr—Ph |
| II-397 | Me | Me | Me | 2-Me-6-cPr—Ph |
| II-398 | Me | Et | Me | 2-Me-6-cPr—Ph |
| II-399 | Me | Me | Me | 2-Me-3-CF$_3$—Ph |
| II-400 | Me | Et | Me | 2-Me-3-CF$_3$—Ph |

TABLE 5

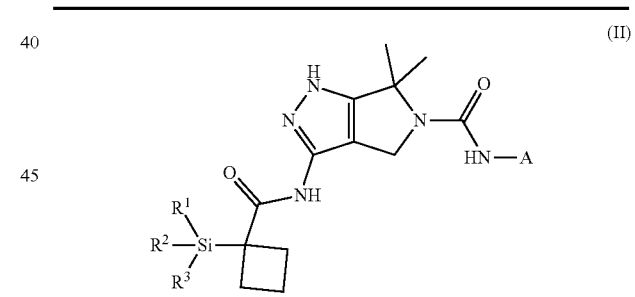

(II)

| Comp. No. | R¹ | R² | R³ | A |
|---|---|---|---|---|
| II-401 | Me | Me | Me | 2-Me-4-CF$_3$—Ph |
| II-402 | Me | Et | Me | 2-Me-4-CF$_3$—Ph |
| II-403 | Me | Me | Me | 2-Me-5-CF$_3$—Ph |
| II-404 | Me | Et | Me | 2-Me-5-CF$_3$—Ph |
| II-405 | Me | Me | Me | 2-Me-6-CF$_3$—Ph |
| II-406 | Me | Et | Me | 2-Me-6-CF$_3$—Ph |
| II-407 | Me | Me | Me | 2-Me-3-MeO—Ph |
| II-408 | Me | Et | Me | 2-Me-3-MeO—Ph |
| II-409 | Me | Me | Me | 2-Me-4-MeO—Ph |
| II-410 | Me | Et | Me | 2-Me-4-MeO—Ph |
| II-411 | Me | Me | Me | 2-Me-5-MeO—Ph |
| II-412 | Me | Et | Me | 2-Me-5-MeO—Ph |
| II-413 | Me | Me | Me | 2-Me-6-MeO—Ph |
| II-414 | Me | Et | Me | 2-Me-6-MeO—Ph |
| II-415 | Me | Me | Me | 2-Me-3-CHF$_2$O—Ph |
| II-416 | Me | Et | Me | 2-Me-3-CHF$_2$O—Ph |
| II-417 | Me | Me | Me | 2-Me-4-CHF$_2$O—Ph |
| II-418 | Me | Et | Me | 2-Me-4-CHF$_2$O—Ph |

TABLE 5-continued

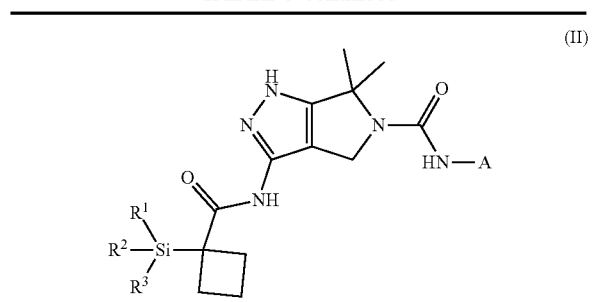

(II)

| Comp. No. | R¹ | R² | R³ | A |
|---|---|---|---|---|
| II-419 | Me | Me | Me | 2-Me-5-CHF$_2$O—Ph |
| II-420 | Me | Et | Me | 2-Me-5-CHF$_2$O—Ph |
| II-421 | Me | Me | Me | 2-Me-6-CHF$_2$O—Ph |
| II-422 | Me | Et | Me | 2-Me-6-CHF$_2$O—Ph |
| II-423 | Me | Me | Me | 2-Me-3-CD$_3$O—Ph |
| II-424 | Me | Et | Me | 2-Me-3-CD$_3$O—Ph |
| II-425 | Me | Me | Me | 2-Me-4-CD$_3$O—Ph |
| II-426 | Me | Et | Me | 2-Me-4-CD$_3$O—Ph |
| II-427 | Me | Me | Me | 2-Me-5-CD$_3$O—Ph |
| II-428 | Me | Et | Me | 2-Me-5-CD$_3$O—Ph |
| II-429 | Me | Me | Me | 2-Me-6-CD$_3$O—Ph |
| II-430 | Me | Et | Me | 2-Me-6-CD$_3$O—Ph |
| II-431 | Me | Me | Me | 2-Me-3-NC—Ph |
| II-432 | Me | Et | Me | 2-Me-3-NC—Ph |
| II-433 | Me | Me | Me | 2-Me-4-NC—Ph |
| II-434 | Me | Et | Me | 2-Me-4-NC—Ph |
| II-435 | Me | Me | Me | 2-Me-5-NC—Ph |
| II-436 | Me | Et | Me | 2-Me-5-NC—Ph |
| II-437 | Me | Me | Me | 2-Me-6-NC—Ph |
| II-438 | Me | Et | Me | 2-Me-6-NC—Ph |
| II-439 | Me | Me | Me | 2-Et-3-F—Ph |
| II-440 | Me | Et | Me | 2-Et-3-F—Ph |
| II-441 | Me | Me | Me | 2-Et-4-F—Ph |
| II-442 | Me | Et | Me | 2-Et-4-F—Ph |
| II-443 | Me | Me | Me | 2-Et-5-F—Ph |
| II-444 | Me | Et | Me | 2-Et-5-F—Ph |
| II-445 | Me | Me | Me | 2-Et-3-Cl—Ph |
| II-446 | Me | Et | Me | 2-Et-3-Cl—Ph |
| II-447 | Me | Me | Me | 2-Et-4-Cl—Ph |
| II-448 | Me | Et | Me | 2-Et-4-Cl—Ph |
| II-449 | Me | Me | Me | 2-Et-5-Cl—Ph |
| II-450 | Me | Et | Me | 2-Et-5-Cl—Ph |
| II-451 | Me | Me | Me | 2-Et-3-Br—Ph |
| II-452 | Me | Et | Me | 2-Et-3-Br—Ph |
| II-453 | Me | Me | Me | 2-Et-4-Br—Ph |
| II-454 | Me | Et | Me | 2-Et-4-Br—Ph |
| II-455 | Me | Me | Me | 2-Et-5-Br—Ph |
| II-456 | Me | Et | Me | 2-Et-5-Br—Ph |
| II-457 | Me | Me | Me | 2-Et-3-Me—Ph |
| II-458 | Me | Et | Me | 2-Et-3-Me—Ph |
| II-459 | Me | Me | Me | 2-Et-4-Me—Ph |
| II-460 | Me | Et | Me | 2-Et-4-Me—Ph |
| II-461 | Me | Me | Me | 2-Et-5-Me—Ph |
| II-462 | Me | Et | Me | 2-Et-5-Me—Ph |
| II-463 | Me | Me | Me | 2,3-diEt—Ph |
| II-464 | Me | Et | Me | 2,3-diEt—Ph |
| II-465 | Me | Me | Me | 2,4-diEt—Ph |
| II-466 | Me | Et | Me | 2,4-diEt—Ph |
| II-467 | Me | Me | Me | 2,5-diEt—Ph |
| II-468 | Me | Et | Me | 2,5-diEt—Ph |
| II-469 | Me | Me | Me | 2,6-diEt—Ph |
| II-470 | Me | Et | Me | 2,6-diEt—Ph |
| II-471 | Me | Me | Me | 2-Et-3-cPr—Ph |
| II-472 | Me | Et | Me | 2-Et-3-cPr—Ph |
| II-473 | Me | Me | Me | 2-Et-4-cPr—Ph |
| II-474 | Me | Et | Me | 2-Et-4-cPr—Ph |
| II-475 | Me | Me | Me | 2-Et-5-cPr—Ph |
| II-476 | Me | Et | Me | 2-Et-5-cPr—Ph |
| II-477 | Me | Me | Me | 2-Et-6-cPr—Ph |
| II-478 | Me | Et | Me | 2-Et-6-cPr—Ph |
| II-479 | Me | Me | Me | 2-Et-3-CF$_3$—Ph |
| II-480 | Me | Et | Me | 2-Et-3-CF$_3$—Ph |
| II-481 | Me | Me | Me | 2-Et-4-CF$_3$—Ph |
| II-482 | Me | Et | Me | 2-Et-4-CF$_3$—Ph |
| II-483 | Me | Me | Me | 2-Et-5-CF$_3$—Ph |
| II-484 | Me | Et | Me | 2-Et-5-CF$_3$—Ph |
| II-485 | Me | Me | Me | 2-Et-6-CF$_3$—Ph |
| II-486 | Me | Et | Me | 2-Et-6-CF$_3$—Ph |
| II-487 | Me | Me | Me | 2-Et-3-MeO—Ph |
| II-488 | Me | Et | Me | 2-Et-3-MeO—Ph |
| II-489 | Me | Me | Me | 2-Et-4-MeO—Ph |
| II-490 | Me | Et | Me | 2-Et-4-MeO—Ph |
| II-491 | Me | Me | Me | 2-Et-5-MeO—Ph |
| II-492 | Me | Et | Me | 2-Et-5-MeO—Ph |
| II-493 | Me | Me | Me | 2-Et-6-MeO—Ph |
| II-494 | Me | Et | Me | 2-Et-6-MeO—Ph |
| II-495 | Me | Me | Me | 2-Et-3-CHF$_2$O—Ph |
| II-496 | Me | Et | Me | 2-Et-3-CHF$_2$O—Ph |
| II-497 | Me | Me | Me | 2-Et-4-CHF$_2$O—Ph |
| II-498 | Me | Et | Me | 2-Et-4-CHF$_2$O—Ph |
| II-499 | Me | Me | Me | 2-Et-5-CHF$_2$O—Ph |
| II-500 | Me | Et | Me | 2-Et-5-CHF$_2$O—Ph |

TABLE 6

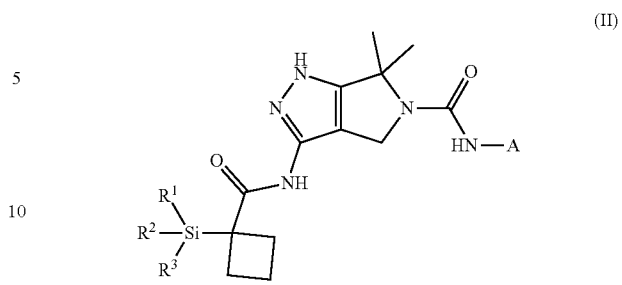

(II)

| Comp. No. | R¹ | R² | R³ | A |
|---|---|---|---|---|
| II-501 | Me | Me | Me | 2-Et-6-CHF$_2$O—Ph |
| II-502 | Me | Et | Me | 2-Et-6-CHF$_2$O—Ph |
| II-503 | Me | Me | Me | 2-Et-3-CD$_3$O—Ph |
| II-504 | Me | Et | Me | 2-Et-3-CD$_3$O—Ph |
| II-505 | Me | Me | Me | 2-Et-4-CD$_3$O—Ph |
| II-506 | Me | Et | Me | 2-Et-4-CD$_3$O—Ph |
| II-507 | Me | Me | Me | 2-Et-5-CD$_3$O—Ph |
| II-508 | Me | Et | Me | 2-Et-5-CD$_3$O—Ph |
| II-509 | Me | Me | Me | 2-Et-6-CD$_3$O—Ph |
| II-510 | Me | Et | Me | 2-Et-6-CD$_3$O—Ph |
| II-511 | Me | Me | Me | 2-Et-3-NC—Ph |
| II-512 | Me | Et | Me | 2-Et-3-NC—Ph |
| II-513 | Me | Me | Me | 2-Et-4-NC—Ph |
| II-514 | Me | Et | Me | 2-Et-4-NC—Ph |
| II-515 | Me | Me | Me | 2-Et-5-NC—Ph |
| II-516 | Me | Et | Me | 2-Et-5-NC—Ph |
| II-517 | Me | Me | Me | 2-Et-6-NC—Ph |
| II-518 | Me | Et | Me | 2-Et-6-NC—Ph |
| II-519 | Me | Me | Me | 2-MeO-3-F—Ph |
| II-520 | Me | Et | Me | 2-MeO-3-F—Ph |
| II-521 | Me | Me | Me | 2-MeO-4-F—Ph |
| II-522 | Me | Et | Me | 2-MeO-4-F—Ph |
| II-523 | Me | Me | Me | 2-MeO-5-F—Ph |
| II-524 | Me | Et | Me | 2-MeO-5-F—Ph |

TABLE 6-continued

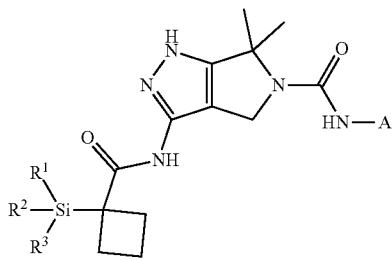
(II)

| Comp. No. | R¹ | R² | R³ | A |
|---|---|---|---|---|
| II-525 | Me | Me | Me | 2-MeO-3-Cl—Ph |
| II-526 | Me | Et | Me | 2-MeO-3-Cl—Ph |
| II-527 | Me | Me | Me | 2-MeO-4-Cl—Ph |
| II-528 | Me | Et | Me | 2-MeO-4-Cl—Ph |
| II-529 | Me | Me | Me | 2-MeO-5-Cl—Ph |
| II-530 | Me | Et | Me | 2-MeO-5-Cl—Ph |
| II-531 | Me | Me | Me | 2-MeO-3-Br—Ph |
| II-532 | Me | Et | Me | 2-MeO-3-Br—Ph |
| II-533 | Me | Me | Me | 2-MeO-4-Br—Ph |
| II-534 | Me | Et | Me | 2-MeO-4-Br—Ph |
| II-535 | Me | Me | Me | 2-MeO-5-Br—Ph |
| II-536 | Me | Et | Me | 2-MeO-5-Br—Ph |
| II-537 | Me | Me | Me | 2-MeO-3-Me—Ph |
| II-538 | Me | Et | Me | 2-MeO-3-Me—Ph |
| II-539 | Me | Me | Me | 2-MeO-4-Me—Ph |
| II-540 | Me | Et | Me | 2-MeO-4-Me—Ph |
| II-541 | Me | Me | Me | 2-MeO-5-Me—Ph |
| II-542 | Me | Et | Me | 2-MeO-5-Me—Ph |
| II-543 | Me | Me | Me | 2-MeO-3-Et—Ph |
| II-544 | Me | Et | Me | 2-MeO-3-Et—Ph |
| II-545 | Me | Me | Me | 2-MeO-4-Et—Ph |
| II-546 | Me | Et | Me | 2-MeO-4-Et—Ph |
| II-547 | Me | Me | Me | 2-MeO-5-Et—Ph |
| II-548 | Me | Et | Me | 2-MeO-5-Et—Ph |
| II-549 | Me | Me | Me | 2-MeO-3-cPr—Ph |
| II-550 | Me | Et | Me | 2-MeO-3-cPr—Ph |
| II-551 | Me | Me | Me | 2-MeO-4-cPr—Ph |
| II-552 | Me | Et | Me | 2-MeO-4-cPr—Ph |
| II-553 | Me | Me | Me | 2-MeO-5-cPr—Ph |
| II-554 | Me | Et | Me | 2-MeO-5-cPr—Ph |
| II-555 | Me | Me | Me | 2-MeO-6-cPr—Ph |
| II-556 | Me | Et | Me | 2-MeO-6-cPr—Ph |
| II-557 | Me | Me | Me | 2-MeO-3-CF₃—Ph |
| II-558 | Me | Et | Me | 2-MeO-3-CF₃—Ph |
| II-559 | Me | Me | Me | 2-MeO-4-CF₃—Ph |
| II-560 | Me | Et | Me | 2-MeO-4-CF₃—Ph |
| II-561 | Me | Me | Me | 2-MeO-5-CF₃—Ph |
| II-562 | Me | Et | Me | 2-MeO-5-CF₃—Ph |
| II-563 | Me | Me | Me | 2-MeO-6-CF₃—Ph |
| II-564 | Me | Et | Me | 2-MeO-6-CF₃—Ph |
| II-565 | Me | Me | Me | 2,3-diMeO—Ph |
| II-566 | Me | Et | Me | 2,3-diMeO—Ph |
| II-567 | Me | Me | Me | 2,4-diMeO—Ph |
| II-568 | Me | Et | Me | 2,4-diMeO—Ph |
| II-569 | Me | Me | Me | 2,5-diMeO—Ph |
| II-570 | Me | Et | Me | 2,5-diMeO—Ph |
| II-571 | Me | Me | Me | 2,6-diMeO—Ph |
| II-572 | Me | Et | Me | 2,6-diMeO—Ph |
| II-573 | Me | Me | Me | 2-MeO-3-CHF₂O—Ph |
| II-574 | Me | Et | Me | 2-MeO-3-CHF₂O—Ph |
| II-575 | Me | Me | Me | 2-MeO-4-CHF₂O—Ph |
| II-576 | Me | Et | Me | 2-MeO-4-CHF₂O—Ph |
| II-577 | Me | Me | Me | 2-MeO-5-CHF₂O—Ph |
| II-578 | Me | Et | Me | 2-MeO-5-CHF₂O—Ph |
| II-579 | Me | Me | Me | 2-MeO-6-CHF₂O—Ph |
| II-580 | Me | Et | Me | 2-MeO-6-CHF₂O—Ph |
| II-581 | Me | Me | Me | 2-MeO-3-CD₃O—Ph |
| II-582 | Me | Et | Me | 2-MeO-3-CD₃O—Ph |
| II-583 | Me | Me | Me | 2-MeO-4-CD₃O—Ph |
| II-584 | Me | Et | Me | 2-MeO-4-CD₃O—Ph |
| II-585 | Me | Me | Me | 2-MeO-5-CD₃O—Ph |
| II-586 | Me | Et | Me | 2-MeO-5-CD₃O—Ph |
| II-587 | Me | Me | Me | 2-MeO-6-CD₃O—Ph |
| II-588 | Me | Et | Me | 2-MeO-6-CD₃O—Ph |

TABLE 6-continued

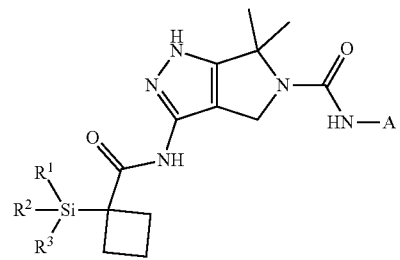
(II)

| Comp. No. | R¹ | R² | R³ | A |
|---|---|---|---|---|
| II-589 | Me | Me | Me | 2-MeO-3-NC—Ph |
| II-590 | Me | Et | Me | 2-MeO-3-NC—Ph |
| II-591 | Me | Me | Me | 2-MeO-4-NC—Ph |
| II-592 | Me | Et | Me | 2-MeO-4-NC—Ph |
| II-593 | Me | Me | Me | 2-MeO-5-NC—Ph |
| II-594 | Me | Et | Me | 2-MeO-5-NC—Ph |
| II-595 | Me | Me | Me | 2-MeO-6-NC—Ph |
| II-596 | Me | Et | Me | 2-MeO-6-NC—Ph |
| II-597 | Me | Me | Me | 2,3,6-triF—Ph |
| II-598 | Me | Et | Me | 2,3,6-triF—Ph |
| II-599 | Me | Me | Me | 2,4,6-triF—Ph |
| II-600 | Me | Et | Me | 2,4,6-triF—Ph |

TABLE 7

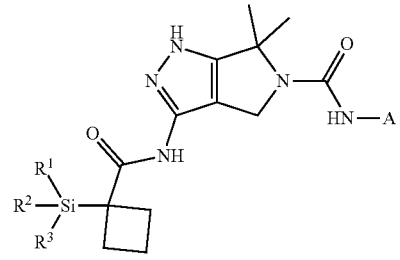
(II)

| Comp. No. | R¹ | R² | R³ | A |
|---|---|---|---|---|
| II-601 | Me | Me | Me | 2,6-diF-3-Cl—Ph |
| II-602 | Me | Et | Me | 2,6-diF-3-Cl—Ph |
| II-603 | Me | Me | Me | 2,6-diF-4-Cl—Ph |
| II-604 | Me | Et | Me | 2,6-diF-4-Cl—Ph |
| II-605 | Me | Me | Me | 2,6-diF-3-Br—Ph |
| II-606 | Me | Et | Me | 2,6-diF-3-Br—Ph |
| II-607 | Me | Me | Me | 2,6-diF-4-Br—Ph |
| II-608 | Me | Et | Me | 2,6-diF-4-Br—Ph |
| II-609 | Me | Me | Me | 2,6-diF-3-Me—Ph |
| II-610 | Me | Et | Me | 2,6-diF-3-Me—Ph |
| II-611 | Me | Me | Me | 2,6-diF-4-Me—Ph |
| II-612 | Me | Et | Me | 2,6-diF-4-Me—Ph |
| II-613 | Me | Me | Me | 2,6-diF-3-MeO—Ph |
| II-614 | Me | Et | Me | 2,6-diF-3-MeO—Ph |
| II-615 | Me | Me | Me | 2,6-diF-4-MeO—Ph |
| II-616 | Me | Et | Me | 2,6-diF-4-MeO—Ph |
| II-617 | Me | Me | Me | 2,3-diF-6-Cl—Ph |
| II-618 | Me | Et | Me | 2,3-diF-6-Cl—Ph |
| II-619 | Me | Me | Me | 2,4-diF-6-Cl—Ph |
| II-620 | Me | Et | Me | 2,4-diF-6-Cl—Ph |
| II-621 | Me | Me | Me | 2-F-3,6-diCl—Ph |
| II-622 | Me | Et | Me | 2-F-3,6-diCl—Ph |
| II-623 | Me | Me | Me | 2-F-4,6-diCl—Ph |
| II-624 | Me | Et | Me | 2-F-4,6-diCl—Ph |
| II-625 | Me | Me | Me | 2-F-3-Br-6-Cl—Ph |
| II-626 | Me | Et | Me | 2-F-3-Br-6-Cl—Ph |
| II-627 | Me | Me | Me | 2-F-4-Br-6-Cl—Ph |
| II-628 | Me | Et | Me | 2-F-4-Br-6-Cl—Ph |
| II-629 | Me | Me | Me | 2-F-3-Me-6-Cl—Ph |
| II-630 | Me | Et | Me | 2-F-3-Me-6-Cl—Ph |

TABLE 7-continued

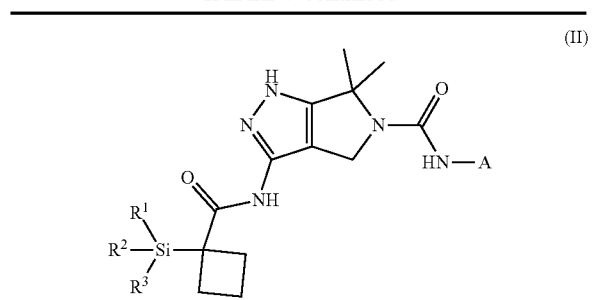

(II)

| Comp. No. | R¹ | R² | R³ | A |
|---|---|---|---|---|
| II-631 | Me | Me | Me | 2-F-4-Me-6-Cl—Ph |
| II-632 | Me | Et | Me | 2-F-4-Me-6-Cl—Ph |
| II-633 | Me | Me | Me | 2-F-3-MeO-6-Cl—Ph |
| II-634 | Me | Et | Me | 2-F-3-MeO-6-Cl—Ph |
| II-635 | Me | Me | Me | 2-F-4-MeO-6-Cl—Ph |
| II-636 | Me | Et | Me | 2-F-4-MeO-6-Cl—Ph |
| II-637 | Me | Me | Me | 2,3-diF-6-Br—Ph |
| II-638 | Me | Et | Me | 2,3-diF-6-Br—Ph |
| II-639 | Me | Me | Me | 2,4-diF-6-Br—Ph |
| II-640 | Me | Et | Me | 2,4-diF-6-Br—Ph |
| II-641 | Me | Me | Me | 2-F-3-Cl-6-Br—Ph |
| II-642 | Me | Et | Me | 2-F-3-Cl-6-Br—Ph |
| II-643 | Me | Me | Me | 2-F-4-Cl-6-Br—Ph |
| II-644 | Me | Et | Me | 2-F-4-Cl-6-Br—Ph |
| II-645 | Me | Me | Me | 2-F-3,6-diBr—Ph |
| II-646 | Me | Et | Me | 2-F-3,6-diBr—Ph |
| II-647 | Me | Me | Me | 2-F-4,6-diBr—Ph |
| II-648 | Me | Et | Me | 2-F-4,6-diBr—Ph |
| II-649 | Me | Me | Me | 2-F-3-Me-6-Br—Ph |
| II-650 | Me | Et | Me | 2-F-3-Me-6-Br—Ph |
| II-651 | Me | Me | Me | 2-F-4-Me-6-Br—Ph |
| II-652 | Me | Et | Me | 2-F-4-Me-6-Br—Ph |
| II-653 | Me | Me | Me | 2-F-3-MeO-6-Br—Ph |
| II-654 | Me | Et | Me | 2-F-3-MeO-6-Br—Ph |
| II-655 | Me | Me | Me | 2-F-4-MeO-6-Br—Ph |
| II-656 | Me | Et | Me | 2-F-4-MeO-6-Br—Ph |
| II-657 | Me | Me | Me | 2,3-diF-6-Me—Ph |
| II-658 | Me | Et | Me | 2,3-diF-6-Me—Ph |
| II-659 | Me | Me | Me | 2,4-diF-6-Me—Ph |
| II-660 | Me | Et | Me | 2,4-diF-6-Me—Ph |
| II-661 | Me | Me | Me | 2-F-3-Cl-6-Me—Ph |
| II-662 | Me | Et | Me | 2-F-3-Cl-6-Me—Ph |
| II-663 | Me | Me | Me | 2-F-4-Cl-6-Me—Ph |
| II-664 | Me | Et | Me | 2-F-4-Cl-6-Me—Ph |
| II-665 | Me | Me | Me | 2-F-3-Br-6-Me—Ph |
| II-666 | Me | Et | Me | 2-F-3-Br-6-Me—Ph |
| II-667 | Me | Me | Me | 2-F-4-Br-6-Me—Ph |
| II-668 | Me | Et | Me | 2-F-4-Br-6-Me—Ph |
| II-669 | Me | Me | Me | 2-F-3,6-diMe—Ph |
| II-670 | Me | Et | Me | 2-F-3,6-diMe—Ph |
| II-671 | Me | Me | Me | 2-F-4,6-diMe—Ph |
| II-672 | Me | Et | Me | 2-F-4,6-diMe—Ph |
| II-673 | Me | Me | Me | 2-F-3-MeO-6-Me—Ph |
| II-674 | Me | Et | Me | 2-F-3-MeO-6-Me—Ph |
| II-675 | Me | Me | Me | 2-F-4-MeO-6-Me—Ph |
| II-676 | Me | Et | Me | 2-F-4-MeO-6-Me—Ph |
| II-677 | Me | Me | Me | 2,3-diF-6-MeO—Ph |
| II-678 | Me | Et | Me | 2,3-diF-6-MeO—Ph |
| II-679 | Me | Me | Me | 2,4-diF-6-MeO—Ph |
| II-680 | Me | Et | Me | 2,4-diF-6-MeO—Ph |
| II-681 | Me | Me | Me | 2-F-3-Cl-6-MeO—Ph |
| II-682 | Me | Et | Me | 2-F-3-Cl-6-MeO—Ph |
| II-683 | Me | Me | Me | 2-F-4-Cl-6-MeO—Ph |
| II-684 | Me | Et | Me | 2-F-4-Cl-6-MeO—Ph |
| II-685 | Me | Me | Me | 2-F-3-Br-6-MeO—Ph |
| II-686 | Me | Et | Me | 2-F-3-Br-6-MeO—Ph |
| II-687 | Me | Me | Me | 2-F-4-Br-6-MeO—Ph |
| II-688 | Me | Et | Me | 2-F-4-Br-6-MeO—Ph |
| II-689 | Me | Me | Me | 2-F-3-Me-6-MeO—Ph |
| II-690 | Me | Et | Me | 2-F-3-Me-6-MeO—Ph |
| II-691 | Me | Me | Me | 2-F-4-Me-6-MeO—Ph |
| II-692 | Me | Et | Me | 2-F-4-Me-6-MeO—Ph |
| II-693 | Me | Me | Me | 2-F-3,6-diMeO—Ph |
| II-694 | Me | Me | Me | 2-F-3,6-diMeO—Ph |

TABLE 7-continued

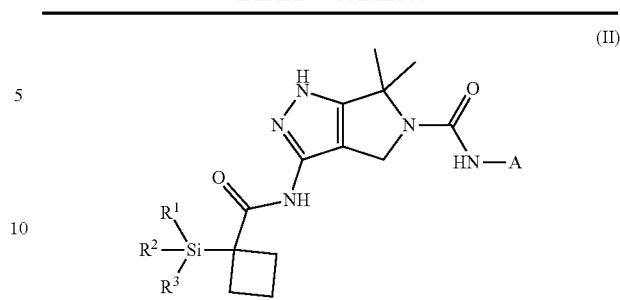

(II)

| Comp. No. | R¹ | R² | R³ | A |
|---|---|---|---|---|
| II-695 | Me | Me | Me | 2-F-4,6-diMeO—Ph |
| II-696 | Me | Et | Me | 2-F-4,6-diMeO—Ph |
| II-697 | Me | Me | Me | 2-Cl-3,6-diF—Ph |
| II-698 | Me | Et | Me | 2-Cl-3,6-diF—Ph |
| II-699 | Me | Me | Me | 2,3-diCl-6-F—Ph |
| II-700 | Me | Et | Me | 2,3-diCl-6-F—Ph |

TABLE 8

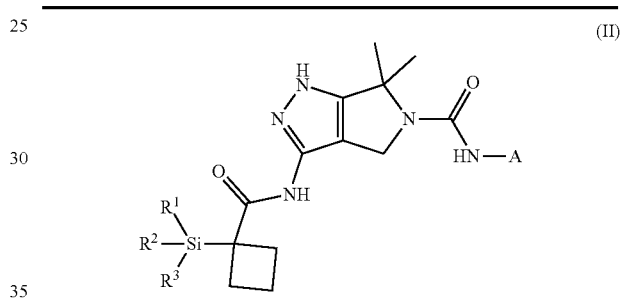

(II)

| Comp. No. | R¹ | R² | R³ | A |
|---|---|---|---|---|
| II-701 | Me | Me | Me | 2-Cl-3-Br-6-F—Ph |
| II-702 | Me | Et | Me | 2-Cl-3-Br-6-F—Ph |
| II-703 | Me | Me | Me | 2-Cl-3-Me-6-F—Ph |
| II-704 | Me | Et | Me | 2-Cl-3-Me-6-F—Ph |
| II-705 | Me | Me | Me | 2-Cl-3-MeO-6-F—Ph |
| II-706 | Me | Et | Me | 2-Cl-3-MeO-6-F—Ph |
| II-707 | Me | Me | Me | 2,6-diCl-3-F—Ph |
| II-708 | Me | Et | Me | 2,6-diCl-3-F—Ph |
| II-709 | Me | Me | Me | 2,6-diCl-4-F—Ph |
| II-710 | Me | Et | Me | 2,6-diCl-4-F—Ph |
| II-711 | Me | Me | Me | 2,3,6-triCl—Ph |
| II-712 | Me | Et | Me | 2,3,6-triCl—Ph |
| II-713 | Me | Me | Me | 2,4,6-triCl—Ph |
| II-714 | Me | Et | Me | 2,4,6-triCl—Ph |
| II-715 | Me | Me | Me | 2,6-diCl-3-Br—Ph |
| II-716 | Me | Et | Me | 2,6-diCl-3-Br—Ph |
| II-717 | Me | Me | Me | 2,6-diCl-4-Br—Ph |
| II-718 | Me | Et | Me | 2,6-diCl-4-Br—Ph |
| II-719 | Me | Me | Me | 2,6-diCl-3-Me—Ph |
| II-720 | Me | Et | Me | 2,6-diCl-3-Me—Ph |
| II-721 | Me | Me | Me | 2,6-diCl-4-Me—Ph |
| II-722 | Me | Et | Me | 2,6-diCl-4-Me—Ph |
| II-723 | Me | Me | Me | 2,6-diCl-3-MeO—Ph |
| II-724 | Me | Et | Me | 2,6-diCl-3-MeO—Ph |
| II-725 | Me | Me | Me | 2,6-diCl-4-MeO—Ph |
| II-726 | Me | Et | Me | 2,6-diCl-4-MeO—Ph |
| II-727 | Me | Me | Me | 2-Cl-3-F-6-Br—Ph |
| II-728 | Me | Et | Me | 2-Cl-3-F-6-Br—Ph |
| II-729 | Me | Me | Me | 2-Cl-4-F-6-Br—Ph |
| II-730 | Me | Et | Me | 2-Cl-4-F-6-Br—Ph |
| II-731 | Me | Me | Me | 2,3-diCl-6-Br—Ph |
| II-732 | Me | Et | Me | 2,3-diCl-6-Br—Ph |
| II-733 | Me | Me | Me | 2,4-diCl-6-Br—Ph |
| II-734 | Me | Et | Me | 2,4-diCl-6-Br—Ph |
| II-735 | Me | Me | Me | 2-Cl-3,6-diBr—Ph |
| II-736 | Me | Et | Me | 2-Cl-3,6-diBr—Ph |

TABLE 8-continued (II)

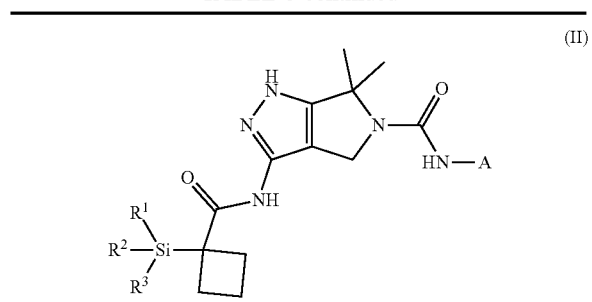

| Comp. No. | R¹ | R² | R³ | A |
|---|---|---|---|---|
| II-737 | Me | Me | Me | 2-Cl-4,6-diBr—Ph |
| II-738 | Me | Et | Me | 2-Cl-4,6-diBr—Ph |
| II-739 | Me | Me | Me | 2-Cl-3-Me-6-Br—Ph |
| II-740 | Me | Et | Me | 2-Cl-3-Me-6-Br—Ph |
| II-741 | Me | Me | Me | 2-Cl-4-Me-6-Br—Ph |
| II-742 | Me | Et | Me | 2-Cl-4-Me-6-Br—Ph |
| II-743 | Me | Me | Me | 2-Cl-3-MeO-6-Br—Ph |
| II-744 | Me | Et | Me | 2-Cl-3-MeO-6-Br—Ph |
| II-745 | Me | Me | Me | 2-Cl-4-MeO-6-Br—Ph |
| II-746 | Me | Et | Me | 2-Cl-4-MeO-6-Br—Ph |
| II-747 | Me | Me | Me | 2-Cl-3-F-6-Me—Ph |
| II-748 | Me | Et | Me | 2-Cl-3-F-6-Me—Ph |
| II-749 | Me | Me | Me | 2-Cl-4-F-6-Me—Ph |
| II-750 | Me | Et | Me | 2-Cl-4-F-6-Me—Ph |
| II-751 | Me | Me | Me | 2,3-diCl-6-Me—Ph |
| II-752 | Me | Et | Me | 2,3-diCl-6-Me—Ph |
| II-753 | Me | Me | Me | 2,4-diCl-6-Me—Ph |
| II-754 | Me | Et | Me | 2,4-diCl-6-Me—Ph |
| II-755 | Me | Me | Me | 2-Cl-3-Br-6-Me—Ph |
| II-756 | Me | Et | Me | 2-Cl-3-Br-6-Me—Ph |
| II-757 | Me | Me | Me | 2-Cl-4-Br-6-Me—Ph |
| II-758 | Me | Et | Me | 2-Cl-4-Br-6-Me—Ph |
| II-759 | Me | Me | Me | 2-Cl-3,6-diMe—Ph |
| II-760 | Me | Et | Me | 2-Cl-3,6-diMe—Ph |
| II-761 | Me | Me | Me | 2-Cl-4,6-diMe—Ph |
| II-762 | Me | Et | Me | 2-Cl-4,6-diMe—Ph |
| II-763 | Me | Me | Me | 2-Cl-3-MeO-6-Me—Ph |
| II-764 | Me | Et | Me | 2-Cl-3-MeO-6-Me—Ph |
| II-765 | Me | Me | Me | 2-Cl-4-MeO-6-Me—Ph |
| II-766 | Me | Et | Me | 2-Cl-4-MeO-6-Me—Ph |
| II-767 | Me | Me | Me | 2-Cl-3-F-6-MeO—Ph |
| II-768 | Me | Et | Me | 2-Cl-3-F-6-MeO—Ph |
| II-769 | Me | Me | Me | 2-Cl-4-F-6-MeO—Ph |
| II-770 | Me | Et | Me | 2-Cl-4-F-6-MeO—Ph |
| II-771 | Me | Me | Me | 2,3-diCl-6-MeO—Ph |
| II-772 | Me | Et | Me | 2,3-diCl-6-MeO—Ph |
| II-773 | Me | Me | Me | 2,4-diCl-6-MeO—Ph |
| II-774 | Me | Et | Me | 2,4-diCl-6-MeO—Ph |
| II-775 | Me | Me | Me | 2-Cl-3-Br-6-MeO—Ph |
| II-776 | Me | Et | Me | 2-Cl-3-Br-6-MeO—Ph |
| II-777 | Me | Me | Me | 2-Cl-4-Br-6-MeO—Ph |
| II-778 | Me | Et | Me | 2-Cl-4-Br-6-MeO—Ph |
| II-779 | Me | Me | Me | 2-Cl-3-Me-6-MeO—Ph |
| II-780 | Me | Et | Me | 2-Cl-3-Me-6-MeO—Ph |
| II-781 | Me | Me | Me | 2-Cl-4-Me-6-MeO—Ph |
| II-782 | Me | Et | Me | 2-Cl-4-Me-6-MeO—Ph |
| II-783 | Me | Me | Me | 2-Cl-3,6-diMeO—Ph |
| II-784 | Me | Et | Me | 2-Cl-3,6-diMeO—Ph |
| II-785 | Me | Me | Me | 2-Cl-4,6-diMeO—Ph |
| II-786 | Me | Et | Me | 2-Cl-4,6-diMeO—Ph |
| II-787 | Me | Me | Me | 2-Br-3,6-diF—Ph |
| II-788 | Me | Et | Me | 2-Br-3,6-diF—Ph |
| II-789 | Me | Me | Me | 2-Br-3-Cl-6-F—Ph |
| II-790 | Me | Et | Me | 2-Br-3-Cl-6-F—Ph |
| II-791 | Me | Me | Me | 2,3-diBr-6-F—Ph |
| II-792 | Me | Et | Me | 2,3-diBr-6-F—Ph |
| II-793 | Me | Me | Me | 2-Br-3-Me-6-F—Ph |
| II-794 | Me | Et | Me | 2-Br-3-Me-6-F—Ph |
| II-795 | Me | Me | Me | 2-Br-3-MeO-6-F—Ph |
| II-796 | Me | Et | Me | 2-Br-3-MeO-6-F—Ph |
| II-797 | Me | Me | Me | 2-Br-3-F-6-Cl—Ph |
| II-798 | Me | Et | Me | 2-Br-3-F-6-Cl—Ph |

TABLE 8-continued (II)

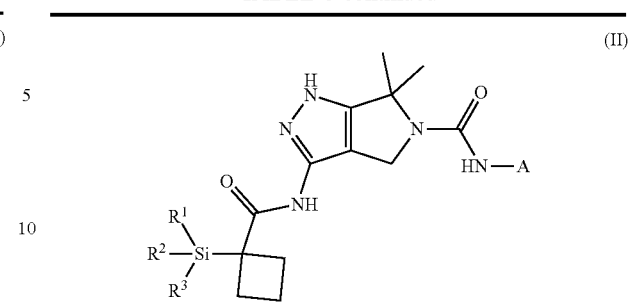

| Comp. No. | R¹ | R² | R³ | A |
|---|---|---|---|---|
| II-799 | Me | Me | Me | 2-Br-3,6-diCl—Ph |
| II-800 | Me | Et | Me | 2-Br-3,6-diCl—Ph |

TABLE 9

(II)

| Comp. No. | R¹ | R² | R³ | A |
|---|---|---|---|---|
| II-801 | Me | Me | Me | 2,3-diBr-6-Cl—Ph |
| II-802 | Me | Et | Me | 2,3-diBr-6-Cl—Ph |
| II-803 | Me | Me | Me | 2-Br-3-Me-6-Cl—Ph |
| II-804 | Me | Et | Me | 2-Br-3-Me-6-Cl—Ph |
| II-805 | Me | Me | Me | 2-Br-3-MeO-6-Cl—Ph |
| II-806 | Me | Et | Me | 2-Br-3-MeO-6-Cl—Ph |
| II-807 | Me | Me | Me | 2,6-diBr-3-F—Ph |
| II-808 | Me | Et | Me | 2,6-diBr-3-F—Ph |
| II-809 | Me | Me | Me | 2,6-diBr-4-F—Ph |
| II-810 | Me | Et | Me | 2,6-diBr-4-F—Ph |
| II-811 | Me | Me | Me | 2,6-diBr-3-Cl—Ph |
| II-812 | Me | Et | Me | 2,6-diBr-3-Cl—Ph |
| II-813 | Me | Me | Me | 2,6-diBr-4-Cl—Ph |
| II-814 | Me | Et | Me | 2,6-diBr-4-Cl—Ph |
| II-815 | Me | Me | Me | 2,3,6-triBr—Ph |
| II-816 | Me | Et | Me | 2,3,6-triBr—Ph |
| II-817 | Me | Me | Me | 2,4,6-triBr—Ph |
| II-818 | Me | Et | Me | 2,4,6-triBr—Ph |
| II-819 | Me | Me | Me | 2,6-diBr-3-Me—Ph |
| II-820 | Me | Et | Me | 2,6-diBr-3-Me—Ph |
| II-821 | Me | Me | Me | 2,6-diBr-4-Me—Ph |
| II-822 | Me | Et | Me | 2,6-diBr-4-Me—Ph |
| II-823 | Me | Me | Me | 2,6-diBr-3-MeO—Ph |
| II-824 | Me | Et | Me | 2,6-diBr-3-MeO—Ph |
| II-825 | Me | Me | Me | 2,6-diBr-4-MeO—Ph |
| II-826 | Me | Et | Me | 2,6-diBr-4-MeO—Ph |
| II-827 | Me | Me | Me | 2-Br-3-F-6-Me—Ph |
| II-828 | Me | Et | Me | 2-Br-3-F-6-Me—Ph |
| II-829 | Me | Me | Me | 2-Br-4-F-6-Me—Ph |
| II-830 | Me | Et | Me | 2-Br-4-F-6-Me—Ph |
| II-831 | Me | Me | Me | 2-Br-3-Cl-6-Me—Ph |
| II-832 | Me | Et | Me | 2-Br-3-Cl-6-Me—Ph |
| II-833 | Me | Me | Me | 2-Br-4-Cl-6-Me—Ph |
| II-834 | Me | Et | Me | 2-Br-4-Cl-6-Me—Ph |
| II-835 | Me | Me | Me | 2,3-diBr-6-Me—Ph |
| II-836 | Me | Et | Me | 2,3-diBr-6-Me—Ph |
| II-837 | Me | Me | Me | 2,4-diBr-6-Me—Ph |
| II-838 | Me | Et | Me | 2,4-diBr-6-Me—Ph |
| II-839 | Me | Me | Me | 2-Br-3,6-diMe—Ph |
| II-840 | Me | Et | Me | 2-Br-3,6-diMe—Ph |

TABLE 9-continued (II)

| Comp. No. | R¹ | R² | R³ | A |
|---|---|---|---|---|
| II-841 | Me | Me | Me | 2-Br-4,6-diMe—Ph |
| II-842 | Me | Et | Me | 2-Br-4,6-diMe—Ph |
| II-843 | Me | Me | Me | 2-Br-3-MeO-6-Me—Ph |
| II-844 | Me | Et | Me | 2-Br-3-MeO-6-Me—Ph |
| II-845 | Me | Me | Me | 2-Br-4-MeO-6-Me—Ph |
| II-846 | Me | Et | Me | 2-Br-4-MeO-6-Me—Ph |
| II-847 | Me | Me | Me | 2-Br-3-F-6-MeO—Ph |
| II-848 | Me | Et | Me | 2-Br-3-F-6-MeO—Ph |
| II-849 | Me | Me | Me | 2-Br-4-F-6-MeO—Ph |
| II-850 | Me | Et | Me | 2-Br-4-F-6-MeO—Ph |
| II-851 | Me | Me | Me | 2-Br-3-Cl-6-MeO—Ph |
| II-852 | Me | Et | Me | 2-Br-3-Cl-6-MeO—Ph |
| II-853 | Me | Me | Me | 2-Br-4-Cl-6-MeO—Ph |
| II-854 | Me | Et | Me | 2-Br-4-Cl-6-MeO—Ph |
| II-855 | Me | Me | Me | 2,3-diBr-6-MeO—Ph |
| II-856 | Me | Et | Me | 2,3-diBr-6-MeO—Ph |
| II-857 | Me | Me | Me | 2,4-diBr-6-MeO—Ph |
| II-858 | Me | Et | Me | 2,4-diBr-6-MeO—Ph |
| II-859 | Me | Me | Me | 2-Br-3-Me-6-MeO—Ph |
| II-860 | Me | Et | Me | 2-Br-3-Me-6-MeO—Ph |
| II-861 | Me | Me | Me | 2-Br-4-Me-6-MeO—Ph |
| II-862 | Me | Et | Me | 2-Br-4-Me-6-MeO—Ph |
| II-863 | Me | Me | Me | 2-Br-3,6-diMeO—Ph |
| II-864 | Me | Et | Me | 2-Br-3,6-diMeO—Ph |
| II-865 | Me | Me | Me | 2-Br-4,6-diMeO—Ph |
| II-866 | Me | Et | Me | 2-Br-4,6-diMeO—Ph |
| II-867 | Me | Me | Me | 2-Me-3,6-diF—Ph |
| II-868 | Me | Et | Me | 2-Me-3,6-diF—Ph |
| II-869 | Me | Me | Me | 2-Me-3-Cl-6-F—Ph |
| II-870 | Me | Et | Me | 2-Me-3-Cl-6-F—Ph |
| II-871 | Me | Me | Me | 2-Me-3-Br-6-F—Ph |
| II-872 | Me | Et | Me | 2-Me-3-Br-6-F—Ph |
| II-873 | Me | Me | Me | 2,3-diMe-6-F—Ph |
| II-874 | Me | Et | Me | 2,3-diMe-6-F—Ph |
| II-875 | Me | Me | Me | 2,4-diMe-6-F—Ph |
| II-876 | Me | Et | Me | 2,4-diMe-6-F—Ph |
| II-877 | Me | Me | Me | 2-Me-3-MeO-6-F—Ph |
| II-878 | Me | Et | Me | 2-Me-3-MeO-6-F—Ph |
| II-879 | Me | Me | Me | 2-Me-4-MeO-6-F—Ph |
| II-880 | Me | Et | Me | 2-Me-4-MeO-6-F—Ph |
| II-881 | Me | Me | Me | 2-Me-3-F-6-Cl—Ph |
| II-882 | Me | Et | Me | 2-Me-3-F-6-Cl—Ph |
| II-883 | Me | Me | Me | 2-Me-3,6-diCl—Ph |
| II-884 | Me | Et | Me | 2-Me-3,6-diCl—Ph |
| II-885 | Me | Me | Me | 2-Me-3-Br-6-Cl—Ph |
| II-886 | Me | Et | Me | 2-Me-3-Br-6-Cl—Ph |
| II-887 | Me | Me | Me | 2,3-diMe-6-Cl—Ph |
| II-888 | Me | Et | Me | 2,3-diMe-6-Cl—Ph |
| II-889 | Me | Me | Me | 2,4-diMe-6-Cl—Ph |
| II-890 | Me | Et | Me | 2,4-diMe-6-Cl—Ph |
| II-891 | Me | Me | Me | 2-Me-3-MeO-6-Cl—Ph |
| II-892 | Me | Et | Me | 2-Me-3-MeO-6-Cl—Ph |
| II-893 | Me | Me | Me | 2-Me-4-MeO-6-Cl—Ph |
| II-894 | Me | Et | Me | 2-Me-4-MeO-6-Cl—Ph |
| II-895 | Me | Me | Me | 2-Me-3-F-6-Br—Ph |
| II-896 | Me | Et | Me | 2-Me-3-F-6-Br—Ph |
| II-897 | Me | Me | Me | 2-Me-3-Cl-6-Br—Ph |
| II-898 | Me | Et | Me | 2-Me-3-Cl-6-Br—Ph |
| II-899 | Me | Me | Me | 2-Me-3,6-diBr—Ph |
| II-900 | Me | Et | Me | 2-Me-3,6-diBr—Ph |

TABLE 10

(II)

| Comp. No. | R¹ | R² | R³ | A |
|---|---|---|---|---|
| II-901 | Me | Me | Me | 2,3-diMe-6-Br—Ph |
| II-902 | Me | Et | Me | 2,3-diMe-6-Br—Ph |
| II-903 | Me | Me | Me | 2,4-diMe-6-Br—Ph |
| II-904 | Me | Et | Me | 2,4-diMe-6-Br—Ph |
| II-905 | Me | Me | Me | 2-Me-3-MeO-6-Br—Ph |
| II-906 | Me | Et | Me | 2-Me-3-MeO-6-Br—Ph |
| II-907 | Me | Me | Me | 2-Me-4-MeO-6-Br—Ph |
| II-908 | Me | Et | Me | 2-Me-4-MeO-6-Br—Ph |
| II-909 | Me | Me | Me | 2-Me-3-F-6-Me—Ph |
| II-910 | Me | Et | Me | 2-Me-3-F-6-Me—Ph |
| II-911 | Me | Me | Me | 2-Me-3-Cl-6-Me—Ph |
| II-912 | Me | Et | Me | 2-Me-3-Cl-6-Me—Ph |
| II-913 | Me | Me | Me | 2-Me-3-Br-6-Me—Ph |
| II-914 | Me | Et | Me | 2-Me-3-Br-6-Me—Ph |
| II-915 | Me | Me | Me | 2,3,6-triMe—Ph |
| II-916 | Me | Et | Me | 2,3,6-triMe—Ph |
| II-917 | Me | Me | Me | 2,4,6-triMe—Ph |
| II-918 | Me | Et | Me | 2,4,6-triMe—Ph |
| II-919 | Me | Me | Me | 2-Me-3-MeO-6-Me—Ph |
| II-920 | Me | Et | Me | 2-Me-3-MeO-6-Me—Ph |
| II-921 | Me | Me | Me | 2-Me-4-MeO-6-Me—Ph |
| II-922 | Me | Et | Me | 2-Me-4-MeO-6-Me—Ph |
| II-923 | Me | Me | Me | 2-Me-3-F-6-MeO—Ph |
| II-924 | Me | Et | Me | 2-Me-3-F-6-MeO—Ph |
| II-925 | Me | Me | Me | 2-Me-3-Cl-6-MeO—Ph |
| II-926 | Me | Et | Me | 2-Me-3-Cl-6-MeO—Ph |
| II-927 | Me | Me | Me | 2-Me-3-Br-6-MeO—Ph |
| II-928 | Me | Et | Me | 2-Me-3-Br-6-MeO—Ph |
| II-929 | Me | Me | Me | 2,3-diMe-6-MeO—Ph |
| II-930 | Me | Et | Me | 2,3-diMe-6-MeO—Ph |
| II-931 | Me | Me | Me | 2,4-diMe-6-MeO—Ph |
| II-932 | Me | Et | Me | 2,4-diMe-6-MeO—Ph |
| II-933 | Me | Me | Me | 2-Me-3,6-diMeO—Ph |
| II-934 | Me | Et | Me | 2-Me-3,6-diMeO—Ph |
| II-935 | Me | Me | Me | 2-Me-4,6-diMeO—Ph |
| II-936 | Me | Et | Me | 2-Me-4,6-diMeO—Ph |
| II-937 | Me | Me | Me | 2-MeO-3,6-diF—Ph |
| II-938 | Me | Et | Me | 2-MeO-3,6-diF—Ph |
| II-939 | Me | Me | Me | 2-MeO-3-Cl-6-F—Ph |
| II-940 | Me | Et | Me | 2-MeO-3-Cl-6-F—Ph |
| II-941 | Me | Me | Me | 2-MeO-3-Br-6-F—Ph |
| II-942 | Me | Et | Me | 2-MeO-3-Br-6-F—Ph |
| II-943 | Me | Me | Me | 2-MeO-3-Me-6-F—Ph |
| II-944 | Me | Et | Me | 2-MeO-3-Me-6-F—Ph |
| II-945 | Me | Me | Me | 2,3-diMeO-6-F—Ph |
| II-946 | Me | Et | Me | 2,3-diMeO-6-F—Ph |
| II-947 | Me | Me | Me | 2,4-diMeO-6-F—Ph |
| II-948 | Me | Et | Me | 2,4-diMeO-6-F—Ph |
| II-949 | Me | Me | Me | 2-MeO-3-F-6-Cl—Ph |
| II-950 | Me | Et | Me | 2-MeO-3-F-6-Cl—Ph |
| II-951 | Me | Me | Me | 2-MeO-3,6-Cl—Ph |
| II-952 | Me | Et | Me | 2-MeO-3,6-Cl—Ph |
| II-953 | Me | Me | Me | 2-MeO-3-Br-6-Cl—Ph |
| II-954 | Me | Et | Me | 2-MeO-3-Br-6-Cl—Ph |
| II-955 | Me | Me | Me | 2-MeO-3-Me-6-Cl—Ph |
| II-956 | Me | Et | Me | 2-MeO-3-Me-6-Cl—Ph |
| II-957 | Me | Me | Me | 2,3-diMeO-6-Cl—Ph |
| II-958 | Me | Et | Me | 2,3-diMeO-6-Cl—Ph |
| II-959 | Me | Me | Me | 2,4-diMeO-6-Cl—Ph |
| II-960 | Me | Et | Me | 2,4-diMeO-6-Cl—Ph |
| II-961 | Me | Me | Me | 2-MeO-3-F-6-Br—Ph |
| II-962 | Me | Et | Me | 2-MeO-3-F-6-Br—Ph |
| II-963 | Me | Me | Me | 2-MeO-3-Cl-6-Br—Ph |
| II-964 | Me | Et | Me | 2-MeO-3-Cl-6-Br—Ph |

TABLE 10-continued (II)

| Comp. No. | R¹ | R² | R³ | A |
|---|---|---|---|---|
| II-965 | Me | Me | Me | 2-MeO-3,6-diBr—Ph |
| II-966 | Me | Et | Me | 2-MeO-3,6-diBr—Ph |
| II-967 | Me | Me | Me | 2-MeO-3-Me-6-Br—Ph |
| II-968 | Me | Et | Me | 2-MeO-3-Me-6-Br—Ph |
| II-969 | Me | Me | Me | 2,3-diMeO-6-Br—Ph |
| II-970 | Me | Et | Me | 2,3-diMeO-6-Br—Ph |
| II-971 | Me | Me | Me | 2,4-diMeO-6-Br—Ph |
| II-972 | Me | Et | Me | 2,4-diMeO-6-Br—Ph |
| II-973 | Me | Me | Me | 2-MeO-3-F-6-Me—Ph |
| II-974 | Me | Et | Me | 2-MeO-3-F-6-Me—Ph |
| II-975 | Me | Me | Me | 2-MeO-3-Cl-6-Me—Ph |
| II-976 | Me | Et | Me | 2-MeO-3-Cl-6-Me—Ph |
| II-977 | Me | Me | Me | 2-MeO-3-Br-6-Me—Ph |
| II-978 | Me | Et | Me | 2-MeO-3-Br-6-Me—Ph |
| II-979 | Me | Me | Me | 2-MeO-3,6-diMe—Ph |
| II-980 | Me | Et | Me | 2-MeO-3,6-diMe—Ph |
| II-981 | Me | Me | Me | 2,3-diMeO-6-Me—Ph |
| II-982 | Me | Et | Me | 2,3-diMeO-6-Me—Ph |
| II-983 | Me | Me | Me | 2,4-diMeO-6-Me—Ph |
| II-984 | Me | Et | Me | 2,4-diMeO-6-Me—Ph |
| II-985 | Me | Me | Me | 2,6-di-MeO-3-F—Ph |
| II-986 | Me | Et | Me | 2,6-di-MeO-3-F—Ph |
| II-987 | Me | Me | Me | 2,6-di-MeO-3-Cl—Ph |
| II-988 | Me | Et | Me | 2,6-di-MeO-3-Cl—Ph |
| II-989 | Me | Me | Me | 2,6-di-MeO-3-Br—Ph |
| II-990 | Me | Et | Me | 2,6-di-MeO-3-Br—Ph |
| II-991 | Me | Me | Me | 2,6-di-MeO-3-Me—Ph |
| II-992 | Me | Et | Me | 2,6-di-MeO-3-Me—Ph |
| II-993 | Me | Me | Me | 2,3,6-triMeO—Ph |
| II-994 | Me | Et | Me | 2,3,6-triMeO—Ph |
| II-995 | Me | Me | Me | 2,4,6-triMeO—Ph |
| II-996 | Me | Et | Me | 2,4,6-triMeO—Ph |

TABLE 11

(II)

| Comp. No. | R¹ | R² | R³ | A |
|---|---|---|---|---|
| II-997 | Me | Me | Me | 6-F-2,3-dihydrobenzofuran-7-yl |
| II-998 | Me | Et | Me | 6-F-2,3-dihydrobenzofuran-7-yl |
| II-999 | Me | Me | Me | 6-Cl-2,3-dihydrobenzofuran-7-yl |
| II-1000 | Me | Et | Me | 6-Cl-2,3-dihydrobenzofuran-7-yl |
| II-1001 | Me | Me | Me | 6-Br-2,3-dihydrobenzofuran-7-yl |
| II-1002 | Me | Et | Me | 6-Br-2,3-dihydrobenzofuran-7-yl |
| II-1003 | Me | Me | Me | 6-Me-2,3-dihydrobenzofuran-7-yl |
| II-1004 | Me | Et | Me | 6-Me-2,3-dihydrobenzofuran-7-yl |
| II-1005 | Me | Me | Me | 6-MeO-2,3-dihydrobenzofuran-7-yl |
| II-1006 | Me | Et | Me | 6-MeO-2,3-dihydrobenzofuran-7-yl |

TABLE 11-continued (II)

| Comp. No. | R¹ | R² | R³ | A |
|---|---|---|---|---|
| II-1007 | Me | Me | Me | pyridin-2-yl |
| II-1008 | Me | Et | Me | pyridin-2-yl |
| II-1009 | Me | Me | Me | 3-F-pyridin-2-yl |
| II-1010 | Me | Et | Me | 3-F-pyridin-2-yl |
| II-1011 | Me | Me | Me | 3-Cl-pyridin-2-yl |
| II-1012 | Me | Et | Me | 3-Cl-pyridin-2-yl |
| II-1013 | Me | Me | Me | 3-Br-pyridin-2-yl |
| II-1014 | Me | Et | Me | 3-Br-pyridin-2-yl |
| II-1015 | Me | Me | Me | 3-Me-pyridin-2-yl |
| II-1016 | Me | Et | Me | 3-Me-pyridin-2-yl |
| II-1017 | Me | Me | Me | 3-MeO-pyridin-2-yl |
| II-1018 | Me | Et | Me | 3-MeO-pyridin-2-yl |
| II-1019 | Me | Me | Me | pyridin-3-yl |
| II-1020 | Me | Et | Me | pyridin-3-yl |
| II-1021 | Me | Me | Me | 2-F-pyridin-3-yl |
| II-1022 | Me | Et | Me | 2-F-pyridin-3-yl |
| II-1023 | Me | Me | Me | 2-Cl-pyridin-3-yl |
| II-1024 | Me | Et | Me | 2-Cl-pyridin-3-yl |
| II-1025 | Me | Me | Me | 2-Br-pyridin-3-yl |
| II-1026 | Me | Et | Me | 2-Br-pyridin-3-yl |
| II-1027 | Me | Me | Me | 2-MeO-pyridin-3-yl |
| II-1028 | Me | Et | Me | 2-MeO-pyridin-3-yl |
| II-1029 | Me | Me | Me | pyridin-4-yl |
| II-1030 | Me | Et | Me | pyridin-4-yl |
| II-1031 | Me | Me | Me | 3-F-isothiazol-4-yl |
| II-1032 | Me | Et | Me | 3-F-isothiazol-4-yl |
| II-1033 | Me | Me | Me | 3-Cl-isothiazol-4-yl |
| II-1034 | Me | Et | Me | 3-Cl-isothiazol-4-yl |
| II-1035 | Me | Me | Me | 3-Me-isothiazol-4-yl |
| II-1036 | Me | Et | Me | 3-Me-isothiazol-4-yl |
| II-1037 | Me | Me | Me | 3-F-isoxazol-4-yl |
| II-1038 | Me | Et | Me | 3-F-isoxazol-4-yl |
| II-1039 | Me | Me | Me | 3-Cl-isoxazol-4-yl |
| II-1040 | Me | Et | Me | 3-Cl-isoxazol-4-yl |
| II-1041 | Me | Me | Me | 3-Me-isoxazol-4-yl |
| II-1042 | Me | Et | Me | 3-Me-isoxazol-4-yl |
| II-1043 | Me | Me | Me | thiophen-2-yl |
| II-1044 | Me | Et | Me | thiophen-2-yl |
| II-1045 | Me | Me | Me | thiophen-3-yl |
| II-1046 | Me | Et | Me | thiophen-3-yl |

TABLE 12

(II)

| Comp. No. | R¹ | R² | R³ | A |
|---|---|---|---|---|
| II-1047 | Me | Me | Me | benzofuran-7-yl |
| II-1048 | Me | Et | Me | benzofuran-7-yl |

TABLE 12-continued (II)

| Comp. No. | R[1] | R[2] | R[3] | A |
|---|---|---|---|---|
| II-1049 | Me | Me | Me | 6-F-benzofuran-7-yl |
| II-1050 | Me | Et | Me | 6-F-benzofuran-7-yl |
| II-1051 | Me | Me | Me | 6-Cl-benzofuran-7-yl |
| II-1052 | Me | Et | Me | 6-Cl-benzofuran-7-yl |
| II-1053 | Me | Me | Me | 6-Br-benzofuran-7-yl |
| II-1054 | Me | Et | Me | 6-Br-benzofuran-7-yl |
| II-1055 | Me | Me | Me | 6-Me-benzofuran-7-yl |
| II-1056 | Me | Et | Me | 6-Me-benzofuran-7-yl |
| II-1057 | Me | Me | Me | 6-MeO-benzofuran-7-yl |
| II-1058 | Me | Et | Me | 6-MeO-benzofuran-7-yl |
| II-1059 | Me | Me | Me | 2-Me-6-F-benzofuran-7-yl |
| II-1060 | Me | Et | Me | 2-Me-6-F-benzofuran-7-yl |
| II-1061 | Me | Me | Me | 3-Me-6-F-benzofuran-7-yl |
| II-1062 | Me | Et | Me | 3-Me-6-F-benzofuran-7-yl |
| II-1063 | Me | Me | Me | 2-Cl-6-F-benzofuran-7-yl |
| II-1064 | Me | Et | Me | 2-Cl-6-F-benzofuran-7-yl |
| II-1065 | Me | Me | Me | 3-Cl-6-F-benzofuran-7-yl |
| II-1066 | Me | Et | Me | 3-Cl-6-F-benzofuran-7-yl |
| II-1067 | Me | Me | Me | 2-Me-6-Cl-benzofuran-7-yl |
| II-1068 | Me | Et | Me | 2-Me-6-Cl-benzofuran-7-yl |
| II-1069 | Me | Me | Me | 3-Me-6-Cl-benzofuran-7-yl |
| II-1070 | Me | Et | Me | 3-Me-6-Cl-benzofuran-7-yl |
| II-1071 | Me | Me | Me | 2-Cl-6-Cl-benzofuran-7-yl |
| II-1072 | Me | Et | Me | 2-Cl-6-Cl-benzofuran-7-yl |
| II-1073 | Me | Me | Me | 3-Cl-6-Cl-benzofuran-7-yl |
| II-1074 | Me | Et | Me | 3-Cl-6-Cl-benzofuran-7-yl |

Advantageous Effects of Invention

A pharmaceutical composition comprising a compound represented by the formula (I) or a pharmacologically acceptable salt thereof, the pharmaceutical composition being administered in combination with an immunotherapeutic agent, is useful as a drug for the treatment and/or prevention of tumor.

DESCRIPTION OF EMBODIMENTS

One embodiment of the present invention will be described below. In the present specification, each "compound represented by the general formula (I)", etc. is also referred to as "compound (I)", etc. for the sake of convenience. Various substituents defined or illustrated below can be arbitrarily selected and combined. In the present specification, the "substituted dihydropyrrolopyrazole compound" is also referred to as a "substituted dihydropyrrolopyrazole derivative".

One embodiment of the present invention is a pharmaceutical composition comprising a compound represented by the formula (I) or a pharmaceutically acceptable salt thereof, wherein the pharmaceutical composition is administered in combination with an immunotherapeutic agent.

<1. Compound Represented by Formula (I) or Pharmaceutically Acceptable Salt Thereof>

[Chemical Formula 4]

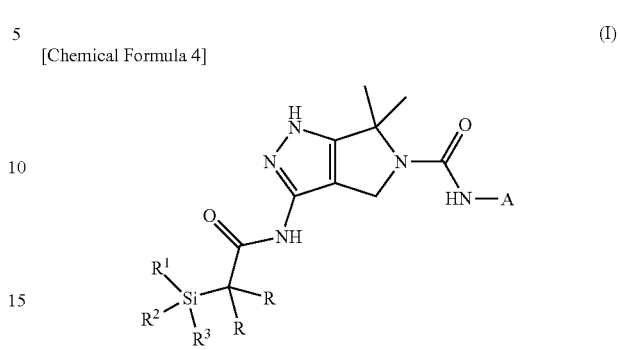

(I)

In the formula, two R moieties each independently are a $C_{1-3}$ alkyl group or are groups bonded to each other to form a $C_{2-5}$ alkylene group;

A is an optionally substituted $C_{6-10}$ aryl group or an optionally substituted heteroaryl group; and $R^1$, $R^2$ and $R^3$ each independently are an optionally substituted linear or branched $C_{1-4}$ alkyl group.

In the present specification, the term "optionally substituted" means that the group may be unsubstituted or may be further substituted by a substituent.

The substituent means a monovalent group, and examples thereof include linear or branched $C_{1-6}$ alkyl groups, $C_{3-6}$ cycloalkyl groups, linear or branched $C_{2-6}$ alkenyl groups, $C_{3-6}$ cycloalkenyl groups, linear or branched $C_{2-6}$ alkynyl groups, $C_{1-6}$ alkoxy groups, halogen atoms, a hydroxy group, a cyano group, an oxo group (=O), an amino group, $C_{1-6}$ alkylamino groups, a nitro group, a carboxy group (—COOH), a carbamoyl group (—CONH$_2$), N-mono-$C_{1-6}$ alkylcarbamoyl groups, N,N-di-$C_{1-6}$ alkylcarbamoyl groups (two alkyl groups may be different), $C_{1-6}$ alkanoyloxy groups (—OCOR$^4$; R$^4$ is a $C_{1-3}$ alkyl group), $C_{6-10}$ aryl groups, and heterocyclic groups. The substituent may be further substituted by a halogen atom, a hydroxy group, an amino group, a cyano group, an oxo group (=O), a linear or branched $C_{1-6}$ alkyl group, a $C_{1-6}$ alkoxy group, a $C_{6-10}$ aryl group, a heterocyclic group, or the like. In the case where the substituent is an amino group or a carboxy group, the form may be a salt thereof.

In the case where the group concerned has two or more substituents, two substituents may be bonded to each other to form a cyclic structure. Examples of the case where two substituents are bonded to each other to form a cyclic structure include a cyclopropyl group, a methylenedioxy group, and an oxyethylene group.

Specifically, in the case where a methylenedioxy group is bonded to a benzene ring, the substituent becomes a 1,3-benzodioxole group; in the case where an oxyethylene group is bonded to a benzene ring, the substituent becomes a 2,3-dihydrobenzofuranyl group.

The linear or branched $C_{1-6}$ alkyl group described in the present specification means a linear or branched alkyl group having 1 to 6 carbon atoms. Examples of the linear or branched $C_{1-6}$ alkyl group include $C_{1-6}$ alkyl groups such as a methyl group, an ethyl group, a propyl group, an isopropyl group, a butyl group, an isobutyl group, a sec-butyl group, a tert-butyl group, a pentyl group, an isopentyl group, a neopentyl group, a tert-pentyl group, a 1-ethylpropyl group, a 1-methylbutyl group, a 2-methylbutyl group, a 1,2-dimethylpropyl group, a hexyl group, a 1-methylpentyl group, a 2-methylpentyl group, a 3-methylpentyl group, a 4-methylpentyl group, a 1-ethylbutyl group, a 2-ethylbutyl group, a 1,1-dimethylbutyl group, a 2,2-dimethylbutyl group, a 3,3-dimethylbutyl group, a 1,2-dimethylbutyl group, a 1,3-dimethylbutyl group, and a 2,3-dimethylbutyl group. The substituent is preferably a methyl group, an ethyl group, a propyl group, an isopropyl group, a butyl group, an isobutyl group, a sec-butyl group, or a tert-butyl group.

Examples of a $C_{1-6}$ alkyl group substituted by a halogen atom include a chloromethyl group, a bromomethyl group, an iodomethyl group, a difluoromethyl group, a dichloromethyl group, a dibromomethyl group, a diiodomethyl group, a trifluoromethyl group, a trichloromethyl group, a 1-fluoroethyl group, a 2-fluoroethyl group, a 2-chloroethyl group, a 2-bromoethyl group, a 2,2-difluoroethyl group, a 2,2,2-trifluoroethyl group, a pentafluoroethyl group, a 2,2-dichloroethyl group, a 2,2,2-trichloroethyl group, a 1-fluoropropyl group, a 2-fluoropropyl group, a 3-fluoropropyl group, a 3,3,3-trifluoropropyl group, a perfluoropropyl group, a 1-fluoromethylethyl group, a 1-difluoromethylethyl group, a 1-trifluoromethylethyl group, a 1-fluoro-1-methylethyl group, a 4-fluorobutyl group, a perfluorobutyl group, a 5-fluoropentyl group, a perfluoropentyl group, a 6-fluorohexyl group, and a perfluorohexyl group.

A $C_{1-6}$ alkyl group substituted by an aryl group may be, for example, a $C_{7-11}$ aralkyl group. The $C_{7-11}$ aralkyl group means an alkyl group having an aryl group and having a total of 7 to 11 carbon atoms, and examples thereof include a benzyl group, a phenylethyl group, and a naphthylmethyl group.

The $C_{3-6}$ cycloalkyl group described in the present specification means a cyclic alkyl group having 3 to 6 carbon atoms. Examples of the $C_{3-6}$ cycloalkyl group include: monocyclic rings such as a cyclopropyl group, a cyclobutyl group, a cyclopentyl group, and a cyclohexyl group; condensed rings such as a bicyclo[3.1.0]hexyl group; and spiro rings such as a spiro[2.3]hexyl group. The substituent is preferably a cyclopropyl group or a cyclobutyl group.

The linear or branched $C_{2-6}$ alkenyl group described in the present specification means a linear or branched alkenyl group having 2 to 6 carbon atoms. Examples of the linear or branched $C_{2-6}$ alkenyl group include alkenyl groups such as a vinyl group, a propen-1-yl group, a propen-2-yl group, a 1-butenyl group, a 2-butenyl group, a 3-butenyl group, a 1-methyl-1-propenyl group, a 2-methyl-1-propenyl group, a 1-pentenyl group, a 2-pentenyl group, a 3-pentenyl group, a 4-pentenyl group, a 5-pentenyl group, a 1-methyl-1-butenyl group, a 2-methyl-1-butenyl group, a 3-methyl-1-butenyl group, a 4-methyl-1-butenyl group, a 1-methyl-2-butenyl group, a 2-methyl-2-butenyl group, a 3-methyl-2-butenyl group, a 4-methyl-2-butenyl group, a 1-methyl-3-butenyl group, a 2-methyl-3-butenyl group, a 3-methyl-3-butenyl group, a 4-methyl-3-butenyl group, a 1,2-dimethyl-1-propenyl group, a 1-hexenyl group, a 2-hexenyl group, a 3-hexenyl group, a 4-hexenyl group, a 5-hexenyl group, a 6-hexenyl group, and structural isomers thereof.

The $C_{3-6}$ cycloalkenyl group described in the present specification means a cycloalkenyl group having 3 to 6 carbon atoms. Examples of the $C_{3-6}$ cycloalkenyl group include a cyclopropenyl group, a cyclobutenyl group, a cyclopentenyl group, and a cyclohexenyl group.

The $C_{2-6}$ alkynyl group described in the present specification means an alkynyl group having 2 to 6 carbon atoms. Examples of the $C_{2-6}$ alkynyl group include an ethynyl group, a propargyl group, a butynyl group, a pentynyl group, and a hexynyl group.

The $C_{1-6}$ alkoxy group described in the present specification means a group consisting of an oxy group (—O—) and a linear or branched $C_{1-6}$ alkyl group or a $C_{3-6}$ cycloalkyl group bonded to the oxy group. Examples of the $C_{1-6}$ alkoxy group include a methoxy group, an ethoxy group, a propyloxy group, an isopropyloxy group, a cyclopropyloxy group, a butoxy group, a cyclobutyloxy group, a pentyloxy group, a cyclopentyloxy group, a hexyloxy group, and a cyclohexyloxy group.

The $C_{1-6}$ alkylamino group described in the present specification means an amino group substituted by one or two independently selected aforementioned linear or branched $C_{1-6}$ alkyl groups or $C_{3-6}$ cycloalkyl groups. Examples of the $C_{1-6}$ alkylamino group include a methylamino group, an ethylamino group, a propylamino group, an isopropylamino group, a cyclopropylamino group, a butylamino group, a cyclobutylamino group, a pentylamino group, a cyclopentylamino group, a hexylamino group, a cyclohexylamino group, a dimethylamino group, a diethylamino group, an ethyl(methyl)amino group, an isopropyl(methyl)amino group, and a cyclopropyl(methyl)amino group.

The halogen atom described in the present specification means a fluorine atom, a chlorine atom, a bromine atom, or an iodine atom.

The $C_{6-10}$ aryl group described in the present specification means an aryl group having 6 to 10 carbon atoms. Examples of the $C_{6-10}$ aryl group include a phenyl group and a naphthyl group.

The heterocyclic group described in the present specification means a cyclic group having at least one nitrogen atom, oxygen atom, or sulfur atom and may be an aromatic heterocyclic group or may be a nonaromatic heterocyclic group. Examples of the aromatic heterocyclic group include a pyridine group, a pyrimidine group, a pyridazine group, a pyrazine group, a triazine group, a pyrrole group, an imidazole group, a pyrazole group, an indole group, an indazole group, a furan group, a benzofuran group, a thiophene group, a benzothiophene group, a thiazole group, an isothiazole group, an oxazole group, an isoxazole group, and an oxadiazole group. Examples of the nonaromatic heterocyclic group include a pyrrolidinyl group, a piperidinyl group, a piperazinyl group, a morpholinyl group, and a thiomorpholinyl group.

The $C_{2-5}$ alkylene group formed by two R moieties bonded to each other means a divalent group obtained by further removing one hydrogen atom from a $C_{2-5}$ alkyl group which corresponds to one having 2 to 5 carbon atoms among the $C_{1-6}$ alkyl groups described above. Examples of the $C_{2-5}$ alkylene group include a 1,2-ethylene group, a 1,2-propylene group, a 1,3-propylene group, a 1,2-butylene group, a 1,3-butylene group, a 1,4-butylene group, a 2,3-butylene group, a 1,2-pentylene group, a 1,3-pentylene group, a 1,4-pentylene group, a 1,5-pentylene group, a 2,3-pentylene group, and a 2,4-pentylene group.

The linear or branched $C_{1-4}$ alkyl group as $R^1$, $R^2$ or $R^3$ is a linear or branched alkyl group having 1 to 4 carbon atoms and corresponds to one having 1 to 4 carbon atoms among the $C_{1-6}$ alkyl groups described above.

The $C_{1-3}$ alkyl group as $R^4$ is an alkyl group having 1 to 3 carbon atoms and corresponds to one having 1 to 3 carbon atoms among the $C_{1-6}$ alkyl groups described above. Examples of the $C_{1-3}$ alkyl group include a methyl group, an ethyl group, a propyl group, and an isopropyl group.

The heteroaryl group as A corresponds to an aromatic heterocyclic group among the heterocyclic groups described above.

The compound according to the present embodiment may be a compound represented by any chemical formula of the general formula (II), the general formula (III), or the general formula (IV).

[Chemical Formula 5]

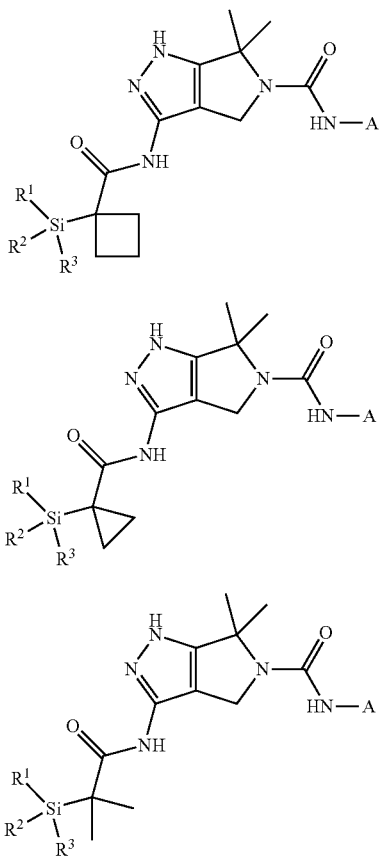

In the general formula (II), the general formula (III), and the general formula (IV), $R^1$, $R^2$, $R^3$, and A are as defined in the general formula (I).

In the general formula (I), two R moieties may each independently be a $C_{1-3}$ alkyl group or may be groups bonded to each other to form a $C_{2-5}$ alkylene group.

In the general formula (I), the general formula (II), the general formula (III), and the general formula (IV), $R^1$, $R^2$ and $R^3$ may each independently be an optionally substituted linear or branched $C_{1-4}$ alkyl group.

In the general formula (I), the general formula (II), the general formula (III), and the general formula (IV), A may be an optionally substituted $C_{6-10}$ aryl group or an optionally substituted heteroaryl group.

Compound (I) is preferably a compound represented by compound (II). Also, among compounds (II), a compound selected from the following compound group is preferred:

6,6-dimethyl-N-phenyl-3-[1-(trimethylsilyl)cyclobutanecarboxamido]-4,6-dihydropyrrolo[3,4-c]pyrazole-5(1H)-carboxamide (Compound No. II-1)

6,6-dimethyl-N-(p-tolyl)-3-[1-(trimethylsilyl)cyclobutanecarboxamido]-4,6-dihydropyrrolo[3,4-c]pyrazole-5(1H)-carboxamide (Compound No. II-25)

N-(4-methoxyphenyl)-6,6-dimethyl-3-[1-(trimethylsilyl)cyclobutanecarboxamido]-4,6-dihydropyrrolo[3,4-c]pyrazole-5(1H)-carboxamide (Compound No. II-79)

N-(4-fluorophenyl)-6,6-dimethyl-3-[1-(trimethylsilyl)cyclobutanecarboxamido]-4,6-dihydropyrrolo[3,4-c]pyrazole-5(1H)-carboxamide (Compound No. II-7)

6,6-dimethyl-N-(pyridin-3-yl)-3-[1-(trimethylsilyl)cyclobutanecarboxamido]-4,6-dihydropyrrolo[3,4-c]pyrazole-5(1H)-carboxamide (Compound No. II-1019)

N-(2-fluorophenyl)-6,6-dimethyl-3-[1-(trimethylsilyl)cyclobutanecarboxamido]-4,6-dihydropyrrolo[3,4-c]pyrazole-5(1H)-carboxamide (Compound No. II-3)

6,6-dimethyl-N-(o-tolyl)-3-[1-(trimethylsilyl)cyclobutanecarboxamido]-4,6-dihydropyrrolo[3,4-c]pyrazole-5(1H)-carboxamide (Compound No. II-21)

6,6-dimethyl-N-(m-tolyl)-3-[1-(trimethylsilyl)cyclobutanecarboxamido]-4,6-dihydropyrrolo[3,4-c]pyrazole-5(1H)-carboxamide (Compound No. II-23)

N-([1,1'-biphenyl]-3-yl)-6,6-dimethyl-3-[1-(trimethylsilyl)cyclobutanecarboxamido]-4,6-dihydropyrrolo[3,4-c]pyrazole-5(1H)-carboxamide (Compound No. II-71)

N-(3-fluorophenyl)-6,6-dimethyl-3-[1-(trimethylsilyl)cyclobutanecarboxamido]-4,6-dihydropyrrolo[3,4-c]pyrazole-5(1H)-carboxamide (Compound No. II-5)

N-(3-chlorophenyl)-6,6-dimethyl-3-[1-(trimethylsilyl)cyclobutanecarboxamido]-4,6-dihydropyrrolo[3,4-c]pyrazole-5(1H)-carboxamide (Compound No. II-11)

N-(2-methoxyphenyl)-6,6-dimethyl-3-[1-(trimethylsilyl)cyclobutanecarboxamido]-4,6-dihydropyrrolo[3,4-c]pyrazole-5(1H)-carboxamide (Compound No. II-75)

N-(2-chlorophenyl)-6,6-dimethyl-3-[1-(trimethylsilyl)cyclobutanecarboxamido]-4,6-dihydropyrrolo[3,4-c]pyrazole-5(1H)-carboxamide (Compound No. II-9)

N-([1,1'-biphenyl]-2-yl)-6,6-dimethyl-3-[1-(trimethylsilyl)cyclobutanecarboxamido]-4,6-dihydropyrrolo[3,4-c]pyrazole-5(1H)-carboxamide (Compound No. II-69)

6,6-dimethyl-N-(pyridin-2-yl)-3-[1-(trimethylsilyl)cyclobutanecarboxamido]-4,6-dihydropyrrolo[3,4-c]pyrazole-5(1H)-carboxamide (Compound No. II-1007)

N-(2-ethylphenyl)-6,6-dimethyl-3-[1-(trimethylsilyl)cyclobutanecarboxamido]-4,6-dihydropyrrolo[3,4-c]pyrazole-5(1H)-carboxamide (Compound No. II-27)

N-(2,6-dimethylphenyl)-6,6-dimethyl-3-[1-(trimethylsilyl)cyclobutanecarboxamido]-4,6-dihydropyrrolo[3,4-c]pyrazole-5(1H)-carboxamide (Compound No. II-381)

N-(2,3-difluorophenyl)-6,6-dimethyl-3-[1-(trimethylsilyl)cyclobutanecarboxamido]-4,6-dihydropyrrolo[3,4-c]pyrazole-5(1H)-carboxamide (Compound No. II-99)

N-(2,3-dimethylphenyl)-6,6-dimethyl-3-[1-(trimethylsilyl)cyclobutanecarboxamido]-4,6-dihydropyrrolo[3,4-c]pyrazole-5(1H)-carboxamide (Compound No. II-375)

N-(2-fluoro-6-methylphenyl)-6,6-dimethyl-3-[1-(trimethylsilyl)cyclobutanecarboxamido]-4,6-dihydropyrrolo[3,4-c]pyrazole-5(1H)-carboxamide (Compound No. II-129)

N-[2-(difluoromethoxy)phenyl]-6,6-dimethyl-3-[1-(trimethylsilyl)cyclobutanecarboxamido]-4,6-dihydropyrrolo[3,4-c]pyrazole-5(1H)-carboxamide (Compound No. II-87)

N-(2-ethoxyphenyl)-6,6-dimethyl-3-[1-(trimethylsilyl)cyclobutanecarboxamido]-4,6-dihydropyrrolo[3,4-c]pyrazole-5(1H)-carboxamide (Compound No. II-81)

6,6-dimethyl-N-(2-(trifluoromethoxy)phenyl)-3-[1-(trimethylsilyl)cyclobutanecarboxamido]-4,6-dihydropyrrolo[3,4-c]pyrazole-5(1H)-carboxamide (Compound No. II-93)

N-(2-fluoro-4-methylphenyl)-6,6-dimethyl-3-[1-(trimethylsilyl)cyclobutanecarboxamido]-4,6-dihydropyrrolo[3,4-c]pyrazole-5(1H)-carboxamide (Compound No. II-125)

N-(2,6-difluorophenyl)-6,6-dimethyl-3-[1-(trimethylsilyl)cyclobutanecarboxamido]-4,6-dihydropyrrolo[3,4-c]pyrazole-5(1H)-carboxamide (Compound No. II-105)

N-[2-(tert-butyl)phenyl]-6,6-dimethyl-3-[1-(trimethylsilyl)cyclobutanecarboxamido]-4,6-dihydropyrrolo[3,4-c]pyrazole-5(1H)-carboxamide (Compound No. II-57)

6,6-dimethyl-N-(2-(trifluoromethyl)phenyl)-3-[1-(trimethylsilyl)cyclobutanecarboxamido]-4,6-dihydropyrrolo[3,4-c]pyrazole-5(1H)-carboxamide (Compound No. II-51)

N-(3-fluoro-2-methylphenyl)-6,6-dimethyl-3-[1-(trimethylsilyl)cyclobutanecarboxamido]-4,6-dihydropyrrolo[3,4-c]pyrazole-5(1H)-carboxamide (Compound No. II-357)

N-(2-cyanophenyl)-6,6-dimethyl-3-[1-(trimethylsilyl)cyclobutanecarboxamido]-4,6-dihydropyrrolo[3,4-c]pyrazole-5(1H)-carboxamide (Compound No. II-63)

N-(4-fluoro-2-methylphenyl)-6,6-dimethyl-3-[1-(trimethylsilyl)cyclobutanecarboxamido]-4,6-dihydropyrrolo[3,4-c]pyrazole-5(1H)-carboxamide (Compound No. II-359)

N-(2-chloro-6-methylphenyl)-6,6-dimethyl-3-[1-(trimethylsilyl)cyclobutanecarboxamido]-4,6-dihydropyrrolo[3,4-c]pyrazole-5(1H)-carboxamide (Compound No. II-215)

N-(2-fluoro-3-methylphenyl)-6,6-dimethyl-3-[1-(trimethylsilyl)cyclobutanecarboxamido]-4,6-dihydropyrrolo[3,4-c]pyrazole-5(1H)-carboxamide (Compound No. II-123)

N-(2-fluoro-5-methylphenyl)-6,6-dimethyl-3-[1-(trimethylsilyl)cyclobutanecarboxamido]-4,6-dihydropyrrolo[3,4-c]pyrazole-5(1H)-carboxamide (Compound No. II-127)

N-(5-fluoro-2-methylphenyl)-6,6-dimethyl-3-[1-(trimethylsilyl)cyclobutanecarboxamido]-4,6-dihydropyrrolo[3,4-c]pyrazole-5(1H)-carboxamide (Compound No. II-361)

N-(2,4-difluorophenyl)-6,6-dimethyl-3-[1-(trimethylsilyl)cyclobutanecarboxamido]-4,6-dihydropyrrolo[3,4-c]pyrazole-5(1H)-carboxamide (Compound No. II-101)

N-(2,5-difluorophenyl)-6,6-dimethyl-3-[1-(trimethylsilyl)cyclobutanecarboxamido]-4,6-dihydropyrrolo[3,4-c]pyrazole-5(1H)-carboxamide (Compound No. II-103)

N-(2,5-dimethylphenyl)-6,6-dimethyl-3-[1-(trimethylsilyl)cyclobutanecarboxamido]-4,6-dihydropyrrolo[3,4-c]pyrazole-5(1H)-carboxamide (Compound No. II-379)

N-(2-chloro-6-fluorophenyl)-6,6-dimethyl-3-[1-(trimethylsilyl)cyclobutanecarboxamido]-4,6-dihydropyrrolo[3,4-c]pyrazole-5(1H)-carboxamide (Compound No. II-113)

N-(2,4-dimethylphenyl)-6,6-dimethyl-3-[1-(trimethylsilyl)cyclobutanecarboxamido]-4,6-dihydropyrrolo[3,4-c]pyrazole-5(1H)-carboxamide (Compound No. II-377)

3-[1-(ethyldimethylsilyl)cyclobutanecarboxamido]-N-(2-fluorophenyl)-6,6-dimethyl-4,6-dihydropyrrolo[3,4-c]pyrazole-5(1H)-carboxamide (Compound No. II-4)

6,6-dimethyl-N-(3-methylisothiazol-4-yl)-3-[1-(trimethylsilyl)cyclobutanecarboxamido]-4,6-dihydropyrrolo[3,4-c]pyrazole-5(1H)-carboxamide (Compound No. II-1035)

6,6-dimethyl-N-(thiophen-2-yl)-3-[1-(trimethylsilyl)cyclobutanecarboxamido]-2,6-dihydropyrrolo[3,4-c]pyrazole-5(1H)-carboxamide (Compound No. II-1043)

6,6-dimethyl-N-(thiophen-3-yl)-3-[1-(trimethylsilyl)cyclobutanecarboxamido]-2,6-dihydropyrrolo[3,4-c]pyrazole-5(1H)-carboxamide (Compound No. II-1045)

N-(2,6-difluoro-4-methoxyphenyl)-6,6-dimethyl-3-[1-(trimethylsilyl)cyclobutanecarboxamido]-4,6-dihydropyrrolo[3,4-c]pyrazole-5(1H)-carboxamide (Compound No. II-615)

N-(2-fluoro-6-methoxyphenyl)-6,6-dimethyl-3-[1-(trimethylsilyl)cyclobutanecarboxamido]-4,6-dihydropyrrolo[3,4-c]pyrazole-5(1H)- carboxamide (Compound No. II-161)

N-[2-fluoro-6-(trifluoromethyl)phenyl]-6,6-dimethyl-3-[1-(trimethylsilyl)cyclobutanecarboxamido]-4,6-dihydropyrrolo[3,4-c]pyrazole-5(1H)-carboxamide (Compound No. II-153)

N-(5-chloro-2-methylphenyl)-6,6-dimethyl-3-[1-(trimethylsilyl)cyclobutanecarboxamido]-4,6-dihydropyrrolo[3,4-c]pyrazole-5(1H)-carboxamide (Compound No. II-367)

N-(2,5-dichlorophenyl)-6,6-dimethyl-3-[1-(trimethylsilyl)cyclobutanecarboxamido]-4,6-dihydropyrrolo[3,4-c]pyrazole-5(1H)-carboxamide (Compound No. II-197)

N-(2-cyclopropylphenyl)-6,6-dimethyl-3-[1-(trimethylsilyl)cyclobutane carboxamido]-4,6-dihydropyrrolo[3,4-c]pyrazole-5(1H)-carboxamide (Compound No. II-39)

N-(2,6-dichlorophenyl)-6,6-dimethyl-3-[1-(trimethylsilyl)cyclobutanecarboxamido]-4,6-dihydropyrrolo[3,4-c]pyrazole-5(1H)-carboxamide (Compound No. II-199)

6,6-dimethyl-N-(2,4,6-trifluorophenyl)-3-[1-(trimethylsilyl)cyclobutane carboxamido]-4,6-dihydropyrrolo[3,4-c]pyrazole-5(1H)-carboxamide (Compound No. II-599)

N-(2-ethyl-6-methylphenyl)-6,6-dimethyl-3-[1-(trimethylsilyl)cyclobutanecarboxamido]-4,6-dihydropyrrolo[3,4-c]pyrazole-5(1H)-carboxamide (Compound No. II-389)

N-(2-bromophenyl)-6,6-dimethyl-3-[1-(trimethylsilyl)cyclobutanecarboxamido]-4,6-dihydropyrrolo[3,4-c]pyrazole-5(1H)-carboxamide (Compound No. II-15)

N-(2-chloro-5-fluorophenyl)-6,6-dimethyl-3-[1-(trimethylsilyl)cyclobutanecarboxamido]-4,6-dihydropyrrolo[3,4-c]pyrazole-5(1H)-carboxamide (Compound No. II-191)

N-(5-chloro-2-fluorophenyl)-6,6-dimethyl-3-[1-(trimethylsilyl)cyclobutanecarboxamido]-4,6-dihydropyrrolo[3,4-c]pyrazole-5(1H)-carboxamide (Compound No. II-111)

6,6-dimethyl-N-(2,3,6-trifluorophenyl)-3-[1-(trimethylsilyl)cyclobutane carboxamido]-4,6-dihydropyrrolo[3,4-c]pyrazole-5(1H)-carboxamide (Compound No. II-597)

N-(2-chloro-6-methoxyphenyl)-6,6-dimethyl-3-[1-(trimethylsilyl)cyclobutanecarboxamido]-4,6-dihydropyrrolo[3,4-c]pyrazole-5(1H)- carboxamide (Compound No. II-247)

N-[2-(1,1-difluoroethyl)phenyl]-6,6-dimethyl-3-[1-(trimethylsilyl)cyclobutanecarboxamido]-4,6-dihydropyrrolo[3,4-c]pyrazole-5(1H)-carboxamide (Compound No. II-45)

N-(6-chloro-2-fluoro-3-methylphenyl)-6,6-dimethyl-3-[1-(trimethylsilyl)cyclobutanecarboxamido]-4,6-dihydropyrrolo[3,4-c]pyrazole-5(1H)-carboxamide (Compound No. II-629)

N-[2-fluoro-6-(methoxy-d3)phenyl]-6,6-dimethyl-3-[1-(trimethylsilyl)cyclobutanecarboxamido]-4,6-dihydropyrrolo[3,4-c]pyrazole-5(1H)-carboxamide (Compound No. II-177)

N-[2-chloro-6-(trifluoromethyl)phenyl]-6,6-dimethyl-3-[1-(trimethylsilyl)cyclobutanecarboxamido]-4,6-dihydropyrrolo[3,4-c]pyrazole-5(1H)-carboxamide (Compound No. II-239)

N-(2-fluoro-6-methoxy-3-methylphenyl)-6,6-dimethyl-3-[1-(trimethylsilyl)cyclobutanecarboxamido]-4,6-dihydropyrrolo[3,4-c]pyrazole-5(1H)-carboxamide (Compound No. II-689)

N-(2,6-difluoro-3-methylphenyl)-6,6-dimethyl-3-[1-(trimethylsilyl)cyclobutanecarboxamido]-4,6-dihydropyrrolo[3,4-c]pyrazole-5(1H)-carboxamide (Compound No. II-609)

N-[2-(difluoromethoxy)-6-fluorophenyl]-6,6-dimethyl-3-[1-(trimethylsilyl)cyclobutanecarboxamido]-4,6-dihydropyrrolo[3,4-c]pyrazole-5(1H)-carboxamide (Compound No. II-169)

N-(2-bromo-6-chlorophenyl)-6,6-dimethyl-3-[1-(trimethylsilyl)cyclobutanecarboxamido]-4,6-dihydropyrrolo[3,4-c]pyrazole-5(1H)-carboxamide (Compound No. II-207)

N-(2-chloro-6-fluoro-3-methylphenyl)-6,6-dimethyl-3-[1-(trimethylsilyl)cyclobutanecarboxamido]-4,6-dihydropyrrolo[3,4-c]pyrazole-5(1H)-carboxamide (Compound No. II-703)

N-(2-ethyl-6-fluorophenyl)-6,6-dimethyl-3-[1-(trimethylsilyl)cyclobutanecarboxamido]-4,6-dihydropyrrolo[3,4-c]pyrazole-5(1H)-carboxamide (Compound No. II-137)

N-(2-bromo-6-fluorophenyl)-6,6-dimethyl-3-[1-(trimethylsilyl)cyclobutanecarboxamido]-4,6-dihydropyrrolo[3,4-c]pyrazole-5(1H)-carboxamide (Compound No. II-121)

N-(2-bromo-6-methylphenyl)-6,6-dimethyl-3-[1-(trimethylsilyl)cyclobutanecarboxamido]-4,6-dihydropyrrolo[3,4-c]pyrazole-5(1H)-carboxamide (Compound No. II-299)

N-(2-chloro-5-methylphenyl)-6,6-dimethyl-3-[1-(trimethylsilyl)cyclobutanecarboxamido]-4,6-dihydropyrrolo[3,4-c]pyrazole-5(1H)-carboxamide (Compound No. II-213)

N-(6-fluoro-2,3-dihydrobenzofuran-7-yl)-6,6-dimethyl-3-[1-(trimethylsilyl)cyclobutanecarboxamido]-4,6-dihydropyrrolo[3,4-c]pyrazole-5(1H)-carboxamide (Compound No. II-997)

N-(2-cyano-6-fluorophenyl)-6,6-dimethyl-3-[1-(trimethylsilyl)cyclobutanecarboxamido]-4,6-dihydropyrrolo[3,4-c]pyrazole-5(1H)-carboxamide (Compound No. II-185)

N-(2-chloro-6-cyclopropylphenyl)-6,6-dimethyl-3-[1-(trimethylsilyl)cyclobutanecarboxamido]-4,6-dihydropyrrolo[3,4-c]pyrazole-5(1H)-carboxamide (Compound No. II-231)

N-(2-fluoro-3,6-dimethylphenyl)-6,6-dimethyl-3-[1-(trimethylsilyl)cyclobutanecarboxamido]-4,6-dihydropyrrolo[3,4-c]pyrazole-5(1H)-carboxamide (Compound No. II-669)

N-(6-fluorobenzofuran-7-yl)-6,6-dimethyl-3-[1-(trimethylsilyl)cyclobutanecarboxamido]-4,6-dihydropyrrolo[3,4-c]pyrazole-5(1H)-carboxamide (Compound No. II-1049)

N-(2-chloro-3-fluoro-6-methylphenyl)-6,6-dimethyl-3-[1-(trimethylsilyl)cyclobutanecarboxamido]-4,6-dihydropyrrolo[3,4-c]pyrazole-5(1H)-carboxamide (Compound No. II-747)

N-(2,6-dichloro-4-fluorophenyl)-6,6-dimethyl-3-[1-(trimethylsilyl)cyclobutanecarboxamido]-4,6-dihydropyrrolo[3,4-c]pyrazole-5(1H)-carboxamide (Compound No. II-709)

N-(2-chloro-5-methoxyphenyl)-6,6-dimethyl-3-[1-(trimethylsilyl)cyclobutanecarboxamido]-4,6-dihydropyrrolo[3,4-c]pyrazole-5(1H)-carboxamide (Compound No. II-245)

N-(6-fluoro-3-methylbenzofuran-7-yl)-6,6-dimethyl-3-[1-(trimethylsilyl)cyclobutanecarboxamido]-4,6-dihydropyrrolo[3,4-c]pyrazole-5(1H)-carboxamide (Compound No. II-1061)

N-(2-chloro-6-fluorobenzofuran-7-yl)-6,6-dimethyl-3-[1-(trimethylsilyl)cyclobutanecarboxamido]-4,6-dihydropyrrolo[3,4-c]pyrazole-5(1H)-carboxamide (Compound No. II-1063)

N-(6-fluoro-2-methylbenzofuran-7-yl)-6,6-dimethyl-3-[1-(trimethylsilyl)cyclobutanecarboxamido]-4,6-dihydropyrrolo[3,4-c]pyrazole-5(1H)-carboxamide (Compound No. II-1059)

Among compounds (II), a compound selected from the following compound group is more preferred:

N-(2-fluorophenyl)-6,6-dimethyl-3-[1-(trimethylsilyl)cyclobutanecarboxamido]-4,6-dihydropyrrolo[3,4-c]pyrazole-5(1H)-carboxamide (Compound No. II-3)

6,6-dimethyl-N-(o-tolyl)-3-[1-(trimethylsilyl)cyclobutanecarboxamido]-4,6-dihydropyrrolo[3,4-c]pyrazole-5(1H)-carboxamide (Compound No. II-21)

N-(2-chloro-6-methylphenyl)-6,6-dimethyl-3-[1-(trimethylsilyl)cyclobutanecarboxamido]-4,6-dihydropyrrolo[3,4-c]pyrazole-5(1H)-carboxamide (Compound No. II-215)

N-(5-fluoro-2-methylphenyl)-6,6-dimethyl-3-[1-(trimethylsilyl)cyclobutanecarboxamido]-4,6-dihydropyrrolo[3,4-c]pyrazole-5(1H)-carboxamide (Compound No. II-361)

N-(2,5-dimethylphenyl)-6,6-dimethyl-3-[1-(trimethylsilyl)cyclobutanecarboxamido]-4,6-dihydropyrrolo[3,4-c]pyrazole-5(1H)-carboxamide (Compound No. II-379)

N-(2-chloro-6-fluorophenyl)-6,6-dimethyl-3-[1-(trimethylsilyl)cyclobutanecarboxamido]-4,6-dihydropyrrolo[3,4-c]pyrazole-5(1H)-carboxamide (Compound No. II-113)

N-(2-bromo-6-methylphenyl)-6,6-dimethyl-3-[1-(trimethylsilyl)cyclobutanecarboxamido]-4,6-dihydropyrrolo[3,4-c]pyrazole-5(1H)-carboxamide (Compound No. II-299)

N-(2-fluoro-3,6-dimethylphenyl)-6,6-dimethyl-3-[1-(trimethylsilyl)cyclobutanecarboxamido]-4,6-dihydropyrrolo[3,4-c]pyrazole-5(1H)-carboxamide (Compound No. II-669)

N-(6-fluorobenzofuran-7-yl)-6,6-dimethyl-3-[1-(trimethylsilyl)cyclobutanecarboxamido]-4,6-dihydropyrrolo[3,4-c]pyrazole-5(1H)-carboxamide (Compound No. II-1049)

N-(2-chloro-6-fluorobenzofuran-7-yl)-6,6-dimethyl-3-[1-(trimethylsilyl)cyclobutanecarboxamido]-4,6-dihydropyrrolo[3,4-c]pyrazole-5(1H)-carboxamide (Compound No. II-1063)

N-(6-fluoro-2-methylbenzofuran-7-yl)-6,6-dimethyl-3-[1-(trimethylsilyl)cyclobutanecarboxamido]-4,6-dihydropyrrolo[3,4-c]pyrazole-5(1H)-carboxamide (Compound No. II-1059)

The compound (I) or the pharmacologically acceptable salt thereof may be a single optically active form or may be a mixture of a plurality of optically active forms.

In the case where geometric isomers or rotational isomers are present in the compound (I), these isomers are also included in the scope of the present invention; and in the case where proton tautomers are present therein, these tautomers are also encompassed in the present invention.

The "pharmacologically acceptable salt" according to the present embodiment is not particularly limited as long as being a salt acceptable as a drug, and examples thereof include: salts with inorganic acids such as hydrochloric acid, hydrobromic acid, hydroiodic acid, nitric acid, sulfuric acid, and phosphoric acid; salts with organic carboxylic acids such as acetic acid, fumaric acid, maleic acid, succinic acid, citric acid, tartaric acid, adipic acid, lactic acid, and trifluoroacetic acid; salts with organic sulfonic acids such as methanesulfonic acid, trifluoromethanesulfonic acid, benzenesulfonic acid, p-toluenesulfonic acid, and naphthalenesulfonic acid; salts with alkali metals such as lithium, sodium, and potassium; salts with alkaline earth metals such as calcium and magnesium; and quaternary ammonium salts such as ammonia, morpholine, glucosamine, ethylenediamine, guanidine, diethylamine, triethylamine, dicyclohexylamine, diethanolamine, and piperazine.

The compound (I) or the pharmacologically acceptable salt thereof can form a hydrate or a solvate, and each one or a mixture thereof is encompassed in the present invention.

The compound (I) may contain a non-natural ratio of an atomic isotope for one or more of the constituting atoms. Examples of the atomic isotope include deuterium ($^2$H), tritium ($^3$H), carbon-11 ($^{11}$C), carbon-14 ($^{14}$C), fluorine-18 ($^{18}$F), sulfur-35 ($^{35}$S), and iodine-125 ($^{125}$I). These compounds are useful as therapeutic or prophylactic agents, research reagents, for example, assay reagents, and diagnostic agents, for example, in vivo diagnostic imaging agents. All isotopic variants of the compound (I) are encompassed in the present invention, regardless of whether to be radioactive.

The compound (I) or the pharmacologically acceptable salt thereof can be produced by a method described in, for example, WO 2016/204153.

<2 Immunotherapeutic Agent>

The "immunotherapeutic agent" in the pharmaceutical composition according to the present embodiment is not particularly limited as long as being a drug currently used in the immunotherapy of tumor or a drug that may be used in the future therein. In the present specification, the "immunotherapy" means immunomodulating therapy mediated by the activation of immune response, increase in the number of immune response cells, etc. Examples of the immunotherapeutic agent include agents that inhibits immune checkpoints such as CTLA-4, PD-1, PD-L1, TIM-3, KIR, LAG-3, VISTA, and BTLA (immune checkpoint inhibitors); and agents that activates immunity by stimulating OX40, IL-10R, GITR, CD27, CD28, CD137, ICOS, or the like (immune activators).

Specific examples of the immune checkpoint inhibitors include ipilimumab, tremelimumab, nivolumab, pembrolizumab, pidilizumab, JNJ-63723283, durvalumab (MEDI4736), atezolizumab (RG7446), avelumab (MSB0010718C), BMS-936559, LY3300054, FAZ053, and MPDL3280A.

Specific examples of the immune activators include AM0010, GSK3174998, MOXR0916, PF-04518600, MEDI0562, TRX518, MEDI1873, varlilumab, urelumab, utomilumab, and MEDI-570.

The "immunotherapeutic agent" in the pharmaceutical composition according to the present embodiment may be an antibody. As such an antibody, an anti-CTLA-4 antibody or an anti-PD-1 antibody is preferred, and an anti-PD-1 antibody (e.g., nivolumab, pembrolizumab, and pidilizumab) is more preferred.

The "immunotherapeutic agent" in the pharmaceutical composition according to the present embodiment may be used alone, or two or more thereof may be used in combination.

<3. Pharmaceutical Composition Comprising Compound Represented by Formula (I) or Pharmaceutically Acceptable Salt Thereof, Wherein Pharmaceutical Composition is Administered in Combination with Immunotherapeutic Agent>

Specifically, the pharmaceutical composition according to the present embodiment may be
(i) a pharmaceutical composition wherein a composition comprising the compound (I) or the pharmacologically acceptable salt thereof as an active ingredient, and a composition comprising an immunotherapeutic agent as an active ingredient are administered at the same time or at a different time, or may be
(ii) a pharmaceutical composition comprising the compound (I) or the pharmacologically acceptable salt thereof, and an immunotherapeutic agent as active ingredients.

In the pharmaceutical composition (i), there is no limitation on the times of administration of the composition comprising the compound (I) or the pharmacologically acceptable salt thereof as an active ingredient, and the composition comprising an immunotherapeutic agent as an active ingredient, and these compositions may be administered at the same time or at a different time. In the pharmaceutical composition (i), there is no limitation on a period from the administration of one of the composition comprising the compound (I) or the pharmacologically acceptable salt thereof as an active ingredient, and the composition comprising an immunotherapeutic agent as an active ingredient, to the administration of the other composition, and within a given period when the pharmacological effect of one of the compositions remains (e.g., 1 week, preferably 2 or 3 days, more preferably 1 day, further preferably 2 to 6 hours, still further preferably 1 hour), the administration of the other composition is preferred.

The compound (I) or the pharmacologically acceptable salt thereof, and the immunotherapeutic agent can be used as a pharmaceutical composition, if necessary, by adding an excipient, a lubricant, a binder, a disintegrant, a coating agent, a stabilizer, a tonicity agent, a buffer, a pH adjuster, a solubilizer, a thickener, a preservative, an antioxidant, a sweetener, a colorant, a flavor, or the like. The pharmaceutical composition according to the present embodiment can be appropriately prepared according to a purpose by a method known in the art, for example, a method described in General Rules for Preparations, Japanese Pharmacopoeia 16th edition.

In the pharmaceutical composition according to the present embodiment, the content of the compound (I) or the pharmacologically acceptable salt thereof, and the content of the immunotherapeutic agent can be appropriately adjusted.

The pharmaceutical composition according to the present embodiment can be in a dosage form described in General Rules for Preparations, Japanese Pharmacopoeia 16th edition, for example, a preparation for oral administration such as tablets, capsules, granules, or powders, or a preparation for parenteral administration such as injections (e.g., intravenous administration, subcutaneous administration, intramuscular administration, and intraperitoneal administration), eye drops, nasal drops, suppositories, ointments, lotions, creams, gels, sprays, patches, inhalants, or percutaneous absorption preparations, and a combination thereof.

In the pharmaceutical composition according to the present embodiment, the compound (I) or the pharmacologically acceptable salt thereof, and the immunotherapeutic agent may be contained as active ingredients in separate preparations, or both may be contained as active ingredients in a single preparation (combination preparation).

Examples of the excipient include lactose, mannitol, starch, crystalline cellulose, light anhydrous silicic acid, calcium carbonate, and calcium hydrogen phosphate, and examples of the lubricant include stearic acid, magnesium stearate, and talc. Examples of the binder include starch, hydroxypropylcellulose, hydroxypropylmethylcellulose, and polyvinylpyrrolidone, and examples of the disintegrant include carboxymethylcellulose, low-substituted hydroxypropylmethylcellulose, and calcium citrate. Examples of the coating agent include hydroxypropylmethylcellulose, macrogol, and silicone resins, and examples of the stabilizer include ethyl p-hydroxybenzoate and benzyl alcohol.

Examples of the tonicity agent include glycerin, propylene glycol, sodium chloride, potassium chloride, sorbitol, and mannitol, examples of the buffer include boric acid, boric acid salts, phosphoric acid, phosphoric acid salts, citric acid, citric acid salts, acetic acid, acetic acid salts, ε-aminocaproic acid, and trometamol, and examples of the pH adjuster include hydrochloric acid, citric acid, phosphoric acid, glacial acetic acid, sodium hydroxide, potassium hydroxide, sodium carbonate, and sodium bicarbonate. Examples of the solubilizer include polysorbate 80, polyoxyethylene hydrogenated castor oil 60, macrogol 4000, purified soybean lecithin, and polyoxyethylene (160) polyoxypropylene (30) glycol, and examples of the thickener include cellulose polymers such as hydroxypropylmethylcellulose and hydroxypropylcellulose, polyvinyl alcohol, and polyvinylpyrrolidone. Examples of the stabilizer include edetic acid and sodium edetate, and examples of the preservative include sorbic acid, potassium sorbate, benzalkonium chloride, benzethonium chloride, methyl p-hydroxybenzoate, propyl p-hydroxybenzoate, and chlorobutanol.

Examples of ingredients that may be contained in pharmaceutical compositions for percutaneous administration such as ointments, lotions, creams, gels, patches, and sprays include: absorption promoters such as lauryl alcohol, myristyl alcohol, salicylic acid ethylene glycol, and pyrrothiodecane; fatty acid esters such as diisopropyl adipate, isopropyl myristate, cetyl lactate, myristyl lactate, isopropyl palmitate, diethyl sebacate, hexyl laurate, and cetyl isooctanoate; aliphatic alcohols such as cetyl alcohol, stearyl alcohol, oleyl alcohol, hexadecyl alcohol, and behenyl alcohol; glycols such as propylene glycol, propylenediol, polyethylene glycol, and dipropylene glycol; and surfactants such as sorbitan fatty acid ester, glycerin fatty acid ester, polyoxyethylene sorbitan fatty acid ester, polyoxyethylene glycerin fatty acid ester, polyethylene glycol fatty acid ester, polyoxyethylene alkyl ether, polyoxyethylene castor oil, and polyoxyethylene hydrogenated castor oil.

The dose of the compound (I) or the pharmacologically acceptable salt thereof, and the administration route and dose of the immunotherapeutic agent can be appropriately adjusted according to symptoms, age, a dosage form, etc. In the case of, for example, oral administration, each active ingredient can usually be administered in one portion or several divided portions of 0.01 to 2000 mg, preferably 1 to 500 mg per day.

As for ointments, lotions, creams, or gels, each active ingredient having a concentration usually adjusted to 0.00001% (w/v) to 10% (w/v), preferably 0.001% (w/v) to 5% (w/v) can be administered in one portion or several divided portions.

The pharmaceutical composition according to the present embodiment is preferably used for the treatment or prevention of tumor. Examples of the tumor include: blood cancers such as multiple myeloma, chronic myeloid leukemia, blood tumor, hematological malignancy, childhood leukemia, childhood lymphoma, Hodgkin's disease, lymphocytic lymphoma, cutaneous lymphoma, acute leukemia, chronic leukemia, acute lymphoblastic leukemia, acute myelogenous leukemia, chronic myelogenous leukemia, plasma cell neoplasm, lymphoid neoplasm, and AIDS-related cancer; and solid cancers such as bladder cancer, breast cancer, colon cancer, kidney cancer, liver cancer, lung cancer, small-cell lung cancer, non-small cell lung cancer, head and neck cancer, esophageal cancer, gallbladder cancer, ovary cancer, pancreatic cancer, stomach cancer, uterine cervical cancer, thyroid gland cancer, prostate cancer, skin cancer including squamous cell cancer, fibrosarcoma, rhabdomyosarcoma, astrocytoma, neuroblastoma, glioma and neurilemmoma, melanoma, seminoma, teratocarcinoma, osteosarcoma, xeroderma pigmentosum, keratoacanthoma, follicular thyroid cancer, and Kaposi's sarcoma.

EXAMPLES

Although the present invention will be further specifically described below about the compound according to the present embodiment or the pharmaceutically acceptable salt thereof with reference to Production Examples (Examples 1 to 11), Reference Examples (Reference Examples 1 to 15), and Test Examples (Test Examples 1 to 4), these examples are given for better understanding of the present invention and are not intended to limit the scope of the present invention.

In purification by preparative column chromatography, the following apparatuses were used:
Apparatus 1: EPCLC-W-Prep 2XY A-Type (manufactured by Yamazen Corp., trade name)
Apparatus 2: Purif (trademark)-compact (manufactured by Moritex Corp., trade name)
Apparatus 3: Prominence preparative system (manufactured by Shimadzu Corp., trade name)

The stationary phases used in purification by preparative column chromatography are as follows:
DIOL silica gel: CHROMATOREX (trade name) DIOL MB 100-40/75 (manufactured by Fuji Silysia Chemical Ltd.)
DNH silica gel: CHROMATOREX (trade name) DNH MB 100-40/75 (manufactured by Fuji Silysia Chemical Ltd.)
ODS silica gel: XBridge C18 Prep (trade name), particle size: 5 μm, OBD, size: 19×150 mm (manufactured by Waters Corp.)
CSH ODS silica gel: XSelect CSH C18 Prep (trade name), particle size: 5 μm, OBD, size: 19×150 mm (manufactured by Waters Corp.)
Fluoro-phenyl silica gel: XSelect CSH Prep Fluoro-phenyl (trade name), particle size: 5 μm, OBD, size: 19×150 mm (manufactured by Waters Corp.)

In the case where a plurality of values of mass spectra are observed due to the presence of isotopes, only one having minimum m/z was described. DUIS in an ionization mode of a mass spectrum is a mixed mode of ESI and APCI.

$^1$H-NMR is indicated by chemical shift (δ) with tetramethylsilane as an internal standard (0 ppm), and a coupling constant (J value) is indicated by Hz unit, unless otherwise specified. An abbreviation for the split pattern of each peak has the following meaning: s: singlet, d: doublet, t: triplet, q: quartet, br s: broad singlet, and m: multiplet.

Abbreviations described in Production Examples, Reference Examples, and Test Examples are usually used as meanings generally used in the fields of organic chemistry and pharmacy. Each abbreviation is specifically understood by those skilled in the art as follows.
ATP: Adenosine triphosphate
Boc: tert-Butyloxycarbonyl
Cbz: Benzyloxycarbonyl
CI: Chemical ionization
DIPEA: N,N-Diisopropylethylamine
DMF: N,N-Dimethylformamide
DMSO: Dimethyl sulfoxide
DPPA: Diphenylphosphonyl azide
DTT: dithiothreitol
DUIS: Dual ion source
Et: Ethyl
FBS: Fetal bovine serum
HEPES: N-2-Hydroxyethylpiperazine-N'-2-ethanesulfonic acid
MBP: Myelin basic protein
NADPH: Nicotinamide adenine dinucleotide phosphate
PBMC: Periphery blood mononuclear cell
PBS: Phosphate-buffered aqueous sodium chloride solution
TBS: tert-Butyldimethylsilyl
TEA: Triethylamine
THF: Tetrahydrofuran
Tris: Trishydroxymethylaminomethane

Production Example 1

N-(2-Fluorophenyl)-6,6-dimethyl-3-[1-(trimethylsilyl)cyclobutanecarboxamido]-4,6-dihydropyrrolo[3,4-c]pyrazole-5(1H)-carboxamide (Compound No. II-3)

[Chemical Formula 6]

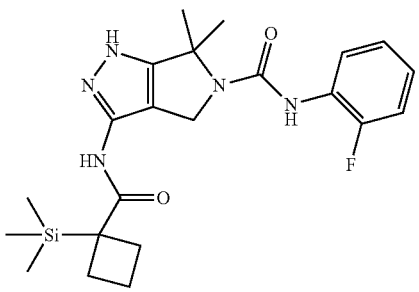

To a solution of 118 mg (0.267 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2 (4H)-carboxylate synthesized in the same way as in Reference Example 4 in 2 ml of 1,4-dioxane, 0.15 ml (0.86 mmol) of DIPEA and 0.080 ml (0.83 mmol) of 2-fluoroaniline were added at room temperature in a nitrogen atmosphere and reacted at 90° C. for 9 hours with stirring. Subsequently, the reaction solution was cooled to room temperature, and 0.15 ml (1.4 mmol) of N,N-dimethylethane-1,2-diamine was added thereto at room temperature and then reacted at room temperature for 2.5 hours with stirring.

After completion of the reaction, ethyl acetate was added to the reaction solution, followed by washing with a 5% aqueous potassium bisulfate solution. After separation into an organic layer and an aqueous layer, the aqueous layer was subjected to extraction twice with ethyl acetate. The whole organic layer thus obtained was dried over anhydrous magnesium sulfate, then filtered, and concentrated under reduced pressure. The obtained concentration residue was subjected to preparative column chromatography (apparatus 2, DIOL silica gel, elution solvent: n-hexane:ethyl acetate=70:30→50:50 (V/V)), and a fraction containing the compound of interest was concentrated under reduced pressure. The obtained concentration residue was dissolved in ethyl acetate, then n-hexane was added thereto, and the deposited solid was collected by filtration, washed with n-hexane, and then dried under reduced pressure to obtain 62.2 mg of the title compound (yield: 53%) as a white solid.

Mass spectrum (CI, m/z): 444 [M+1]$^+$.

$^1$H-NMR spectrum (400 MHz, DMSO-d$_6$) δ: 12.27 & 11.85 (br s, total 1H), 9.80-9.50 (m, 1H), 7.91-7.69 (m, 1H), 7.68-7.47 (m, 1H), 7.24-7.03 (m, 3H), 4.74-4.51 (m, 2H), 2.56-2.39 (m, 2H), 2.28-2.13 (m, 2H), 1.93-1.74 (m, 2H), 1.72-1.57 (m, 6H), 0.09 (s, 9H).

Production Example 2

6,6-Dimethyl-N-(o-tolyl)-3-[1-(trimethylsilyl)cyclobutanecarboxamido]-4,6-dihydropyrrolo[3,4-c]pyrazole-5(1H)-carboxamide (Compound No. II-21)

[Chemical Formula 7]

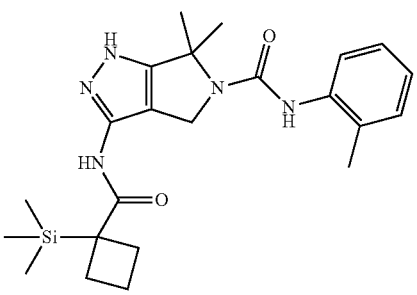

To a solution of 117 mg (0.265 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2 (4H)-carboxylate synthesized in the same way as in Reference Example 4 in 2 ml of 1,4-dioxane, 0.15 ml (0.86 mmol) of DIPEA and 0.090 ml (0.84 mmol) of o-toluidine were added at room temperature in a nitrogen atmosphere and reacted at 90° C. for 5 hours with stirring. Subsequently, the reaction solution was cooled to room temperature, and 0.15 ml (1.4 mmol) of N,N-dimethylethane-1,2-diamine was added thereto at room temperature and then reacted at room temperature for 1.5 hours with stirring.

After completion of the reaction, ethyl acetate was added to the reaction solution, followed by washing with a 5% aqueous potassium bisulfate solution. After separation into an organic layer and an aqueous layer, the aqueous layer was subjected to extraction twice with ethyl acetate. The whole organic layer thus obtained was dried over anhydrous magnesium sulfate, then filtered, and concentrated under reduced pressure. The obtained concentration residue was subjected to preparative column chromatography (apparatus 2, DIOL silica gel, elution solvent: n-hexane:ethyl acetate=70:30→50:50 (V/V)), and a fraction containing the compound of interest was concentrated under reduced pressure. The obtained concentration residue was dissolved in ethyl acetate, then n-hexane was added thereto, and the deposited solid was collected by filtration, washed with n-hexane, and then dried under reduced pressure to obtain 97.7 mg of the title compound (yield: 84%) as a white solid.

Mass spectrum (CI, m/z): 440 [M+1]$^+$.

$^1$H-NMR spectrum (400 MHz, DMSO-d$_6$) δ: 12.26 & 11.83 (br s, total 1H), 9.73-9.49 (m, 1H), 7.76-7.54 (m, 1H), 7.34-7.21 (m, 1H), 7.19-7.07 (m, 2H), 7.02 (dt, J=1.2, 7.4 Hz, 1H), 4.71-4.52 (m, 2H), 2.54-2.40 (m, 2H), 2.27-2.12 (m, 5H), 1.93-1.73 (m, 2H), 1.72-1.54 (m, 6H), 0.09 (s, 9H).

Production Example 3

N-(2-Chloro-6-methylphenyl)-6,6-dimethyl-3-[1-(trimethylsilyl)cyclobutanecarboxamido]-4,6-dihydropyrrolo[3,4-c]pyrazole-5(1H)-carboxamide
(Compound No. II-215)

[Chemical Formula 8]

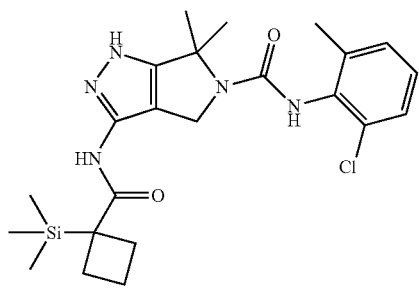

To a solution of 200 mg (0.454 mmol [calculation value with the purity defined as 100%]) of ethyl 5-(chlorocarbonyl)-6,6-dimethyl-3-[1-(trimethylsilyl)cyclobutanecarboxamido]-5,6-dihydropyrrolo[3,4-c]pyrazole-2 (4H)-carboxylate synthesized in the same way as in Reference Example 4 in 3 ml of 1,4-dioxane, 0.39 ml (2.3 mmol) of DIPEA and 0.16 ml (1.4 mmol) of 2-chloro-6-methylaniline were added at room temperature in an argon atmosphere, reacted at 120° C. for 0.5 hours in a microwave reaction apparatus, and then reacted at 150° C. for 2 hours. Subsequently, 0.21 ml (2.3 mmol) of N,N-dimethylethane-1,2-diamine was added thereto at room temperature and then reacted at room temperature for 2 hours with stirring.

After completion of the reaction, a saturated aqueous solution of ammonium chloride was added to the reaction solution, followed by extraction with ethyl acetate. The whole organic layer thus obtained was washed with saturated saline, dried over anhydrous magnesium sulfate, then filtered, and concentrated under reduced pressure. The obtained concentration residue was subjected to preparative column chromatography (apparatus 1, DIOL silica gel, elution solvent: n-hexane:ethyl acetate=70:30→50:50 (V/V)), and a fraction containing the compound of interest was concentrated under reduced pressure. The obtained concentration residue was subjected to preparative column chromatography (apparatus 1, silica gel, elution solvent: 1,2-dichloroethane:methanol=99:1→92:8 (V/V)), and a fraction containing the compound of interest was concentrated under reduced pressure. The obtained concentration residue was subjected to preparative column chromatography (apparatus 3, ODS silica gel, elution solvent: acetonitrile:1 mM aqueous potassium dihydrogen phosphate solution=50:50 (V/V)), and a fraction containing the compound of interest was concentrated under reduced pressure, followed by the distilling off of acetonitrile. The obtained concentrate was subjected to extraction with ethyl acetate, and subsequently, the whole organic layer was washed with saturated saline, then dried over anhydrous magnesium sulfate, filtered, and concentrated under reduced pressure. The obtained concentration residue was dissolved by the addition of ethyl acetate, then n-hexane was added thereto, and the deposited solid was collected by filtration and dried under reduced pressure to obtain 23.6 mg of the title compound (yield: 11% [calculation value with the purity of the starting material defined as 100%]) as a white solid.

Mass spectrum (CI, m/z): 474 $[M+1]^+$.

$^1$H-NMR spectrum (400 MHz, DMSO-$d_6$) δ: 12.26 & 11.73 (br s, total 1H), 9.58 (s, 1H), 7.81 (br s, 1H), 7.30 (dd, J=1.3, 7.8 Hz, 1H), 7.23-7.11 (m, 2H), 4.61 (br s, 2H), 2.56-2.41 (m, 2H), 2.27-2.12 (m, 5H), 1.90-1.73 (m, 2H), 1.64 (s, 6H), 0.09 (s, 9H).

Production Example 4

N-(5-Fluoro-2-methylphenyl)-6,6-dimethyl-3-[1-(trimethylsilyl)cyclobutanecarboxamido]-4,6-dihydropyrrolo[3,4-c]pyrazole-5(1H)-carboxamide
(Compound No. II-361)

[Chemical Formula 9]

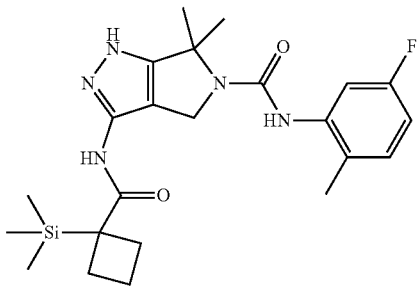

To a solution of 103 mg (0.273 mmol) of ethyl 6,6-dimethyl-3-[1-(trimethylsilyl)cyclobutanecarboxamido]-5,6-dihydro pyrrolo[3,4-c]pyrazole-2(4H)-carboxylate synthesized in the same way as in Reference Example 3 in 2 ml of 1,4-dioxane, 0.085 ml (0.66 mmol) of 5-fluoro-2-methylphenyl isocyanate was added at room temperature in an argon atmosphere and reacted at room temperature for 1 hour with stirring. Subsequently, the reaction solution was cooled in ice, and 0.140 ml (1.29 mmol) of N,N-dimethylethane-1,2-diamine was added thereto and then reacted at 0° C. for 16 hours with stirring.

After completion of the reaction, ethyl acetate was added to the reaction solution, followed by washing with a 5% aqueous potassium bisulfate solution. After separation into an organic layer and an aqueous layer, the aqueous layer was subjected to extraction twice with ethyl acetate. The organic layer was dried over anhydrous magnesium sulfate, then filtered, and concentrated under reduced pressure. The obtained concentration residue was subjected to preparative column chromatography (apparatus 1, DIOL silica gel, elution solvent: n-hexane:ethyl acetate=100:0→50:50 (V/V)), and a fraction containing the compound of interest was concentrated under reduced pressure. The obtained concentration residue was subjected to preparative column chromatography (apparatus 3, ODS silica gel, elution solvent: acetonitrile:1 mM aqueous potassium dihydrogen phosphate solution=40:60 (V/V)), and a fraction containing the compound of interest was subjected to extraction by the addition of ethyl acetate. The obtained organic layer was washed with water, dried over anhydrous sodium sulfate, then filtered, and concentrated under reduced pressure. The obtained concentration residue was dissolved by the addition of methanol, then water was added thereto, and the deposited solid was collected by filtration and dried under reduced pressure to obtain 42.7 mg of the title compound (yield: 34%) as a white solid.

Mass spectrum (CI, m/z): 458 [M+1]$^+$.

$^1$H-NMR spectrum (400 MHz, DMSO-d$_6$) δ: 12.28 & 11.78 (br s, total 1H), 9.60 (br s, 1H), 7.79-7.50 (m, 1H), 7.38-7.11 (m, 2H), 6.83 (dt, J=2.8, 8.4 Hz, 1H), 4.63 (br s, 2H), 2.58-2.39 (m, 2H), 2.27-2.12 (m, 5H), 1.92-1.73 (m, 2H), 1.66 (s, 6H), 0.09 (s, 9H).

Production Example 5

N-(2,5-Dimethylphenyl)-6,6-dimethyl-3-[1-(trimethylsilyl)cyclobutanecarboxamido]-4,6-dihydropyrrolo[3,4-c]pyrazole-5(1H)-carboxamide (Compound No. II-379)

[Chemical Formula 10]

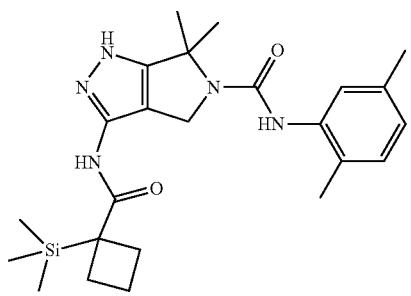

To a solution of 103 mg (0.273 mmol) of ethyl 6,6-dimethyl-3-[1-(trimethylsilyl)cyclobutanecarboxamido]-5,6-dihydro pyrrolo[3,4-c]pyrazole-2(4H)-carboxylate synthesized in the same way as in Reference Example 3 in 3 ml of 1,4-dioxane, 0.060 ml (0.43 mmol) of 2,5-dimethylphenyl isocyanate was added at room temperature in an argon atmosphere and reacted at room temperature for 0.5 hours with stirring. Subsequently, 0.150 ml (1.38 mmol) of N,N-dimethylethane-1,2-diamine was added to the reaction solution at room temperature and then reacted at room temperature for 1 hour with stirring.

After completion of the reaction, a 5% aqueous potassium bisulfate solution was added to the reaction solution, followed by extraction with ethyl acetate. The whole organic layer thus obtained was washed with a saturated aqueous solution of sodium bicarbonate and saturated saline in this order, dried over anhydrous magnesium sulfate, then filtered, and concentrated under reduced pressure. The obtained concentration residue was subjected to preparative column chromatography (apparatus 2, DIOL silica gel, elution solvent: n-hexane:ethyl acetate=90:10→60:40 (V/V)), and a fraction containing the compound of interest was concentrated under reduced pressure. The obtained concentration residue was subjected to preparative column chromatography (apparatus 3, ODS silica gel, elution solvent: acetonitrile:1 mM aqueous dipotassium biphosphate solution=65:35 (V/V)), and a saturated aqueous solution of sodium bicarbonate was added to a fraction containing the compound of interest, followed by extraction with ethyl acetate. The whole organic layer thus obtained was washed with water and saturated saline in this order, dried over anhydrous magnesium sulfate, filtered, and concentrated under reduced pressure. The obtained concentration residue was dissolved by the addition of dichloromethane, then n-hexane was added thereto, and the deposited solid was collected by filtration and dried under reduced pressure to obtain 60.2 mg of the title compound (yield: 49%) as a white solid.

Mass spectrum (CI, m/z): 454 [M+1]$^+$.

$^1$H-NMR spectrum (400 MHz, DMSO-d$_6$) δ: 12.25 & 11.78 (br s, total 1H), 9.67-9.49 (m, 1H), 7.67-7.45 (m, 1H), 7.19-7.06 (m, 1H), 7.03 (d, J=7.6 Hz, 1H), 6.83 (dd, J=1.3, 7.6 Hz, 1H), 4.67-4.50 (m, 2H), 2.57-2.38 (m, 2H), 2.27-2.09 (m, 8H), 1.91-1.72 (m, 2H), 1.65 (br s, 6H), 0.09 (s, 9H).

Production Example 6

N-(2-Chloro-6-fluorophenyl)-6,6-dimethyl-3-[1-(trimethylsilyl)cyclobutanecarboxamido]-4,6-dihydropyrrolo[3,4-c]pyrazole-5(1H)-carboxamide (Compound No. II-113)

[Chemical Formula 11]

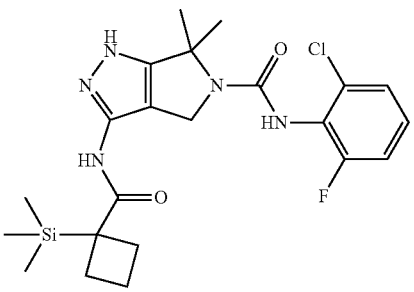

To a solution of 392 mg (0.890 mmol [calculation value with the purity defined as 100%]) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 4 in 2.5 ml of 1,4-dioxane, 0.60 ml (3.4 mmol) of DIPEA and 807 mg (5.54 mmol) of 2-chloro-6-fluoroaniline were added at room temperature in a nitrogen atmosphere, reacted at 100° C. for 1 hour with stirring, and then reacted at 130° C. for 0.5 hours and further at 150° C. for 2 hours in a microwave reaction apparatus. Subsequently, 0.50 ml (4.6 mmol) of N,N-dimethylethane-1,2-diamine was added thereto at room temperature and then reacted at room temperature for 1.5 hours with stirring.

After completion of the reaction, ethyl acetate was added to the reaction solution, followed by washing with a 5% aqueous potassium bisulfate solution. After separation into an organic layer and an aqueous layer, the aqueous layer was subjected to extraction twice with ethyl acetate. The whole organic layer thus obtained was dried over anhydrous magnesium sulfate, then filtered, and concentrated under reduced pressure. The obtained concentration residue was subjected to preparative column chromatography (apparatus 2, DIOL silica gel, elution solvent: n-hexane:ethyl acetate=80:20→65:35→50:50 (V/V)), and a fraction containing the compound of interest was concentrated under reduced pressure. The obtained concentration residue was subjected to preparative column chromatography (apparatus 2, silica gel, elution solvent: dichloromethane:methanol=100:0→99:1→98:2→97:3 (V/V)), and a fraction containing the compound of interest was concentrated under reduced pressure to obtain a white solid (approximately 70 mg). The obtained solid was subjected to preparative column chromatography (apparatus 3, ODS silica gel, elution solvent: acetonitrile:1 mM aqueous dipotassium biphosphate solution=50:50→80:20 (V/V)), and a fraction containing the compound of interest was concentrated under reduced pressure, followed by the distilling off of acetonitrile. The obtained concentration residue was subjected to extraction three times with ethyl acetate, and subsequently, the whole organic layer was washed with saturated saline, then dried over anhydrous magnesium sulfate, filtered, and concentrated under reduced pressure. The obtained concentration residue was dissolved in ethyl acetate, then n-hexane was added thereto, and the deposited solid was collected by filtration, washed with n-hexane, and then dried under reduced pressure to obtain 57.1 mg of the title compound (yield: 13% [calculation value with the purity of the starting material defined as 100%]) as a white solid.

Mass spectrum (CI, m/z): 478 [M+1]$^+$.

$^1$H-NMR spectrum (400 MHz, DMSO-d$_6$) δ: 12.27 & 11.69 (br s, total 1H), 9.64-9.54 (m, 1H), 8.09-7.89 (m, 1H), 7.38-7.19 (m, 3H), 4.69-4.52 (m, 2H), 2.56-2.39 (m, 2H), 2.28-2.13 (m, 2H), 1.93-1.73 (m, 2H), 1.70-1.54 (m, 6H), 0.15-0.04 (in, 9H).

Production Example 7

N-(2-Bromo-6-methylphenyl)-6,6-dimethyl-3-[1-(trimethylsilyl)cyclobutanecarboxamido]-4,6-dihydropyrrolo[3,4-c]pyrazole-5(1H)-carboxamide (Compound No. II-299)

[Chemical Formula 12]

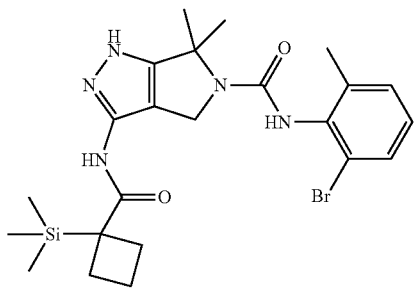

To a solution of 340 mg (1.58 mmol) of 2-bromo-6-methylbenzoic acid in 2 ml of dehydrated toluene, 0.300 ml (1.72 mmol) of DIPEA and 0.340 ml (1.58 mmol) of DPPA were added at room temperature in an argon atmosphere and reacted at room temperature for 0.5 hours and subsequently at 100° C. for 1 hour with stirring. The reaction solution was cooled, and then, a solution of 500 mg (1.32 mmol) of ethyl 6,6-dimethyl-3-[1-(trimethylsilyl)cyclobutanecarboxamido]-5,6-dihydro pyrrolo[3,4-c]pyrazole-2(4H)-carboxylate synthesized in the same way as in Reference Example 3 in 2 ml of dehydrated toluene was added thereto at room temperature and reacted at room temperature for 1 hour with stirring.

After completion of the reaction, water was added to the reaction solution, followed by extraction with ethyl acetate. The obtained organic layer was washed with a saturated aqueous solution of sodium chloride, then dried over anhydrous sodium sulfate, filtered, and concentrated under reduced pressure. The obtained concentration residue was subjected to preparative column chromatography (apparatus 1, DIOL silica gel, elution solvent: n-hexane:ethyl acetate=100:0→60:40 (V/V)), and a fraction containing ethyl 5-[(2-bromo-6-methylphenyl)carbamoyl]-6,6-dimethyl-3-[1-(trimethylsilyl)cyclobutanecarboxamido]-5,6-dihydropyrrolo[3,4-c]pyrazole-2(4H)-carboxylate was concentrated under reduced pressure.

To a solution of the obtained concentration residue in 2 ml of dehydrated dichloromethane, 0.340 ml (3.12 mmol) of N,N-dimethylethane-1,2-diamine was added at room temperature in an argon atmosphere and reacted at room temperature for 0.5 hours with stirring.

After completion of the reaction, a 5% aqueous potassium bisulfate solution was added to the reaction solution, followed by extraction with dichloromethane. The obtained organic layer was washed with a saturated aqueous solution of sodium bicarbonate and a saturated aqueous solution of sodium chloride in this order, then dried over anhydrous sodium sulfate, filtered, and concentrated under reduced pressure. The obtained concentration residue was subjected to preparative column chromatography (apparatus 1, DIOL silica gel, elution solvent: n-hexane:ethyl acetate=100:0→60:40 (V/V)), and a fraction containing the compound of interest was concentrated under reduced pressure. The obtained concentration residue was dissolved in aqueous acetonitrile and freeze-dried to obtain 507 mg of the title compound (yield: 74%) as a white solid.

Mass spectrum (CI, m/z): 518 [M+1]$^+$.

$^1$H-NMR spectrum (400 MHz, DMSO-d$_6$) δ: 12.25 & 11.75 (br s, total 1H), 9.57 (s, 1H), 7.82 (br s, 1H), 7.49-7.43 (m, 1H), 7.26-7.20 (m, 1H), 7.11-7.03 (m, 1H), 4.61 (br s, 2H), 2.56-2.41 (m, 2H), 2.27-2.13 (m, 5H), 1.89-1.74 (m, 2H), 1.64 (s, 6H), 0.09 (s, 9H).

Production Example 8

N-(2-Fluoro-3,6-dimethylphenyl)-6,6-dimethyl-3-[1-(trimethylsilyl)cyclobutanecarboxamido]-4,6-dihydropyrrolo[3,4-c]pyrazole-5(1H)-carboxamide (Compound No. II-669)

[Chemical Formula 13]

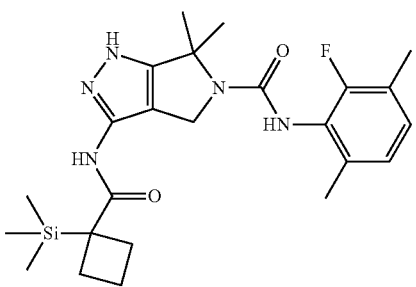

To a solution of 267 mg (1.59 mmol) of 2-fluoro-3,6-dimethylbenzoic acid synthesized in the same way as in Reference Example 8 in 8 ml of toluene, 0.313 ml (1.80 mmol) of DIPEA and 0.353 ml (1.64 mmol) of DPPA were added at room temperature in an argon atmosphere and reacted at room temperature for 0.5 hours and subsequently at 100° C. for 1 hour with stirring. The reaction solution was cooled, and then, a solution of 400 mg (1.06 mmol) of ethyl 6,6-dimethyl-3-[1-(trimethylsilyl)cyclobutanecarboxamido]-5,6-dihydro pyrrolo[3,4-c]pyrazole-2(4H)-carboxylate synthesized in the same way as in Reference Example 3 in 2 ml of toluene was added thereto at 0° C. and reacted at 0° C. for 1 hour with stirring.

After completion of the reaction, a saturated aqueous solution of ammonium chloride was added to the reaction solution, followed by extraction with ethyl acetate. The obtained organic layer was washed with a saturated aqueous solution of sodium chloride, then dried over anhydrous magnesium sulfate, filtered, and concentrated under reduced pressure. The obtained concentration residue was subjected to preparative column chromatography (apparatus 1, silica gel, elution solvent: n-hexane:ethyl acetate=90:10→70:30 (v/v)), and a fraction containing ethyl 5-[(2-fluoro-3,6-dimethylphenyl)carbamoyl]-6,6-dimethyl-3-[1-(trimethylsilyl)cyclobutanecarboxamido]-5,6-dihydropyrrolo[3,4-c]pyrazole-2(4H)-carboxylate was concentrated under reduced pressure.

To a solution of the obtained concentration residue in 5 ml of 1,4-dioxane, 0.494 ml (5.28 mmol) of N,N-dimethylethane-1,2-diamine was added at room temperature in an argon atmosphere and reacted at room temperature for 1 hour with stirring.

After completion of the reaction, a 5% aqueous potassium bisulfate solution was added to the reaction solution, followed by extraction with ethyl acetate. The obtained organic layer was washed with a saturated aqueous solution of sodium chloride, then dried over anhydrous magnesium sulfate, filtered, and concentrated under reduced pressure. The obtained concentration residue was subjected to preparative column chromatography (apparatus 1, DIOL silica gel, elution solvent: n-hexane:ethyl acetate=60:40→40:60 (v/v)), and a fraction containing the compound of interest was concentrated under reduced pressure and dried under reduced pressure. The obtained concentration residue was dissolved in aqueous acetonitrile and freeze-dried to obtain 283 mg of the title compound (yield: 57%) as a white solid.

Mass spectrum (CI, m/z): 472 [M+1]$^+$.

$^1$H-NMR spectrum (400 MHz, DMSO-d$_6$) δ: 12.25 & 11.73 (br s, total 1H), 9.56 (s, 1H), 7.75-7.55 (m, 1H), 7.04-6.96 (m, 1H), 6.91 (d, J=7.8 Hz, 1H), 4.68-4.49 (m, 2H), 2.55-2.40 (m, 2H), 2.26-2.12 (m, 8H), 1.91-1.74 (m, 2H), 1.69-1.55 (m, 6H), 0.09 (s, 9H).

Production Example 9

N-(6-Fluorobenzofuran-7-yl)-6,6-dimethyl-3-[1-(trimethylsilyl)cyclobutanecarboxamido]-4,6-dihydropyrrolo[3,4-c]pyrazole-5(1H)-carboxamide (Compound No. II-1049)

[Chemical Formula 14]

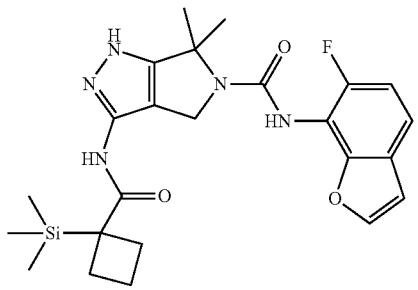

To a suspension of 287 mg (1.59 mmol) of 6-fluorobenzofuran-7-carboxylic acid synthesized in the same way as in Reference Example 5 in 4 ml of dehydrated toluene, 0.360 ml (2.11 mmol) of DIPEA, 0.340 ml (1.58 mmol) of DPPA, and 1 ml of dehydrated dichloromethane were added at room temperature in an argon atmosphere and reacted at room temperature for 1 hour and subsequently at 90° C. for 1 hour with stirring. The reaction solution was cooled, and then, 2 ml of dehydrated dichloromethane was added thereto, and the solution was added dropwise to a solution of 403 mg (1.06 mmol) of ethyl 6,6-dimethyl-3-[1-(trimethylsilyl)cyclobutanecarboxamido]-5,6-dihydro pyrrolo[3,4-c]pyrazole-2(4H)-carboxylate synthesized in the same way as in Reference Example 3 in 4 ml of dichloromethane at 0° C. and reacted at 0° C. for 1 hour with stirring.

After completion of the reaction, a 5% aqueous potassium bisulfate solution was added to the reaction solution, followed by extraction twice with ethyl acetate. The whole organic layer thus obtained was washed with a saturated aqueous solution of sodium bicarbonate and a saturated aqueous solution of sodium chloride in this order, then dried over anhydrous magnesium sulfate, filtered, and concentrated under reduced pressure. The obtained concentration residue was subjected to preparative column chromatography (apparatus 1, silica gel, elution solvent: n-hexane:ethyl acetate=59:41→39:61 (V/V)), and a fraction containing ethyl 5-[(6-fluorobenzofuran-7-yl)carbamoyl]-6,6-dimethyl-3-[1-(trimethylsil yl)cyclobutanecarboxamido]-5,6-dihydropyrrolo[3,4-c]pyrazole-2(4H)-carboxylate was concentrated under reduced pressure.

To a solution of the obtained concentration residue in 3 ml of dehydrated tetrahydrofuran, 0.540 ml (4.96 mmol) of N,N-dimethylethane-1,2-diamine was added at room temperature in an argon atmosphere and reacted at room temperature for 45 minutes with stirring.

After completion of the reaction, a 5% aqueous potassium bisulfate solution was added to the reaction solution, followed by extraction twice with ethyl acetate. The whole organic layer thus obtained was washed with a saturated aqueous solution of sodium bicarbonate and a saturated aqueous solution of sodium chloride in this order, then dried over anhydrous magnesium sulfate, filtered, and concentrated under reduced pressure. The obtained concentration residue was subjected to preparative column chromatography (apparatus 1, DIOL silica gel, elution solvent: n-hexane:ethyl acetate=49:51→28:72 (V/V)), and a fraction containing the compound of interest was concentrated under reduced pressure. The obtained concentration residue was dissolved in aqueous acetonitrile and freeze-dried to obtain 396 mg of the title compound (yield: 77%) as a white solid.

Mass spectrum (CI, m/z): 484 [M+1]$^+$.

$^1$H-NMR spectrum (400 MHz, DMSO-d$_6$) δ: 12.27 & 11.71 (s, total 1H), 9.58 (s, 1H), 8.23-8.04 (m, 1H), 8.00 (d, J=2.2 Hz, 1H), 7.48 (dd, J=4.8, 8.6 Hz, 1H), 7.14 (dd, J=8.6, 10.4 Hz, 1H), 6.97 (d, J=2.2 Hz, 1H), 4.76-4.55 (m, 2H), 2.55-2.40 (m, 2H), 2.28-2.12 (m, 2H), 1.94-1.74 (m, 2H), 1.72-1.55 (m, 6H), 0.09 (s, 9H).

Production Example 10

N-(2-Chloro-6-fluorobenzofuran-7-yl)-6,6-dimethyl-3-[1-(trimethylsilyl)cyclobutanecarboxamido]-4,6-dihydropyrrolo[3,4-c]pyrazole-5(1H)-carboxamide (Compound No. II-1063)

[Chemical Formula 15]

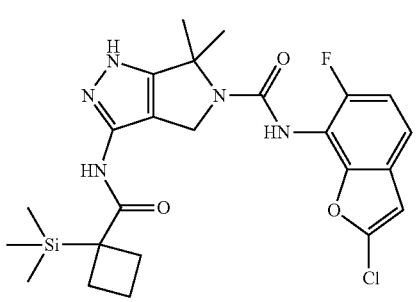

To a solution of 210 mg (0.356 mmol) of ethyl 5-[(2-chloro-6-fluorobenzofuran-7-yl)carbamoyl]-6,6-dimethyl-3-[1-(tri methylsilyl)cyclobutanecarboxamido]-5,6-dihydropyrrolo[3,4-c]pyrazole-2(4H)-carboxylate synthesized in Reference Example 12 in 5 ml of THF, 0.12 ml (1.1 mmol) of N,N-dimethylethane-1,2-diamine was added at room temperature and then reacted at room temperature for 1 hour with stirring.

After completion of the reaction, ethyl acetate was added to the reaction solution, followed by washing with a 5% aqueous potassium bisulfate solution. After separation into an organic layer and an aqueous layer, the obtained organic layer was washed with a saturated aqueous solution of sodium bicarbonate, then dried over anhydrous magnesium sulfate, filtered, and concentrated under reduced pressure. The obtained concentration residue was subjected to preparative column chromatography (apparatus 1, DIOL silica gel, n-hexane:ethyl acetate=50:50→28:72 (V/V)), and a fraction containing the compound of interest was concentrated under reduced pressure. The obtained concentration residue was dissolved in aqueous acetonitrile and freeze-dried to obtain 164 mg of the title compound (yield: 89%) as a white solid.

Mass spectrum (CI, m/z): 518 [M+1]$^+$.

$^1$H-NMR spectrum (400 MHz, DMSO-d$_6$) δ: 12.28 & 11.78 (br s, total 1H), 9.61 (br s, 1H), 8.34-8.10 (m, 1H), 7.44 (dd, J=4.8, 8.6 Hz, 1H), 7.20 (dd, J=8.6, 10.7 Hz, 1H), 7.05 (s, 1H), 4.72-4.57 (m, 2H), 2.58-2.41 (m, 2H), 2.28-2.13 (m, 2H), 1.92-1.73 (m, 2H), 1.66 (br s, 6H), 0.10 (s, 9H).

Production Example 11

N-(6-Fluoro-2-methylbenzofuran-7-yl)-6,6-dimethyl-3-[1-(trimethylsilyl)cyclobutanecarboxamido]-4,6-dihydropyrrolo[3,4-c]pyrazole-5(1H)-carboxamide (Compound No. II-1059)

[Chemical Formula 16]

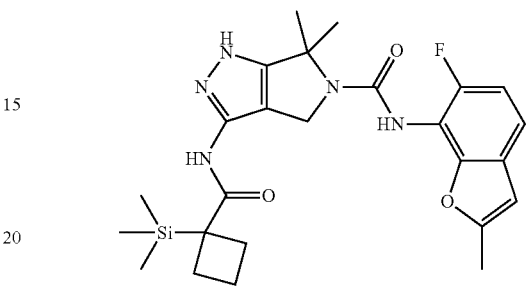

To 144 mg (0.742 mmol) of 6-fluoro-2-methylbenzofuran-7-carboxylic acid synthesized in Reference Example 15, 2 ml of toluene was added, followed by azeotropic dehydration under reduced pressure. To a suspension of the obtained residue in 2 ml of dehydrated toluene, 0.170 ml (1.22 mmol) of triethylamine and 0.200 ml (0.929 mmol) of DPPA were added at room temperature in an argon atmosphere and then reacted at room temperature for 35 minutes and subsequently at 85° C. for 1.5 hours with stirring. The reaction solution was cooled and then added in divided portions to a solution of 232 mg (0.613 mmol) of ethyl 6,6-dimethyl-3-[1-(trimethylsilyl)cyclobutanecarboxamido]-5,6-dihydro pyrrolo[3,4-c]pyrazole-2(4H)-carboxylate synthesized in the same way as in Reference Example 3 in 3 ml of dehydrated toluene at 0° C. and reacted at 0° C. for 1 hour with stirring.

After completion of the reaction, the reaction solution was separated into an organic layer and an aqueous layer by the addition of water and ethyl acetate, and then, the organic layer was washed with a saturated aqueous solution of sodium bicarbonate, dried over anhydrous magnesium sulfate, filtered, and concentrated under reduced pressure. The obtained concentration residue was subjected to preparative column chromatography (apparatus 1, silica gel, n-hexane:ethyl acetate=63:37→42:58 (V/V)), and a fraction containing ethyl 5-[(6-fluoro-2-methylbenzofuran-7-yl)carbamoyl]-6,6-dimethyl-3-[1-(trimethylsilyl)cyclobutanecarboxamido]-5,6-dihydropyrrolo[3,4-c]pyrazole-2(4H)-carboxylate was concentrated under reduced pressure and dried under reduced pressure.

To a solution of the obtained concentration residue in 5 ml of THF, 0.22 ml (2.0 mmol) of N,N-dimethylethane-1,2-diamine was added at room temperature and then reacted at room temperature for 1 hour with stirring.

After completion of the reaction, ethyl acetate was added to the reaction solution, followed by washing with a 5% aqueous potassium bisulfate solution. After separation into an organic layer and an aqueous layer, the obtained organic layer was washed with a saturated aqueous solution of sodium bicarbonate, then dried over anhydrous magnesium sulfate, filtered, and concentrated under reduced pressure. The obtained concentration residue was subjected to preparative column chromatography (apparatus 1, DIOL silica gel, n-hexane:ethyl acetate=46:54→25:75 (V/V)), and a fraction containing the compound of interest was concentrated under reduced pressure. The obtained concentration residue was dissolved in aqueous acetonitrile and freeze-dried to obtain 230 mg of the title compound (yield: 75%) as a white solid.

Mass spectrum (CI, m/z): 498 [M+1]$^+$.

$^1$H-NMR spectrum (400 MHz, DMSO-d$_6$) δ: 12.27 & 11.81 (br s, total 1H), 9.69-9.49 (m, 1H), 8.16-7.97 (m, 1H), 7.33 (dd, J=5.0, 8.5 Hz, 1H), 7.06 (dd, J=8.5, 10.6 Hz, 1H), 6.60-6.55 (m, 1H), 4.64 (br s, 2H), 2.55-2.40 (m, 5H), 2.26-2.14 (m, 2H), 1.89-1.75 (m, 2H), 1.65 (br s, 6H), 0.10 (s, 9H).

Reference Example 1

1-(Trimethylsilyl)cyclobutanecarboxylic acid

[Chemical Formula 17]

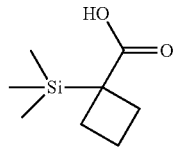

To 200 ml of THF, 214 ml (428 mmol) of a 2 M solution of lithium diisopropylamide in THF was added in an argon atmosphere, and then, 10.1 ml (107 mmol) of cyclobutanecarboxylic acid was added dropwise thereto with stirring under cooling in ice water and reacted for 4 hours while the temperature was raised to room temperature according to the circumstances. Subsequently, 20 ml (116 mmol) of hexamethylphosphoric triamide was added thereto, 51 ml (490 mmol) of chlorotrimethylsilane was added dropwise thereto with stirring with the internal temperature kept at −60° C. or lower under cooling with a dry ice/acetone refrigerant, and then reacted at −78° C. for 16.5 hours with stirring.

After completion of the reaction, 67 ml of methanol was added to the reaction solution, the temperature was raised to 0° C., and then, 134 ml of cold water was added thereto. The resultant was adjusted to pH 2.1 by the addition of 2 N hydrochloric acid and separated into an organic layer and an aqueous layer by the addition of 268 ml of diethyl ether, and the organic layer was washed with 268 ml of a saturated aqueous solution of sodium chloride. The organic layer was dried over anhydrous magnesium sulfate, filtered, and concentrated under reduced pressure. The obtained concentration residue was separated into an organic layer and an aqueous layer by the addition of 50 ml of a 2 N aqueous sodium hydroxide solution and 267 ml of n-hexane. Subsequently, the aqueous layer was adjusted to pH 2.7 by the addition of 1 N hydrochloric acid, and this solution was separated into an organic layer and an aqueous layer by the addition of 267 ml of ethyl acetate. The obtained organic layer was dried over anhydrous magnesium sulfate, filtered, and concentrated under reduced pressure. n-Hexane was added to the obtained concentration residue and cooled in an ice water bath. The resulting solid was filtered, washed with cooled n-hexane, and then dried under reduced pressure to obtain 6.24 g of the title compound (yield: 34%) as a white solid. The filtrate was further concentrated under reduced pressure, and the obtained residue was subjected to silica gel column chromatography (elution solvent: 1,2-dichloroethane:methanol=100:0→95:5 (V/V)), and a fraction containing the compound of interest was concentrated under reduced pressure and dried under reduced pressure to obtain 4.33 g of the title compound (yield: 23%) as a white solid.

Mass spectrum (CI, m/z): 173 [M+1]$^+$.

$^1$H-NMR spectrum (400 MHz, DMSO-d$_6$) δ: 11.64 br s, 1H), 2.45-2.34 (m, 2H), 2.17-2.06 (m, 2H), 1.91-1.70 (m, 2H), 0.06 (s, 9H).

Reference Example 2

5-tert-Butyl 2-ethyl 6,6-dimethyl-3-[1-(trimethylsilyl)cyclobutanecarboxamido]pyrrolo[3,4-c]pyrazole-2,5(4H,6H)-dicarboxylate

[Chemical Formula 18]

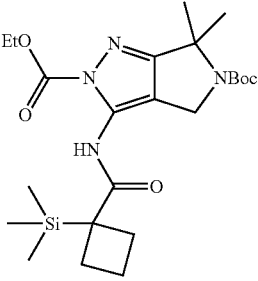

To a solution of 13.9 g (80.4 mmol) of 1-(trimethylsilyl) cyclobutanecarboxylic acid synthesized in the same way as in Reference Example 1 in 105 ml of dichloromethane, 6.96 ml (81.2 mmol) of oxalyl chloride and 0.32 ml (4.14 mmol) of DMF were added dropwise in this order between −25° C. and −10° C. in an argon atmosphere, then the temperature was raised to 0° C., and the resultant was reacted for 2 hours with stirring. This reaction solution was added dropwise into a solution of 8.74 g (26.9 mmol) of 5-tert-butyl 2-ethyl 3-amino-6,6-dimethylpyrrolo[3,4-c]pyrazole-2,5(4H,6H)-dicarboxylate [synthesized according to the method described in Journal of Medicinal Chemistry 2012, 55 (10), 4728-4739] and 23.5 ml (135 mmol) of DIPEA in 122 ml of dichloromethane at 0° C. in an argon atmosphere and reacted at 0° C. for 16 hours with stirring.

After completion of the reaction, the reaction solution was separated into an organic layer and an aqueous layer by the addition of 486 ml of a 5% aqueous potassium bisulfate solution, and then, the aqueous layer was subjected to extraction twice with 200 ml of dichloromethane. The whole organic layer thus obtained was dried over anhydrous magnesium sulfate, filtered, and concentrated under reduced pressure. The obtained concentration residue was subjected to silica gel column chromatography (elution solvent: n-hexane:ethyl acetate=86:14→53:47 (V/V)), and a fraction containing the compound of interest was concentrated under reduced pressure and dried under reduced pressure to obtain 8.30 g of the title compound (yield: 64%) as a white foam.

Mass spectrum (CI, m/z): 479 [M+1]$^+$.

$^1$H-NMR spectrum (400 MHz, DMSO-d$_6$) δ: 9.98 & 9.72 & 9.71 (s, total 1H), 4.50-4.37 (m, 4H), 2.53-2.43 (m, 2H), 2.32-2.07 (m, 2H), 2.02-1.72 (m, 2H), 1.65-1.55 (m, 6H), 1.51-1.42 (m, 9H), 1.38-1.31 (m, 3H), 0.10 & 0.06 & 0.01 (s, total 9H).

Reference Example 3

Ethyl 6,6-dimethyl-3-[1-(trimethylsilyl)cyclobutanecarboxamido]-5,6-dihydropyrrolo[3,4-c]pyrazole-2(4H)-carboxylate

[Chemical Formula 19]

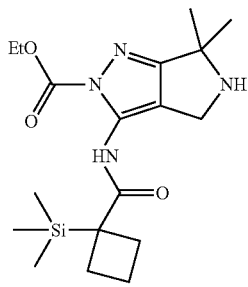

To a solution of 43.2 g (90.0 mmol) of 5-tert-butyl 2-ethyl 6,6-dimethyl-3-[1-(trimethylsilyl)cyclobutanecarboxamido]pyrrolo[3,4-c]pyrazole-2,5(4H,6H)-dicarboxylate synthesized in the same way as in Reference Example 2 in 430 ml of dichloromethane, 30 ml (259 mmol) of 2,6-dimethylpyridine and 46 ml (255 mmol) of trimethylsilyl trifluoromethanesulfonate were added dropwise in this order at 0° C. with stirring in an argon atmosphere and reacted at 0° C. for 1 hour with stirring.

After completion of the reaction, 260 ml of a saturated aqueous solution of sodium bicarbonate and 260 ml of dichloromethane were added to the reaction solution, followed by separation into an organic layer and an aqueous layer. The aqueous layer was subjected to extraction twice with 260 ml of dichloromethane, and then, the whole organic layer thus obtained was washed with 260 ml of a saturated aqueous solution of sodium bicarbonate and 260 ml of saturated saline in this order, subsequently dried over anhydrous magnesium sulfate, filtered, and concentrated under reduced pressure. The operation of adding toluene to the obtained concentration residue and concentrating the resultant under reduced pressure is repeated to obtain 39.7 g of the title compound as a pale yellow solid.

The title compound was also synthesized as follows. To a solution of 57.1 g (119 mmol) of 5-tert-butyl 2-ethyl 6,6-dimethyl-3-[1-(trimethylsilyl)cyclobutanecarboxamido]pyrrolo[3,4-c]pyrazole-2,5(4H,6H)-dicarboxylate synthesized in the same way as in Reference Example 2 in 500 ml of dichloromethane, 28.0 ml (242 mmol) of 2,6-dimethylpyridine and 43.0 ml (238 mmol) of trimethylsilyl trifluoromethanesulfonate were added dropwise in this order at 0° C. in a nitrogen atmosphere and reacted at 0° C. for 2 hours with stirring.

After completion of the reaction, the reaction solution was poured into 1000 ml of a saturated aqueous solution of sodium bicarbonate, then stirred at room temperature, and subsequently separated into an organic layer and an aqueous layer. The aqueous layer was subjected to extraction twice with 500 ml of ethyl acetate, and then, the whole organic layer thus obtained was washed with saturated saline, dried over anhydrous magnesium sulfate, filtered, and concentrated under reduced pressure. The operation of adding toluene to the obtained concentration residue and concentrating the resultant under reduced pressure was performed three times, then the obtained brown oil was refrigerated overnight, and subsequently, 50 ml of diethyl ether and 100 ml of n-hexane were added and stirred at room temperature for 0.5 hours. The deposited solid was collected by filtration, washed with n-hexane, and then dried under reduced pressure to obtain 17.0 g of the title compound (yield: 38%) as a white solid.

Mass spectrum (DUIS, m/z): 379 [M+1]$^+$.

$^1$H-NMR spectrum (400 MHz, CDCl$_3$) δ: 9.86 (s, 1H), 4.52 (q, J=7.1 Hz, 2H), 4.23 (s, 2H), 2.64-2.52 (m, 2H), 2.38-2.27 (m, 2H), 2.03-1.89 (m, 2H), 1.53-1.42 (m, 9H), 0.14 (s, 9H).

Reference Example 4

Ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate

[Chemical Formula 20]

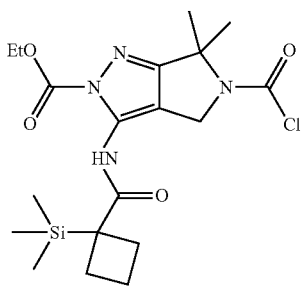

To a solution of 4.90 g (11.1 mmol) of ethyl 6,6-dimethyl-3-[1-(trimethylsilyl)cyclobutanecarboxamido]-5,6-dihydro pyrrolo[3,4-c]pyrazole-2(4H)-carboxylate synthesized in the same way as in Reference Example 3 in 50 ml of dichloromethane, 6.80 ml (39.0 mmol) of DIPEA was added at room temperature in a nitrogen atmosphere, and then, a solution of 2.34 g (7.89 mmol) of bis(trichloromethyl) carbonate in 10 ml of dichloromethane was added dropwise thereto at −78° C. and reacted at −78° C. for 2 hours with stirring.

After completion of the reaction, 80 ml of a saturated aqueous solution of sodium bicarbonate was added to the reaction solution and stirred for 5 minutes. Dichloromethane was added thereto and then stirred while the temperature was raised to room temperature. The reaction solution was separated into an organic layer and an aqueous layer, and then, the aqueous layer was subjected to extraction twice with dichloromethane. The whole organic layer thus obtained was dried over anhydrous magnesium sulfate, filtered, and concentrated under reduced pressure. The obtained concentration residue was subjected to preparative column chromatography (apparatus 2, silica gel, elution solvent: n-hexane:ethyl acetate=90:10→85:15→75:25 (V/V)), and a fraction containing the compound of interest was concentrated under reduced pressure. n-Hexane was added to the obtained concentration residue, and the deposited solid was collected by filtration, washed with n-hexane, and then dried under reduced pressure to obtain 2.00 g of the title compound (yield: 41%) as a white solid. Also, the obtained filtrate was concentrated under reduced pressure and dried under reduced pressure to obtain 2.50 g of the title compound including impurities (yield: 51% [calculation value with the purity defined as 100%]) as a pale yellow foam.

Mass spectrum (DUIS, m/z): 441 [M+1]$^+$.

$^1$H-NMR spectrum (400 MHz, CDCl$_3$) δ: 9.94 (s, 1H), 4.97 (s, 2H), 4.55 (q, J=7.1 Hz, 2H), 2.64-2.53 (m, 2H), 2.39-2.30 (m, 2H), 2.05-1.93 (m, 2H), 1.78 (s, 6H), 1.48 (t, J=7.1 Hz, 3H), 0.16 (s, 9H).

Reference Example 5

6-Fluorobenzofuran-7-carboxylic acid

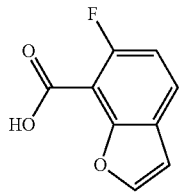

[Chemical Formula 21]

To a solution of 3.76 g (17.5 mmol) of 7-bromo-6-fluorobenzofuran [synthesized according to the method described in EP1204654, pages 14-16] in 50 ml of dehydrated THF, 12.3 ml (19.3 mmol) of a 1.57 M solution of n-butyllithium in n-hexane was added dropwise at −78° C. in a nitrogen atmosphere and reacted at −78° C. for 1 hour with stirring. 36.4 g (827 mmol) of dry ice was added in divided portions thereto at −78° C. and reacted at −78° C. for 1 hour with stirring and subsequently for 6.5 hours while the temperature was raised to room temperature according to the circumstances.

After completion of the reaction, water was added to the reaction solution and then concentrated under reduced pressure, and THF was distilled off. A 1 N aqueous sodium hydroxide solution was added to the obtained concentration residue, followed by washing twice with toluene. The obtained aqueous layer was adjusted to pH 2 by the addition of 6 N hydrochloric acid, followed by extraction three times with ethyl acetate. The whole organic layer thus obtained was washed with a saturated aqueous solution of sodium chloride, then dried over anhydrous magnesium sulfate, filtered, and concentrated under reduced pressure and dried under reduced pressure to obtain 2.91 g of the title compound (yield: 92%) as a light orange solid.

Mass spectrum (CI, m/z): 181 [M+1]$^+$.

$^1$H-NMR spectrum (400 MHz, CDCl$_3$) δ: 7.78 (d, J=2.2 Hz, 1H), 7.75 (dd, J=4.8, 8.6 Hz, 1H), 7.13 (dd, J=8.6, 11.0 Hz, 1H), 6.83 (d, J=2.2 Hz, 1H).

Reference Example 6

Methyl 6-chloro-2-fluoro-3-methylbenzoate

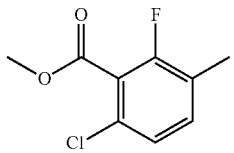

[Chemical Formula 22]

To a solution of 3.00 g (15.9 mmol) of 6-chloro-2-fluoro-3-methylbenzoic acid in 80 ml of DMF, 7.26 g (22.3 mmol) of cesium carbonate and 1.19 ml (19.1 mmol) of methyl iodide were added at room temperature in an argon atmosphere and reacted at room temperature for 2 hours with stirring.

After completion of the reaction, a saturated aqueous solution of ammonium chloride was added to the reaction solution, followed by extraction with ethyl acetate. The obtained organic layer was washed with a saturated aqueous solution of sodium chloride, then dried over anhydrous magnesium sulfate, filtered, and concentrated under reduced pressure. The obtained concentration residue was subjected to preparative column chromatography (apparatus 1, silica gel, elution solvent: n-hexane:ethyl acetate=100:0→95:5 (v/v)), and a fraction containing the compound of interest was concentrated under reduced pressure to obtain 2.81 g of the title compound (yield: 87%) as a colorless oil.

Mass spectrum (CI, m/z): 203 [M+1]$^+$.

$^1$H-NMR spectrum (400 MHz, CDCl$_3$) δ: 7.22-7.15 (m, 1H), 7.14-7.07 (m, 1H), 3.97 (s, 3H), 2.30-2.24 (in, 3H).

Reference Example 7

Methyl 2-fluoro-3,6-dimethylbenzoate

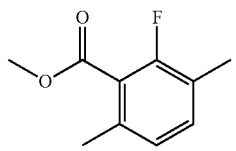

[Chemical Formula 23]

To a solution of 1.00 g (4.94 mmol) of methyl 6-chloro-2-fluoro-3-methylbenzoate synthesized in the same way as in Reference Example 6 in 20 ml of 1,4-dioxane, 2.07 ml (14.8 mmol) of trimethylboroxine, 2.73 g (19.8 mmol) of anhydrous potassium carbonate, and 336 mg (0.493 mmol) of (1,3-diisopropylimidazol-2-ylidene)(3-chloropyridyl)palladium(II) dichloride were added at room temperature in an argon atmosphere and reacted at 100° C. for 2 hours with stirring.

After completion of the reaction, the reaction solution was diluted with ethyl acetate and filtered through a membrane filter. A saturated aqueous solution of ammonium chloride was added to the filtrate, followed by extraction with ethyl acetate. The obtained organic layer was washed with a saturated aqueous solution of sodium chloride, then dried over anhydrous magnesium sulfate, filtered, and concentrated under reduced pressure. The obtained concentration residue was subjected to preparative column chromatography (apparatus 1, silica gel, elution solvent: n-hexane:ethyl acetate=100:0→95:5 (v/v)), and a fraction containing the compound of interest was concentrated under reduced pressure to obtain 849 mg of the title compound (yield: 94%) as a colorless oil.

Mass spectrum (CI, m/z): 183 [M+1]$^+$.

$^1$H-NMR spectrum (400 MHz, CDCl$_3$) δ: 7.12 (t, J=7.8 Hz, 1H), 6.89 (d, J=7.8 Hz, 1H), 3.93 (s, 3H), 2.34 (s, 3H), 2.27-2.22 (in, 3H).

Reference Example 8

2-Fluoro-3,6-dimethylbenzoic acid

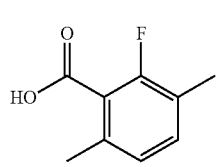

[Chemical Formula 24]

To a solution of 843 mg (4.63 mmol) of methyl 2-fluoro-3,6-dimethylbenzoate synthesized in the same way as in Reference Example 7 in 5 ml of THF and 10 ml of water, 332 mg (13.9 mmol) of lithium hydroxide was added at room temperature in an argon atmosphere and reacted at room temperature for 15 hours and at 80° C. for 8 hours with stirring.

After completion of the reaction, a saturated aqueous solution of ammonium chloride was added to the reaction solution, followed by extraction with ethyl acetate. The obtained organic layer was washed with a saturated aqueous solution of sodium chloride, then dried over anhydrous magnesium sulfate, filtered, and concentrated under reduced pressure. The obtained concentration residue was subjected to preparative column chromatography (apparatus 1, silica gel, elution solvent: n-hexane:ethyl acetate=50:50→30:70 (v/v)), and a fraction containing the compound of interest was concentrated under reduced pressure to obtain 565 mg of the title compound (yield: 73%) as a white solid.

Mass spectrum (CI, m/z): 169 [M+1]$^+$.

$^1$H-NMR spectrum (400 MHz, DMSO-d$_6$) δ: 13.42 (br s, 1H), 7.23 (t, J=7.9 Hz, 1H), 6.99 (d, J=7.9 Hz, 1H), 2.28 (s, 3H), 2.22-2.18 (in, 3H).

Reference Example 9 tert-Butyl 6-fluorobenzofuran-7-carboxylate

[Chemical Formula 25]

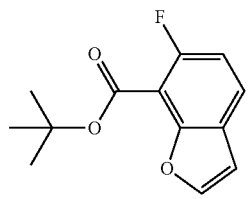

To a solution of 500 mg (2.78 mmol) of 6-fluorobenzofuran-7-carboxylic acid synthesized in Reference Example 5 in 5 ml of pyridine, 1167 mg (6.12 mmol) of p-toluenesulfonyl chloride was added in divided portions at 0° C. in an argon atmosphere and then stirred at 0° C. for 15 minutes with stirring. Subsequently, 0.260 ml (2.74 mmol) of tert-butanol was added thereto at 0° C., then the temperature was raised to room temperature, and the resultant was stirred for 1.5 hours. Further, 0.270 ml (2.84 mmol) of tert-butanol was added thereto and then reacted at room temperature for 16 hours.

After completion of the reaction, the reaction solution was concentrated under reduced pressure, 20 ml of water was added to the obtained concentration residue, and then, the pH was adjusted to 8 with a 2 N aqueous sodium hydroxide solution. After separation into an organic layer and an aqueous layer by the addition of 40 ml of ethyl acetate, the organic layer was washed three times with 10 ml of a 5% aqueous potassium bisulfate solution and once with 10 ml of a saturated aqueous solution of sodium chloride, then dried over anhydrous magnesium sulfate, and filtered, and the filtrate was concentrated under reduced pressure and dried under reduced pressure to obtain 632 mg of the title compound (yield: 96%) as a brown oil.

Mass spectrum (EI, m/z): 236 [M]$^+$.

$^1$H-NMR spectrum (400 MHz, CDCl$_3$) δ: 7.71 (d, J=2.3 Hz, 1H), 7.61 (dd, J=4.9, 8.5 Hz, 1H), 7.05 (dd, J=8.5, 10.8 Hz, 1H), 6.77 (d, J=2.3 Hz, 1H), 1.65 (s, 9H).

Reference Example 10 tert-Butyl 2-chloro-6-fluorobenzofuran-7-carboxylate

[Chemical Formula 26]

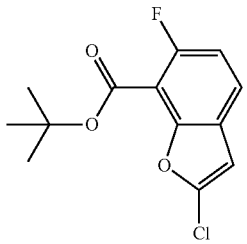

To a solution of 632 mg (2.67 mmol) of tert-butyl 6-fluorobenzofuran-7-carboxylate synthesized in Reference Example 9 in 5 ml of dehydrated DMF, 505 mg (3.78 mmol) of N-chlorosuccinimide was added at room temperature with stirring in an argon atmosphere and then reacted at room temperature for 1 hour, at 50° C. for 6 hours, and further at room temperature for 15.5 hours with stirring.

After completion of the reaction, the reaction solution was separated into an organic layer and an aqueous layer by the addition of toluene and water, and then, the aqueous layer was subjected to extraction once with toluene. The whole organic layer thus obtained was washed with a saturated aqueous solution of sodium bicarbonate, a 5% aqueous sodium thiosulfate solution, a saturated aqueous solution of sodium bicarbonate, and a saturated aqueous solution of sodium chloride in this order, then dried over anhydrous magnesium sulfate, filtered, and concentrated under reduced pressure. The obtained concentration residue was subjected to preparative column chromatography (apparatus 1, silica gel, n-hexane:ethyl acetate=99:1→97:3 (V/V)), and a fraction containing the compound of interest was concentrated under reduced pressure and dried under reduced pressure to obtain 0.20 g of the title compound (yield: 28%) as a colorless oil. Mass spectrum (EI, m/z): 270 [M]$^+$.

$^1$H-NMR spectrum (400 MHz, CDCl$_3$) δ: 7.51 (dd, J=4.8, 8.6 Hz, 1H), 7.05 (dd, J=8.6, 10.9 Hz, 1H), 6.58 (s, 1H), 1.65 (s, 9H).

Reference Example 11

2-Chloro-6-fluorobenzofuran-7-carboxylic acid

[Chemical Formula 27]

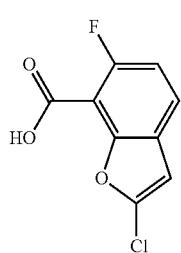

To a solution of 200 mg (0.739 mmol) of tert-butyl 2-chloro-6-fluorobenzofuran-7-carboxylate synthesized in Reference Example 10 in 1.5 ml of dichloromethane, 0.141 ml (1.84 mmol) of trifluoroacetic acid was added at room temperature in an argon atmosphere and then reacted at room temperature for 20 hours with stirring.

After completion of the reaction, the reaction solution was purged with nitrogen gas to distill off the solvent. Diisopropyl ether/n-hexane=1/1 (V/V) was added to the obtained concentration residue and then ultrasonicated, and the obtained solid was collected by filtration. The obtained solid was washed with n-hexane and then dried under reduced pressure at 30° C. to obtain 120 mg of the title compound (yield: 76%) as a white solid.

Mass spectrum (CI, m/z): 215 [M+1]$^+$.

$^1$H-NMR spectrum (400 MHz, CDCl$_3$) δ: 7.63 (dd, J=4.8, 8.7 Hz, 1H), 7.13 (dd, J=8.7, 11.0 Hz, 1H), 6.64 (s, 1H).

Reference Example 12

Ethyl 5-[(2-chloro-6-fluorobenzofuran-7-yl)carbamoyl]-6,6-dimethyl-3-[1-(trimethylsilyl)cyclobutanecarboxamido]-5,6-dihydropyrrolo[3,4-c]pyrazole-2(4H)-carboxylate

[Chemical Formula 28]

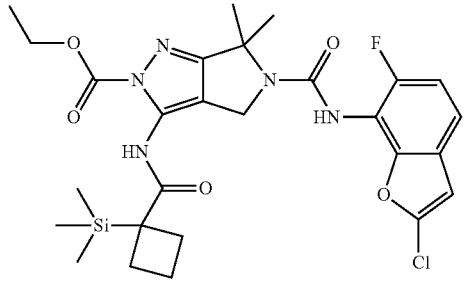

To 116 mg (0.541 mmol) of 2-chloro-6-fluorobenzofuran-7-carboxylic acid synthesized in Reference Example 11, 2 ml of toluene was added, followed by azeotropic dehydration under reduced pressure. To a suspension of the obtained residue in 2 ml of dehydrated toluene, 0.140 ml (1.00 mmol) of triethylamine, 0.155 ml (0.720 mmol) of DPPA, and further 0.5 ml of dichloromethane were added at room temperature in an argon atmosphere and then reacted at room temperature for 40 minutes and subsequently at 85° C. for 1.5 hours with stirring. The reaction solution was cooled, then added in divided portions to a solution of 182 mg (0.481 mmol) of ethyl 6,6-dimethyl-3-[1-(trimethylsilyl)cyclobutanecarboxamido]-5,6-dihydro pyrrolo[3,4-c]pyrazole-2(4H)-carboxylate synthesized in the same way as in Reference Example 3 in 3 ml of dehydrated toluene at 0° C., and reacted at 0° C. for 1 hour with stirring.

After completion of the reaction, the reaction solution was separated into an organic layer and an aqueous layer by the addition of water and ethyl acetate, and then, the organic layer was washed with a saturated aqueous solution of sodium bicarbonate, dried over anhydrous magnesium sulfate, filtered, and concentrated under reduced pressure. The obtained concentration residue was subjected to preparative column chromatography (apparatus 1, silica gel, n-hexane:ethyl acetate=70:30→45:55 (V/V)), and a fraction containing the compound of interest was concentrated under reduced pressure and dried under reduced pressure to obtain 210 mg of the title compound (yield: 74%) as a white foam.

Mass spectrum (CI, m/z): 590 [M+1]$^+$.

$^1$H-NMR spectrum (400 MHz, DMSO-d$_6$) δ: 9.78 (s, 1H), 8.39 (s, 1H), 7.44 (dd, J=4.8, 8.6 Hz, 1H), 7.20 (dd, J=8.6, 10.7 Hz, 1H), 7.05 (s, 1H), 4.78 (s, 2H), 4.43 (q, J=7.1 Hz, 2H), 2.57-2.42 (m, 2H), 2.31-2.20 (m, 2H), 1.95-1.84 (m, 2H), 1.66 (s, 6H), 1.35 (t, J=7.1 Hz, 3H), 0.12 (s, 9H).

Reference Example 13 tert-Butyl 2-bromo-6-fluorobenzofuran-7-carboxylate

[Chemical Formula 29]

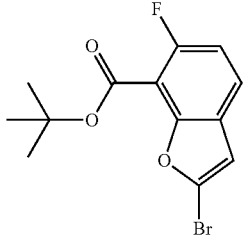

To a solution of 2.26 g (9.57 mmol) of tert-butyl 6-fluorobenzofuran-7-carboxylate synthesized in the same way as in Reference Example 9 in 30 ml of acetonitrile and 10 ml of dehydrated DMF, 1.87 g (10.5 mmol) of N-bromosuccinimide was added at 50° C. in an argon atmosphere and then reacted at 50° C. for 1 hour with stirring. Subsequently, 1.81 g (10.2 mmol) of N-bromosuccinimide was further added thereto and then reacted at 50° C. for 0.5 hours.

After completion of the reaction, the reaction solution was separated into an organic layer and an aqueous layer by the addition of ethyl acetate and water. The obtained organic layer was washed once with a 5% aqueous sodium thiosulfate solution and twice with a saturated aqueous solution of sodium bicarbonate, then dried over anhydrous magnesium sulfate, filtered, and concentrated under reduced pressure. The obtained concentration residue was subjected to preparative column chromatography (apparatus 1, silica gel, n-hexane:ethyl acetate=99:1→97:3 (V/V)), and a fraction containing the compound of interest was concentrated under reduced pressure. The obtained concentration residue was subjected again to preparative column chromatography (apparatus 1, silica gel, n-hexane: ethyl acetate=99:1→98:2 (V/V)), and a fraction containing the compound of interest was concentrated under reduced pressure and dried under reduced pressure to obtain 861 mg of the title compound (yield: 29%) as a pale yellow oil.

Mass spectrum (EI, m/z): 314 [M]$^+$.

$^1$H-NMR spectrum (400 MHz, CDCl$_3$) δ: 7.52 (dd, J=4.8, 8.7 Hz, 1H), 7.05 (dd, J=8.7, 10.8 Hz, 1H), 6.73 (s, 1H), 1.65 (s, 9H).

Reference Example 14 tert-Butyl 6-fluoro-2-methylbenzofuran-7-carboxylate

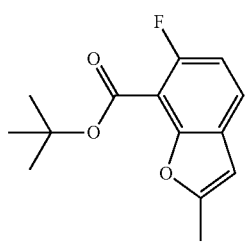

[Chemical Formula 30]

To a heterogeneous solution of 500 mg (1.59 mmol) of tert-butyl 2-bromo-6-fluorobenzofuran-7-carboxylate synthesized in the same way as in Reference Example 13 in 22 ml of toluene and 1.32 ml of water, 1.50 g (7.07 mmol) of anhydrous potassium phosphate and 290 mg (4.84 mmol) of methylboronic acid were added, and then, replacement with an argon atmosphere was performed under reduced pressure under cooling in a dry ice/acetone bath. Subsequently, 10.7 mg (0.048 mmol) of palladium(II) acetate and 35.0 mg (0.098 mmol) of butyl di-1-adamantylphosphine were added thereto and then reacted at 100° C. for 2 hours with stirring.

After completion of the reaction, 5 g of celite was added to the cooled reaction solution, stirred for 10 minutes, and then filtered, and the solid residue was washed with ethyl acetate. The obtained filtrate was separated into an organic layer and an aqueous layer by the addition of water, and then, the organic layer was dried over anhydrous magnesium sulfate, filtered, and concentrated under reduced pressure. The obtained concentration residue was subjected to preparative column chromatography (apparatus 1, silica gel, n-hexane:ethyl acetate=99:1→96:4 (V/V)), and a fraction containing the compound of interest was concentrated under reduced pressure and dried under reduced pressure to obtain 240 mg of the title compound (yield: 60%) as a pale yellow oil.

Mass spectrum (EI, m/z): 250 [M]$^+$.
$^1$H-NMR spectrum (400 MHz, CDCl$_3$) δ: 7.46 (dd, J=4.9, 8.5 Hz, 1H), 6.96 (dd, J=8.5, 10.9 Hz, 1H), 6.35 (q, J=1.0 Hz, 1H), 2.49-2.47 (m, 3H), 1.65 (s, 9H).

Reference Example 15

6-Fluoro-2-methylbenzofuran-7-carboxylic acid

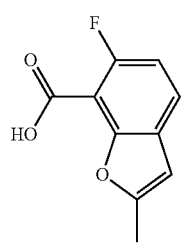

[Chemical Formula 31]

To a solution of 237 mg (0.947 mmol) of tert-butyl 6-fluoro-2-methylbenzofuran-7-carboxylate synthesized in Reference Example 14 in 1.5 ml of dehydrated dichloromethane, 0.181 ml (2.37 mmol) of trifluoroacetic acid was added at room temperature in an argon atmosphere and then reacted at room temperature for 4 hours with stirring. Subsequently, 1.0 ml of dehydrated dichloromethane and 0.181 ml (2.37 mmol) of trifluoroacetic acid were further added thereto and then further reacted for 13.5 hours.

After completion of the reaction, the reaction solution was concentrated under reduced pressure. Diisopropyl ether/n-hexane=1/1 (V/V) was added to the obtained concentration residue and then ultrasonicated, and the obtained solid was collected by filtration, washed with n-hexane, and then dried under reduced pressure at 40° C. to obtain 147 mg of the title compound (yield: 80%) as a white solid. Mass spectrum (CI, m/z): 195 [M+1]$^+$.
$^1$H-NMR spectrum (400 MHz, DMSO-d$_6$) δ: 7.68 (dd, J=5.2, 8.6 Hz, 1H), 7.15 (dd, J=8.6, 11.1 Hz, 1H), 6.67-6.62 (m, 1H), 2.46-2.45 (m, 3H)

Test Example 1

CDK7 Enzyme Inhibition Test

The preparation of a buffer solution was performed by mixing a N-2-hydroxyethylpiperazine-N'-2-ethanesulfonic acid buffer solution (HEPES buffer solution) (pH 7.4), dithiothreitol (DTT), Triton X-100, and magnesium chloride (MgCl$_2$). A 500 μM [γ-$^{33}$P]ATP solution was used by diluting a 10 mM ATP solution and a commercially available [γ-$^{33}$P]ATP solution (manufactured by PerkinElmer, Inc., Code No. NEG-302H) with the buffer solution. A CDK7 solution was used by diluting commercially available CDK7 (manufactured by Carna Biosciences, Inc., Catalog No. 04-108) with the buffer solution. A substrate solution was used by diluting myelin basic protein (MBP) with the buffer solution. As for the preparation of a reaction solution, the buffer solution, the CDK7 solution, and the substrate solution were mixed at 4° C. to obtain a reaction solution.

CDK7 enzyme reaction was performed by adding 5 μL of a test compound solution prepared with 10% DMSO/90% injectable distilled water, and 40 μL of the reaction solution to a 1.5 mL microtube at 4° C. and preincubating the microtube at 25° C. for 60 minutes in a water bath incubator. Subsequently, reaction was performed at 30° C. for 20 minutes by adding 5 μL of the 500 μM [γ-$^{33}$P]ATP solution. After the reaction, a 10% aqueous trichloroacetic acid (TCA) solution was added to each microtube while cooled to 4° C., and mixed in a vortex mixer to terminate the reaction. The resultant was left standing at 4° C. for 10 minutes and then centrifuged, and the supernatant was discarded. Next, a 2% aqueous trichloroacetic acid (TCA) solution was added thereto, mixed in a vortex mixer, and then centrifuged, and the supernatant was discarded. This washing operation was performed twice. After the washing, precipitates were dissolved in a 1 N aqueous sodium hydroxide (NaOH) solution, and the energy quantity (radioactivity) of the reaction product was measured with a liquid scintillation counter.

The calculation of the inhibitory activity of the test compound against CDK7 was performed as a test compound concentration inhibiting 50% of the amount of $^{33}$P bound to MBP (IC$_{50}$ value) by using EXSUS (version 8.1.0, manufactured by CAC Exicare Corp.).

The calculation of a Ki value was performed according to the following calculation expression wherein S represents the concentration of ATP contained in the reaction solution, and Kin represents a Michaelis-Menten constant:

$$Ki=IC_{50}/(1+S/Km)$$

In this test, the compounds of the present invention exhibited excellent CDK7 inhibitory activity. For example, the Ki values of compounds represented by compound Nos. II-3, II-21, II-113, II-215, II-299, II-361, II-379, II-669, II-1049, II-1063, and II-1059 were 50 nM or lower.

Test Example 2

Human Large Intestine Cancer (HCT-116) Cell Growth Inhibition Test

The measurement of a human large intestine cancer cell growth inhibitory effect was carried out by modifying the method of Simak et al. (Cancer Research, 69, 6208 (2009)).

A human large intestine cancer cell line (HCT-116, obtained from DS Pharma Biomedical Co., Ltd.) was cultured in a McCoy's 5A medium (manufactured by Thermo Fisher Scientific, Inc.) containing 10% fetal bovine serum (FBS) (manufactured by Thermo Fisher Scientific, Inc.) and 1% penicillin/streptomycin/amphotericin B (manufactured by Thermo Fisher Scientific, Inc.) and inoculated at 0.5 to $2.0 \times 10^3$ cells/well in a 96-well plate. After overnight culture in a carbon dioxide incubator, culture was further performed for 3 days in a medium supplemented with a solution of a test compound in DMSO (final DMSO concentration: 0.1%), and then, the absorbance thereof was measured by using In Vitro Toxicology Assay Kit Sulforhodamine B based (manufactured by Sigma-Aldrich Co. LLC.).

The rate of inhibition of cell growth at each concentration was calculated from the test compound concentration and the absorbance of sulforhodamine B, and the concentration of the test compound necessary for inhibiting 50% of cell growth ($GI_{50}$ value) was calculated by using EXSUS (version 8.1.0, manufactured by CAC Exicare Corp.).

In this test, the compounds of the present invention exhibited excellent HCT-116 cell growth inhibitory activity. For example, the $GI_{50}$ values of compounds represented by compound Nos. II-3, II-21, II-113, II-215, II-299, II-361, II-379, II-669, II-1049, II-1063, and II-1059 were 100 nM or lower.

Test Example 3

Mouse Melanoma (B16F10) Cell Growth Inhibition Test

Mouse melanoma cells (B16F10) (Cell Resource Center for Biomedical Research, Institute of Development, Aging and Cancer, Tohoku University, Cat. No. TKG0348) were cultured in DMEM medium (REF. 11965-092 manufactured by GIBCO/Thermo Fisher Scientific Inc.) containing 10% FBS (REF. 10082-147 manufactured by GIBCO/Thermo Fisher Scientific Inc.), 1% penicillin/streptomycin/amphotericin B (REF. 15240-096 manufactured by GIBCO/Thermo Fisher Scientific Inc.), and 1 mM sodium pyruvate (REF. 11360-070 manufactured by GIBCO/Thermo Fisher Scientific Inc.) and inoculated at 0.5 to $2.0 \times 10^3$ cells/well to a 96-well plate. After overnight culture in a carbon dioxide incubator, culture was further performed for 3 days in a medium containing a solution of a test compound in DMSO (final DMSO concentration: 0.1%), and then, the amount of ATP was measured using CellTiter-Glo (manufactured by Promega Corp.).

The rate of inhibition of cell growth at each concentration was calculated from the test compound concentration and the amount of ATP, and the concentration of the test compound necessary for inhibiting 50% of cell growth ($GI_{50}$ value) was calculated by using EXSUS (version 8.1.0, manufactured by CAC Croit Corp.).

In this test, the compounds of the present invention exhibited excellent B16F10 cell growth inhibitory activity. For example, the $GI_{50}$ values of compounds represented by compound Nos. II-21, II-113, II-215, II-299, II-361, II-379, II-669, II-1049, II-1063 and II-1059 were 2 μM or lower.

Test Example 4

In Vivo Tumor Growth Inhibition Test in Mouse Melanoma Cell (B16F10)-Subcutaneously Transplanted Mouse Mouse melanoma cells (B16F10) (Cell Resource Center for Biomedical Research, Institute of Development, Aging and Cancer, Tohoku University, Cat. No. TKG0348) were cultured in DMEM medium (REF. 11965-092 manufactured by GIBCO/Thermo Fisher Scientific Inc.) containing 10% FBS (REF. 10082-147 manufactured by GIBCO/Thermo Fisher Scientific Inc.), 1% penicillin/streptomycin/amphotericin B (REF. 15240-096 manufactured by GIBCO/Thermo Fisher Scientific Inc.), and 1 mM sodium pyruvate (REF. 11360-070 manufactured by GIBCO/Thermo Fisher Scientific Inc.) and adjusted to $1.0 \times 10^7$ cells/mL with PBS (REF. 10010-031 manufactured by GIBCO/Thermo Fisher Scientific Inc.). The prepared cell suspension was subcutaneously injected at 0.1 mL/mouse to the right abdomens of C57BL/6 mice (female, supplied by Japan SLC, Inc.). After rearing for a certain period, the long diameter (mm) and short diameter (mm) of tumor were measured with electronic calipers (manufactured by Mitsutoyo Corp., Cat. 500-712-10), and the tumor volume was calculated according to the following expression:

$$\text{Tumor volume (mm}^3\text{)}=(\text{Long diameter})\times(\text{Short diameter})\times(\text{Short diameter})\times 0.5$$

Individuals whose tumor volume was within the range of 50 to 200 mm³ were selected and grouped such that the tumor volume was almost equivalent, then an anti-PD-1 antibody (manufactured by Bio X Cell) at 250 μg/mouse or Rat $IgG_{2a}$ (manufactured by Bio X Cell) at 250 μg/mouse was intraperitoneally administered, and further a test compound (25 mg/kg or 100 mg/kg) or only a solvent was orally administered to each group. The initial day of the start of administration was defined as day 0, and the anti-PD-1 antibody or Rat $IgG_{2a}$ were intraperitoneally administered on day 0 and day 3, and the test compound or only the solvent was orally administered once a day from day 0 to day 6. On day 7, the long diameter and short diameter of tumor were measured, and the tumor volume was calculated. When the rates of increase in tumor volume from day 0 in the Rat $IgG_{2a}$- and solvent-administered groups were defined as 100%, the rate of inhibition of increase in tumor volume in each group was calculated.

The results are shown in Tables 13 to 15. As for the rate of inhibition of increase in tumor volume in each group in Tables 13 to 15, 10% or more and less than 30% were represented by D, 30% or more and less than 50% were represented by C, 50% or more and less than 70% were represented by B, and 70% or more and less than 90% were represented by A.

TABLE 13

| Oral administration | Intraperitoneal administration | Rate of inhibition of increase in tumor volume |
|---|---|---|
| Only solvent | Anti-PD-1 antibody | C |
| II-215 | $IgG_{2a}$ | B |
| II-215 | Anti-PD-1 antibody | A |

TABLE 14

| Oral administration | Intraperitoneal administration | Rate of inhibition of increase in tumor volume |
|---|---|---|
| Only solvent | Anti-PD-1 antibody | C |
| II-379 | IgG$_{2a}$ | B |
| II-379 | Anti-PD-1 antibody | A |

TABLE 15

| Oral administration | Intraperitoneal administration | Rate of inhibition of increase in tumor volume |
|---|---|---|
| Only solvent | Anti-PD-1 antibody | D |
| II-1063 | IgG$_{2a}$ | D |
| II-1063 | Anti-PD-1 antibody | B |

In this test, the compounds of the present invention exhibited excellent tumor volume increase inhibitory activity in combined use with the anti-PD-1 antibody, and, for example, compound Nos. II-215, II-379, and II-1063 exhibited an excellent rate of inhibition of increase in tumor volume, as shown in Tables 13 to 15, when used in combination with the anti-PD-1 antibody.

The invention claimed is:

1. A method for treating colon cancer or melanoma in a human in need thereof, the method comprising administering to the human an effective amount of:
   (i) a compound represented by formula (II) or a pharmacologically acceptable salt thereof; and
   (ii) an anti-PD-1 antibody selected from the group consisting of tremelimumab, pidilizumab, and JNJ-63723283;
wherein the compound represented by formula (II) is:

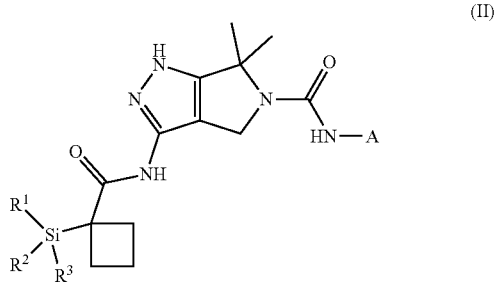

(II)

wherein
A is phenyl optionally substituted with halogen or C$_{1-4}$ alkyl group; or A is benzofuranyl optionally substituted with halogen or C$_{1-4}$ alkyl group; and
R$^1$, R$^2$ and R$^3$ are each independently a linear C$_{1-4}$ alkyl group.

2. The method of claim 1, wherein R$^1$, R$^2$ and R$^3$ are each methyl.

3. The method of claim 1, wherein A is phenyl substituted with halogen or methyl; or A is benzofuranyl substituted with halogen.

4. The method of claim 1, wherein the compound represented by formula (II) is:
N-(2-fluorophenyl)-6,6-dimethyl-3-[1-(trimethylsilyl)cyclobutanecarboxamido]-4, 6-dihydropyrrolo[3,4-c]pyrazole-5(1H)-carboxamide,
6-Dimethyl-N-(o-tolyl)-3-[1-(trimethylsilyl)cyclobutanecarboxamido]-4, 6-dihydropyrrolo[3,4-c]pyrazole-5(1H)-carboxamide,
N-(2-chloro-6-methylphenyl)-6,6-dimethyl-3-[1-(trimethylsilyl) cyclobutanecarboxamido]-4,6-dihydropyrrolo[3,4-c]pyrazole-5(1H)-carboxamide,
N-(5 -fluoro-2-methylphenyl)-6,6-dimethyl-3-[1-(trimethylsilyl)cyclobutanecarboxamido]-4, 6-dihydropyrrolo[3,4-c]pyrazole-5(1H)-carboxamide,
N-(2,5-dimethylphenyl)-6,6-dimethyl-3-[1-(trimethylsilyl)cyclobutanecarboxamido]-4, 6-dihydropyrrolo[3,4-c]pyrazole-5(1H)-carboxamide,
N-(2-chloro-6-fluorophenyl)-6,6-dimethyl-3-[1-(trimethylsilyl) cyclobutanecarboxamido]-4,6-dihydropyrrolo[3,4-c]pyrazole-5(1H)-carboxamide,
N-(2-bromo-6-methylphenyl)-6,6-dimethyl-3-[1-(trimethylsilyl) cyclobutanecarboxamido]-4,6-dihydropyrrolo[3,4-c]pyrazole-5(1H)-arboxamide,
N-(2-fluoro-3,6-dimethylphenyl)-6,6-dimethyl-3-[1-(trimethylsilyl) cyclobutanecarboxamido]-4,6-dihydropyrrolo[3,4-c]pyrazole-5(1H)-carboxamide,
N-(6-fluorobenzofuran-7-yl)-6,6-dimethyl-3-[1-(trimethylsilyl)cyclobutanecarboxamido]-4, 6-dihydropyrrolo[3,4-c]pyrazole-5(1H)-carboxamide,
N-(2-chloro-6-fluorobenzofuran-7-yl)-6,6-dimethyl-3-[1-(trimethylsilyl) cyclobutanecarboxamido]dihydropyrrolo[3-c]pyrazole-5(1H)-carboxamide, or
N-(6-fluoro-2-methylbenzofuran-7-y 1)-6, 6-imethyl-3-[1-(trimethyl silyl) cyclobutanecarboxamido]-4,6-dihydropyrrol o[3,4-c]pyrazole-5(1H)-carboxamide.

5. A method of treating melanoma in a human in need thereof, the method comprising administering to the patient:
an effective amount of a compound selected from the group consisting of:
   (a) N-(2-chloro-6-methylphenyl)-6-6-dimethyl-3-[1-(trimethylsilyl) cyclobutanecarboxamido]4,6-dihydropyrrolo[3, 4-c]pyrazole-5(1H)-carboxamide or a pharmacologically acceptable salt thereof;
   (b) N-(2,5-dimethylphenyl)-6,6-dimethyl-3-[1-(trimethylsilyl) cyclobutanecarboxamido]-4,6-dihydropyrrolo[3, 4-c]pyrazole-5(1H)-carboxamide or a pharmacologically acceptable salt thereof; and
   (c) N-(2-chloro-6-fluorobenzofuran-7-yl)-6,6-dimethyl-3-[1-(trimethylsilyl) cyclobutanecarboxamido]-4,6-dihydropyrrolo[3, 4-c]pyrazole-5(1H)-carboxamide or a pharmacologically acceptable salt thereof; and
(ii) an effective amount of an anti-PD-1 antibody selected from the group consisting of tremelimumab pidilizumab, and JNJ-63723283.

6. The method of claim 5, wherein the anti-PD-1 antibody is tremelimumab.

7. The method of claim 5, wherein the anti-PD-1 antibody is pidilizumab.

8. The method of claim 5, wherein the anti-PD-1 antibody is JNJ-63723283.

9. A method of treating colon cancer in a patient in need thereof, the method comprising administering to the patient:
   (i) an effective amount of a compound selected from the group consisting of:
      (a) N-(2-chloro-6-methylphenyl)-6-6-dimethyl-3-[1-(trimethylsilyl) cyclobutanecarboxamido]4,6-dihydropyrrolo[3, 4-c]pyrazole-5(1H)-carboxamide or a pharmacologically acceptable salt thereof;
      (b) N-(2,5-dimethylphenyl)-6,6-dimethyl-3-[1-(trimethylsilyl) cyclobutanecarboxamido]-4,6-dihydropyrrolo[3, 4-c]pyrazole-5(1H)-carboxamide or a pharmacologically acceptable salt thereof; or
  (c) N-(2-chloro-6-fluorobenzofuran-7-yl)-6,6-dimethyl-3-[1-(trimethylsilyl) cyclobutanecarboxamido]-4,6-dihydropyrrolo[3, 4-c]pyrazole-5(1H)-carboxamide or a pharmacologically acceptable salt thereof; and
(ii) an effective amount of an immunotherapeutic agent selected from the group consisting of tremelimumab pidilizumab, and JNJ-63723283.

10. The method of claim 9, wherein the anti-PD-1 antibody is tremelimumab.

11. The method of claim 9, wherein the anti-PD-1 antibody is pidilizumab.

12. The method of claim 9, wherein the anti-PD-1 antibody is JNJ-63723283.

* * * * *